United States Patent
Harried et al.

(10) Patent No.: US 9,914,708 B2
(45) Date of Patent: *Mar. 13, 2018

(54) BENZOIMIDAZOL-1,2-YL AMIDES AS KV7 CHANNEL ACTIVATORS

(71) Applicant: Knopp Biosciences LLC, Pittsburgh, PA (US)

(72) Inventors: Scott S. Harried, Pittsburgh, PA (US); Lynn Resnick, Pittsburgh, PA (US); George T. Topalov, Pittsburgh, PA (US); Steven A. Boyd, Mars, PA (US); Justin K. Belardi, Pittsburgh, PA (US); Charles A. Flentge, Mars, PA (US); James S. Hale, Pitssburgh, PA (US); David A. Mareska, McMurray, PA (US); Kai Zhang, Wexford, PA (US)

(73) Assignee: Knopp Biosciences LLC, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/339,590

(22) Filed: Oct. 31, 2016

(65) Prior Publication Data

US 2017/0114022 A1    Apr. 27, 2017

Related U.S. Application Data

(63) Continuation of application No. 14/853,815, filed on Sep. 14, 2015, now Pat. No. 9,481,653.

(60) Provisional application No. 62/050,023, filed on Sep. 12, 2014.

(51) Int. Cl.
| | |
|---|---|
| *C07D 235/30* | (2006.01) |
| *C07D 401/12* | (2006.01) |
| *C07D 405/12* | (2006.01) |
| *C07D 403/04* | (2006.01) |
| *C07D 413/04* | (2006.01) |
| *C07D 401/04* | (2006.01) |

(52) U.S. Cl.
CPC ......... *C07D 235/30* (2013.01); *C07D 401/04* (2013.01); *C07D 401/12* (2013.01); *C07D 403/04* (2013.01); *C07D 405/12* (2013.01); *C07D 413/04* (2013.01)

(58) Field of Classification Search
CPC .. C07D 235/30; C07D 401/12; C07D 405/12; C07D 403/04
See application file for complete search history.

(56) References Cited

U.S. PATENT DOCUMENTS

| | | | | |
|---|---|---|---|---|
| 6,855,714 | B2 | 2/2005 | Blume et al. | |
| 7,501,447 | B2 | 3/2009 | Liu et al. | |
| 9,481,653 | B2 * | 11/2016 | Resnick | C07D 235/30 |
| 2011/0124858 | A1 | 5/2011 | Iwata et al. | |

FOREIGN PATENT DOCUMENTS

| | | |
|---|---|---|
| JP | 07/072181 B | 8/1995 |
| WO | 2016/040952 A2 | 3/2016 |

OTHER PUBLICATIONS

International Search Report and Written Opinion for International Application No. PCT/US2015/050027 filed on Sep. 14, 2015.
Pubchem. Substance Record for SID 128950369. Deposit Date: Dec. 4, 2011. [retrieved on Oct. 15, 2015]. Retrieved from the Internet. <URL: https://pubchem.ncbi.nlm.nih.gov/substance/128950369/version/1>. entire document.
Pubchem. Substance Record for SID 131669753. Deposit Date: Jan. 24, 2012. [retrieved on Nov. 30, 2015]. Retrieved from the Internet. <URL: https://pubchem.ncbi.nlm.nih.gov/substance/131669753/version/1#section=Top >. entire document.
Chemical Abstracts Registry No. 689297-99-2, indexed in the Registry file on STN CAS Online Jun. 4, 2004.
Chemical Abstracts Registry No. 1298089-85-4, indexed in the Registry file on STN CAS Online May 20, 2011.
Dadihoyena et al., Synthesis, 2012, 44(2), pp. 215-218.
Chemical Abstracts Registry No. 1370729-32-0, indexed in the Registry file on STN CAS Online Apr. 27, 2012.
SciFinder Search, No Date Available.
SciFinder Search 2, No Date Available.
SciFinder Search 3, No Date Available.
An English translation of JP 07/07181 B (Goto et al.), dated 1995.
Chemical Abstracts Registry No. 1445709-80-7, indexed in the Registry file on STN CAS Online Jul. 19, 2013.
PubChem CID 21428920, National Center for Biotechnology Information, PubChem Compound Database; CID=21428920, https://pubchem.ncbi.nlm.nih.gov/compound/21428920 (accessed Apr. 27, 2016), create date Dec. 5, 2007.
PubChem CID 60339539, National Center for Biotechnology Information, PubChem Compound Database; CID=60339539, https://pubchem.ncbi.nlm.nih.gov/compound/60339539 (accessed Apr. 27, 2016), create date Oct. 18, 2012.
PubChem CID 60339611, National Center for Biotechnology Information, PubChem Compound Database; CID=60339611, https://pubchem.ncbi.nlm.nih.gov/compound/60339611 (accessed Apr. 27, 2016), create date Oct. 18, 2012.
PubChem CID 47251124, National Center for Biotechnology Information, PubChem Compound Database; CID=47251124, https://pubchem.ncbi.nlm.nih.gov/compound/47251124 (accessed Apr. 27, 2016), create date Nov. 26, 2010.
PubChem CID 52655712, National Center for Biotechnology Information, PubChem Compound Database; CID=52655712, https://pubchem.ncbi.nlm.nih.gov/compound/52655712 (accessed Apr. 27, 2016), create date May 20, 2011.
PubChem CID 53531705, National Center for Biotechnology Information, PubChem Compound Database; CID=53531705, https://pubchem.ncbi.nlm.nih.gov/compound/53531705 (accessed Apr. 27, 2016), create date Dec. 3, 2011.

* cited by examiner

*Primary Examiner* — Laura L. Stockton
(74) *Attorney, Agent, or Firm* — Pepper Hamilton LLP

(57) ABSTRACT

Optionally substituted benzoimidazol-1,2-yl amides, such as compounds of Formula 1 or Formula 2, can be used to treat disorders associated with a Kv7 potassium channel activator. Compositions, medicaments, and dosage forms related to the treatment are also disclosed herein.

16 Claims, No Drawings

BENZOIMIDAZOL-1,2-YL AMIDES AS KV7 CHANNEL ACTIVATORS

CROSS-REFERENCE TO RELATED CASES

The present application is a continuation of U.S. patent application Ser. No. 14/853,815, (U.S. Publication No. 2016-0075663 A1) filed Sep. 14, 2015, which claims the benefit of U.S. Provisional application No. 62/050,023, filed Sep. 12, 2014, the entire disclosure of which is incorporated herein by reference.

BACKGROUND

Potassium ($K^+$) channels, present on the plasma membranes of most cell types, are the most diverse class of all ion channels and are associated with a wide range of physiological functions including the regulation of the electrical properties of excitable cells. The primary pore-forming (α) subunits of these highly selective cation channels are divided into three primary structural classes based on the number of transmembrane (TM)-spanning regions and pore (P) regions: currently there are known to be 6TM/1P, 2TM/1P and 4TM/2P $K^+$ channels. The Kv7 genes (originally termed KCNQ, a name assigned by the HUGO Gene Nomenclature Committee (HGNC)) were assigned to a subfamily of voltage-gated $K^+$ channels by the International Union of Pharmacology (IUPHAR). The Kv7 subfamily consists of five homologous pore-forming a subunits, Kv7.1-7.5, that have a structure typical of voltage-gated $K^+$ channels with 6TM-spanning regions (S1-S6) flanked by intracellular N-terminal and C-terminal domains, a typical voltage-sensor domain located in S4 comprised of alternating positively-charged residues and a single P region between S5 and S6 of each subunit. The channels are formed as tetramers of the primary a subunits, either as homotetramers or heterotetramers. Neurons are known to express Kv7 channels comprised of Kv7.2-7.5α subunits. Some of these gene products may be exclusively neuronal while others, such as Kv7.4 and Kv7.5, can be found in other tissues such as smooth and skeletal muscle.

Native M-channels, and the corresponding macroscopic M-current, were first characterized in amphibian sympathetic neurons. M-channels were notable because they were slowly activating and non-inactivating, active at membrane potentials at or near the resting membrane potential of neurons and muscarinic cholinergic agonists produced a reduction in the M-current, demonstrating a direct and inhibitory link between G-protein coupled receptors (GPCRs) and a physiological $K^+$ current. It was not until the cloning of this subfamily of genes that the pharmacological and biophysical identity was established between Kv7.2/7.3 (and likely Kv7.5/7.3) heteromultimers and the elusive 'M'-channel, providing significant new evidence for their importance in neuronal regulation.

The distributions of these channels, both regionally and developmentally, as well as their biophysical characteristics, support their role in providing enduring resistance to depolarizing excitatory influences. Under physiological conditions, as was demonstrated with native M-channels, they can be very effective at regulating the sub-threshold excitability of certain neuronal populations with significant roles in regulating the frequency and ultimately the pattern of action potential discharge in many types of neurons. Their importance in neuronal regulation was punctuated by the discovery that neuronal Kv7 mutations lead to benign familial neonatal convulsions (BFNC) indicating that reduction or removal of the influence of Kv7.2 and Kv7.3 channels can dramatically alter neuronal excitability. Mutation analyses demonstrated their involvement in BFNC and suggested their utility as targets for anti-epileptic drugs (AEDs).

Unlike established pharmacological terminology for GPCRs, the mode of action of $K^+$ channel modulators, in particular compounds that activate the channel, is still being refined. The application of voltage-clamp techniques to the study of ion channel pharmacology enabled detailed biophysical studies on either whole-cell currents or single channels, allowing some characterization of the nature of compound-channel interactions but not preventing ongoing confusion around the terminology. The term opener or activator is commonly used throughout the literature but does not adequately describe the mode of action of all these 'positive modulator' compounds. In general, openers or activators are expected to increase the open probability of the channel or increase macroscopic current amplitude, but this nomenclature is really too simplistic. For example, retigabine, the first publicly disclosed Kv7 opener, has a complex and interesting profile in that it has inhibitory activity at higher membrane potentials. Neuronal Kv7 channel openers may work in concert with the activity of a channel over the 'normal' activation-voltage range and enhance currents without significantly affecting the activation threshold while others can significantly alter the activation threshold. In addition, some openers appear to remove the voltage-dependence of activation entirely. Whether these effects represent some continuum is currently unclear since the effects are often concentration-dependent. Clearly, the modes of interaction of compounds that can increase channel current are complex and in most cases not well understood and the implications of these profiles on neuronal responsiveness and systems physiology are also unclear. Retigabine is modestly potent, not highly specific, but it is a very effective opener of Kv7.2, Kv7.5 and heteromultimeric Kv7 channels. Its effects are characterized by a significant increase in channel current over a narrow voltage range. As mentioned above, at more positive voltages the opener is less effective and under some conditions channel current significantly decreases at more positive voltages relative to control currents (this 'crossover' voltage-dependence of opener action is a characteristic of many neuronal Kv7 channel openers). This effect is also concentration-dependent and is more pronounced at higher concentrations.

SUMMARY

Described herein are compounds that can be potent and/or at least biased for the Kv7.2/7.3 heteromultimer over the Kv7.4 homomultimer. These compounds may have reduced untoward side effects as compared to retigabine.

Some embodiments include a compound represented by Formula 1:

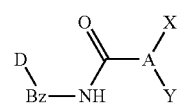

Formula 1 wherein D is optionally substituted $C_{3-6}$ carbocyclyl, $C_{2-5}$ heterocyclyl, or $C_{1-4}$ alkyl; Bz is optionally substituted benzoimidazol-1,2-diyl or optionally substituted benzoimidazol-1,2,6-triyl; A is $C_{1-8}$ alkyl; X is H, F, $CF_3$, optionally substituted phenyl, or optionally substituted pyridinyl; and Y is H, F, Cl, Br, I, or a moiety having a molecular weight of 15 Da to 300 Da and consisting of 2 to 5 chemical elements, wherein the chemical elements are independently C, H, O, N, S, F, Cl, or Br.

Some embodiments include a composition comprising a compound described herein, such as a compound of Formula 1 or Formula 2, wherein the composition is pharmaceutically acceptable.

Some embodiments include a pharmaceutical dosage form comprising a compound described herein, such as a compound of Formula 1 or Formula 2.

Some embodiments include a method of treating a disorder associated with a Kv7 potassium channel activator comprising administering an effective amount of a compound described herein, such as a compound of Formula 1 or Formula 2, to a mammal in need thereof.

Some embodiments include use of a compound of Formula 1 or Formula 2, in the manufacture of a medicament for the treatment of a disorder associated with a Kv7 potassium channel activator.

DETAILED DESCRIPTION

Unless otherwise indicated, when a compound or chemical structural feature such as benzoimidazol-1,2-yl is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art and includes a moiety that replaces one or more hydrogen atoms attached to a parent compound or structural feature. In some embodiments, a substituent may be an ordinary organic moiety known in the art, which may have a molecular weight (e.g. the sum of the atomic masses of the atoms of the substituent) of 15 Da to 50 Da, 15 Da to 100 Da, 15 Da to 150 Da, 15 Da to 200 Da, 15 Da to 300 Da, or 15 Da to 500 Da. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, Si, F, Cl, Br, or I; provided that the substituent includes one C, N, O, S, Si, F, Cl, Br, or I atom. Examples of substituents include, but are not limited to, alkyl, alkenyl, alkynyl, heteroalkyl, heteroalkenyl, heteroalkynyl, aryl, heteroaryl, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, amino, etc.

For convenience, the term "molecular weight" is used with respect to a moiety or part of a molecule to indicate the sum of the atomic masses of the atoms in the moiety or part of a molecule, even though it may not be a complete molecule.

The structures associated with some of the chemical names referred to herein are depicted below. These structures may be unsubstituted, as shown below, or a substituent may independently be in any position normally occupied by a hydrogen atom when the structure is unsubstituted. Unless a point of attachment is indicated by —|, attachment may occur at any position normally occupied by a hydrogen atom.

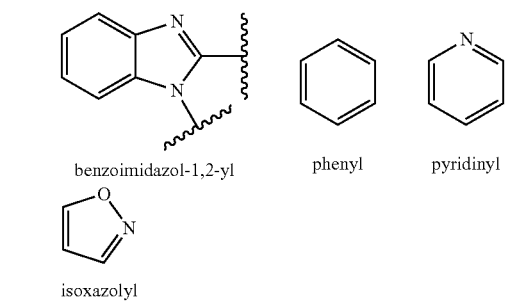

benzoimidazol-1,2-yl    phenyl    pyridinyl isoxazolyl

As used herein, the term "alkyl" has the broadest meaning generally understood in the art and may include a moiety composed of carbon and hydrogen containing no double or triple bonds. Alkyl may be linear alkyl, branched alkyl, cycloalkyl, or a combination thereof and in some embodiments, may contain from one to thirty-five carbon atoms. In some embodiments, alkyl may include $C_{1-10}$ linear alkyl, such as methyl (—$CH_3$), methylene (—$CH_2$—), ethyl (—$CH_2CH_3$), ethylene (—$C_2H_4$—), propylene (—$C_3H_6$—), n-butyl (—$CH_2CH_2CH_2CH_3$), n-pentyl (—$CH_2CH_2CH_2CH_2CH_3$), n-hexyl (—$CH_2CH_2CH_2CH_2CH_2CH_3$), etc.; $C_{3-10}$ branched alkyl, such as $C_3H_7$ (e.g. isopropyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.) $C_6H_{11}$ (e.g. cyclohexyl isomers), $C_7H_{13}$ (e.g. cycloheptyl isomers), etc.; and the like.

As used herein, the term "carbocyclyl" has the broadest meaning generally understood in the art and includes rings free of heteroatoms, such as cycloalkyl, e.g. cyclopropyl, cyclobutyl, cyclopentyl, cyclohexyl, etc.; cycloalkenyl, e.g. cyclopropenyl, cyclobutenyl, cyclopentenyl, cyclohexenyl; cycloalkynyl, e.g. cyclopropynyl, cyclobutynyl, cyclopentynyl, cyclohexynyl; as well as aryl rings free of heteroatoms.

As used herein the term "aryl" has the broadest meaning generally understood in the art and may include an aromatic ring or aromatic ring system such as phenyl, naphthyl, etc.

The term "heterocyclyl" includes any ring or ring system containing a heteroatom such as N, O, S, P, etc. Heterocyclyl includes heteroaryl rings or ring systems (such as those listed below) and non-aromatic rings or ring systems. Examples of non-aromatic heterocyclyl include azetidinyl, oxatanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxalanyl, dithiolanyl, tetrahydropyranyl, piperidinyl, piperazinyl, morpholino, etc.

The term "heteroaryl" also has the meaning understood by a person of ordinary skill in the art and includes an "aryl" which has one or more heteroatoms in the ring or ring system, such as pyridinyl, furyl, thienyl, oxazolyl, thiazolyl, imidazolyl, triazolyl, oxadiazolyl, isoxazolyl, indolyl, quinolinyl, benzofuranyl, benzothienyl, benzooxazolyl, benzothiazolyl, benzoimidazolyl, etc.

Unless otherwise indicated, any reference to a compound herein by structure, name, or any other means includes pharmaceutically acceptable salts, such as HCl, HBr, HI, $H_2SO_4$, acetate, citrate, sodium, potassium, and ammonium salts; prodrugs, such as ester prodrugs; alternate solid forms, such as polymorphs, solvates, hydrates, etc.; tautomers; or any other chemical species that may rapidly convert to a compound described herein under conditions in which the compounds are used as described.

If stereochemistry is not indicated, a name or structural representation includes any stereoisomer or any mixture of stereoisomers.

With respect to Formula 1, Bz can be optionally substituted benzoimidazol-1,2-yl. If the benzoimidazol-1,2-yl is substituted, it may have 1, 2, 3, or 4 substituents. Any substituent may be included on the benzoimidazol-1,2-yl. In some embodiments, some or all of the substituents on the benzoimidazol-1,2-yl may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. In some embodiments, some or all of the substituents may each have a molecular weight of 15 Da to 200 Da, 15 Da to 100 Da, or 15 Da to 50 Da, and consist of 2 to 5 chemical elements, wherein the chemical elements are independently C, H, O, N, S, F, Cl, or Br. In some embodiments, Bz can be optionally substituted benzoimidazol-1,2-diyl. In some embodiments, Bz can be optionally substituted benzoimidazol-1, 2, 6-triyl.

For example, with respect to Formula 1, the substituents of Bz may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy such as $OCH_3$, $OC_2H_5$, $OC_3H_7$, cyclic $OC_3H_5$, $OC_4H_9$, cyclic $OC_4H_7$, $OC_5H_{11}$, cyclic $OC_5H_9$, $OC_6H_{13}$, cyclic $OC_6H_{11}$, etc.; halo, such as F, Cl, Br, I; OH; CN; $NO_2$; $C_{1-6}$ fluoroalkyl, such as $CF_3$, $CF_2H$, $C_2F_5$, etc.; $C_{1-6}$ fluoroalkoxy, such as $OCF_3$, $OCF_2H$, $OC_2F_5$, etc.; a $C_{1-10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1-10}$ ketone such as $-COCH_3$, $-COC_2H_5$, $-COC_3H_7$, $-CO$-phenyl, etc.; or a $C_{1-10}$ amine such as $NH_2$, $NH(CH_3)$, $N(CH_3)_2$, $N(CH_3)C_2H_5$, etc. In some embodiments, a substituent of Bz may be F, Cl, Br, I, CN, $NO_2$, $C_{1-4}$ alkyl, $C_{1-4}$ alkyl-OH, $C_{1-3}$ O-alkyl, $CF_3$, COH, $C_{1-4}$ CO-alkyl, $CO_2H$, $C_{1-4}$ $CO_2$-alkyl, $NH_2$, or $C_{1-4}$ alkylamino.

Some embodiments include a compound represented by Formula 2:

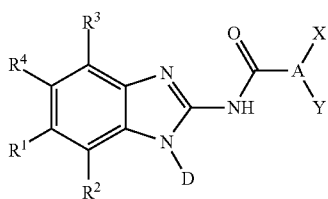

Formula 2

With respect to any relevant structural representation, such as Formula 1 or 2, D is optionally substituted $C_{3-6}$ carbocyclyl or $C_{2-5}$ heterocyclyl. If D is substituted cyclobutyl, it may have 1, 2, 3, 4, 5, 6, or 7 substituents. If D is substituted phenyl, it may have 1, 2, 3, 4, or 5 substituents. If D is substituted isoxazolyl, it may have 1 or 2. D may include any substituent. In some embodiments, some or all of the substituents of D may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. In some embodiments, some or all of the substituents may each have a molecular weight of 15 Da to 200 Da, 15 Da to 100 Da, or 15 Da to 50 Da, and consist of 2 to 5 chemical elements, wherein the chemical elements are independently C, H, O, N, S, F, Cl, or Br.

For example, with respect to any relevant structural representation, such as Formula 1 or 2, the substituents of D may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy such as $OCH_3$, $OC_2H_5$, $OC_3H_7$, cyclic $OC_3H_5$, $OC_4H_9$, cyclic $OC_4H_7$, $OC_5H_{11}$, cyclic $OC_5H_9$, $OC_6H_{13}$, cyclic $OC_6H_{11}$, etc.; halo, such as F, Cl, Br, I; OH; CN; $NO_2$; $C_{1-6}$ fluoroalkyl, such as $CF_3$, $CF_2H$, $C_2F_5$, etc.; $C_{1-6}$ fluoroalkoxy, such as $OCF_3$, $OCF_2H$, $OC_2F_5$, etc.; a $C_{1-10}$ ester such as $-O_2CCH_3$, $-CO_2CH_3$, $-O_2CC_2H_5$, $-CO_2C_2H_5$, $-O_2C$-phenyl, $-CO_2$-phenyl, etc.; a $C_{1-10}$ ketone such as $-COCH_3$, $-COC_2H_5$, $-COC_3H_7$, $-CO$-phenyl, etc.; or a $C_{1-10}$ amine such as $NH_2$, $NH(CH_3)$, $N(CH_3)_2$, $N(CH_3)C_2H_5$, etc. In some embodiments, a substituent of D may be F, Cl, Br, I, CN, $NO_2$, $C_{1-4}$ alkyl, $C_{1-4}$ alkyl-OH, $C_{1-3}$ O-alkyl, $CF_3$, COH, $C_{1-4}$ CO-alkyl, $CO_2H$, $C_{1-4}$ $CO_2$-alkyl, $NH_2$, or $C_{1-4}$ alkylamino.

With respect to any relevant structural representation, such as Formula 1 or 2, in some embodiments, D is:

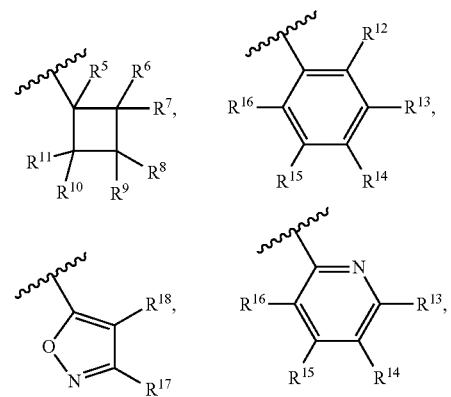

or optionally substituted $C_{2-4}$ alkyl.

With respect to any relevant structural representation, such as Formula 1 or 2, in some embodiments, D is optionally substituted cyclobutyl, optionally substituted phenyl, optionally substituted isoxazolyl, or isopropyl.

With respect to any relevant structural representation, such as Formula 1 or 2, in some embodiments, D is optionally substituted cyclobutyl. In some embodiments, D is cyclobutyl. In some embodiments, D is

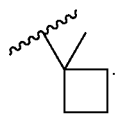

With respect to any relevant structural representation, such as Formula 1 or 2, in some embodiments, D is isopropyl.

With respect to any relevant structural representation, such as Formula 1 or 2, in some embodiments, D is t-butyl, or tert-butyl.

With respect to any relevant structural representation, such as Formula 1 or 2, in some embodiments, D is optionally substituted phenyl. In some embodiments D is

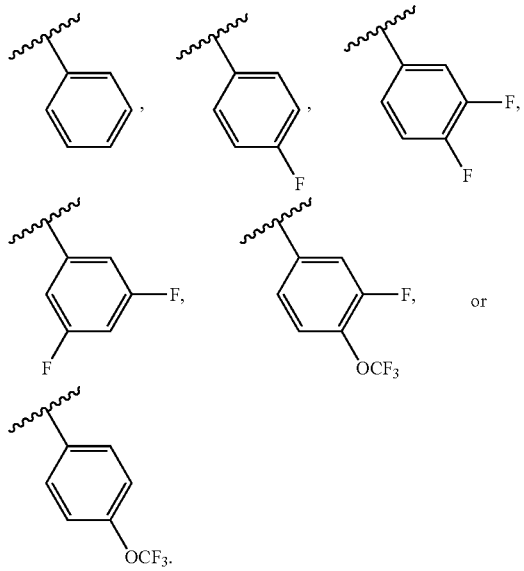

With respect to any relevant structural representation, such as Formula 1 or 2, in some embodiments, D is optionally substituted pyridinyl, such as optionally substituted pyridiny-2-yl, pyridin-3-yl, or pyridin-4-yl. In some embodiments, D is

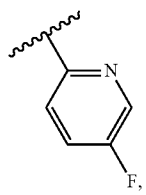

With respect to any relevant structural representation, such as Formula 1 or 2, in some embodiments, D is optionally substituted isoxazolyl. In some embodiments, D is

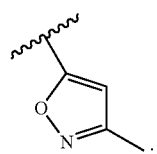 [SMILES: *c1cc(C)no1]

With respect to any relevant structural representation, such as Formula 1 or 2, A is $C_{2-8}$ alkyl, such as linear or branched

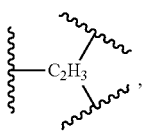

linear or branched

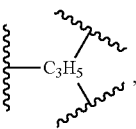

linear or branched

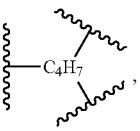

linear or branched

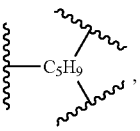

linear or branched

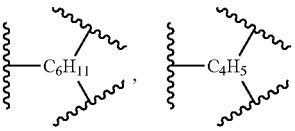

containing one ring,

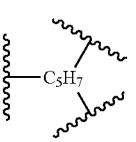

containing one ring,

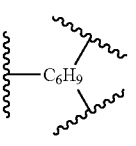

containing one ring,

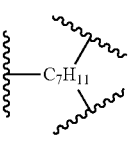

containing one ring, or

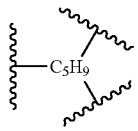

containing a bicyclic ring system.

With respect to any relevant structural representation, such as Formula 1 or 2, X is H, F, $CF_3$, optionally substituted phenyl, or optionally substituted pyridinyl. In some embodiments, X is H. In some embodiments, X is F. In some embodiments, X is $CF_3$.

With respect to any relevant structural representation, such as Formula 1 or 2, if X is substituted phenyl, it may have 1, 2, 3, 4, or 5, substituents. If X is substituted pyridinyl, it may have 1, 2, 3, or 4 substituents. In some embodiments, some or all of the substituents of X may have: from 0 to 10 carbon atoms and from 0 to 10 heteroatoms, wherein each heteroatom is independently: O, N, S, F, Cl, Br, or I (provided that there is at least 1 non-hydrogen atom); and/or a molecular weight of 15 g/mol to 500 g/mol. In some embodiments, some or all of the substituents may each have a molecular weight of 15 Da to 200 Da, 15 Da to 100 Da, or 15 Da to 50 Da, and consist of 2 to 5 chemical elements, wherein the chemical elements are independently C, H, O, N, S, F, Cl, or Br.

For example, with respect to any relevant structural representation, such as Formula 1 or 2, the substituents of X may be $C_{1-10}$ optionally substituted alkyl, such as $CH_3$, $C_2H_5$, $C_3H_7$, cyclic $C_3H_5$, $C_4H_9$, cyclic $C_4H_7$, $C_5H_{11}$, cyclic $C_5H_9$, $C_6H_{13}$, cyclic $C_6H_{11}$, etc., which may be optionally substituted; $C_{1-10}$ optionally substituted alkoxy such as $OCH_3$, $OC_2H_5$, $OC_3H_7$, cyclic $OC_3H_5$, $OC_4H_9$, cyclic $OC_4H_7$, $OC_5H_{11}$, cyclic $OC_5H_9$, $OC_6H_{13}$, cyclic $OC_6H_{11}$, etc.; halo, such as F, Cl, Br, I; OH; CN; $NO_2$; $C_{1-6}$ fluoroalkyl, such as $CF_3$, $CF_2H$, $C_2F_5$, etc.; $C_{1-6}$ fluoroalkoxy, such as $OCF_3$, $OCF_2H$, $OC_2F_5$, etc.; a $C_{1-10}$ ester such as —$O_2CCH_3$, —$CO_2CH_3$, —$O_2CC_2H_5$, —$CO_2C_2H_5$, —$O_2C$-phenyl, —$CO_2$—phenyl, etc.; a $C_{1-10}$ ketone such as —$COCH_3$, —$COC_2H_5$, —$COC_3H_7$, —CO-phenyl, etc.; or a $C_{1-10}$ amine such as $NH_2$, $NH(CH_3)$, $N(CH_3)_2$, $N(CH_3)C_2H_5$, etc. In some embodiments, a substituent of X may be F, Cl, Br, I, CN, $NO_2$, $C_{1-4}$ alkyl, $C_{1-4}$ alkyl-OH, $C_{1-3}$ O-alkyl, $CF_3$, COH, $C_{1-4}$ CO-alkyl, $CO_2H$, $C_{1-4}$ $CO_2$-alkyl, $NH_2$, or $C_{1-4}$ alkylamino.

With respect to any relevant structural representation, such as Formula 1 or 2, Y is H, F, Cl, Br, I, or a moiety having a molecular weight of 15 Da to 300 Da and consisting of 2 to 5 chemical elements, wherein the chemical elements are independently C, H, O, N, S, F, Cl, or Br. In some embodiments, Y is H, F, Cl, Br, I, CN, —COH, $C_{1-6}$—CO-alkyl, $CF_3$, OH, $C_{1-5}$ O-alkyl, $C_{0-6}$ amino, or $C_{0-6}$ fluoroamino. In some embodiments, Y is H, F, $CF_3$, OH, $C_{1-5}$ O-alkyl, $C_{0-6}$ amino, or $C_{0-6}$ fluoroamino. In some embodiments, Y is H. In some embodiments, Y is OH. In some embodiments, Y is F. In some embodiments, Y is $CF_3$. In some embodiments, Y is $C_{1-3}$ O-alkyl, such as —$OCH_3$, $OC_2H_5$, $OC_3H_7$, etc. In some embodiments, Y is $C_{0-6}$ fluoroamino. In some embodiments, Y is optionally substituted tetrahydropyranyl, such as

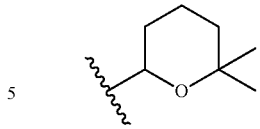

In some embodiments Y may include a $C_{1-8}$ alkyl that may include one or two $C_{3-6}$ carbocyclyl rings. In some embodiments, wherein Y includes at least one carbocyclyl rings, the rings may be connected to each other. In some embodiments, Y is —$C(CF_3)_2OH$ (or 1,1,1,3,3,3-hexafluoro-2-hydroxypropan-2-yl). In some embodiments Y is

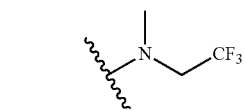

(or methyl(2,2,2-trifluoroethyl)amino). In some embodiments, Y is dimethylamino.

With respect to any relevant structural representation, such as Formula 1 or 2, in some embodiments

is $C_{2-8}$ alkyl, such as

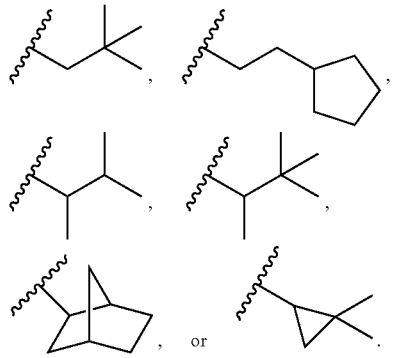

With respect to any relevant structural representation, such as Formula 1 or 2, in some embodiments

is $C_{2-8}$ hydroxyalkyl, such as

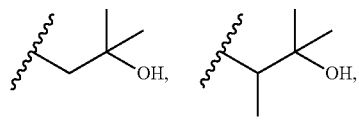

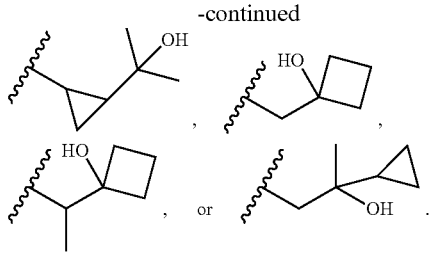

With respect to any relevant structural representation, such as Formula 1 or 2, in some embodiments

is $C_{2-8}$ fluoroalkyl such as

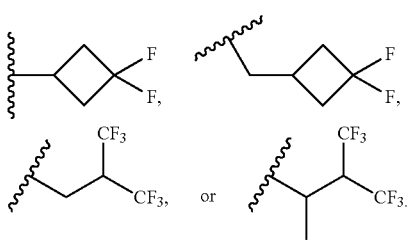

With respect to any relevant structural representation, such as Formula 1 or 2, in some embodiments

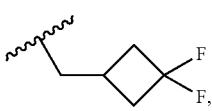

is $C_{2-8}$ alkoxyalkyl, such as

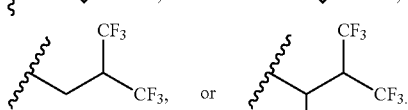

With respect to any relevant structural representation, such as Formula 1 or 2, in some embodiments

is $C_{2-8}$ hydroxyfluoroalkyl, such as

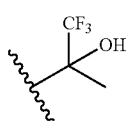

With respect to any relevant structural representation, such as Formula 1 or 2, in some embodiments

is optionally substituted 2-hydroxy-2-phenylethyl, such as

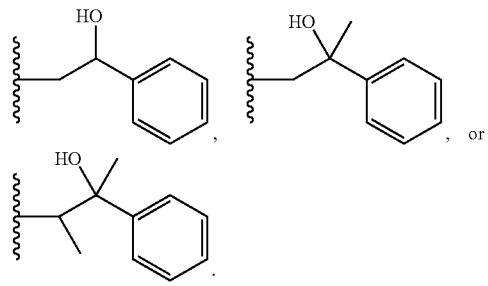

With respect to any relevant structural representation, such as Formula 1 or 2, in some embodiments

is optionally substituted 2-hydroxy-2-phenylpyridinyl, such as

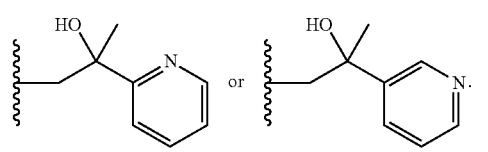 [SMILES: *CC(C)(O)c1ccccn1 ; *CC(C)(O)c1cccnc1]

With respect to any relevant structural representation, such as Formula 1 or 2, in some embodiments

is optionally substituted $C_{2-8}$ fluoroaminoalkyl, such as

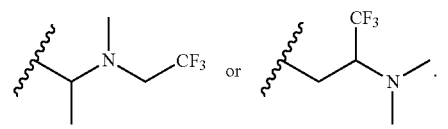

Generally $R^{1-18}$, may be H or any substituent, such as a substituent having 0 to 12 atoms or 0 to 6 carbon atoms and 0 to 5 heteroatoms, wherein each heteroatom is independently: O, N, S, F, Cl, Br, or I, and/or having a molecular weight of 15 g/mol to 300 g/mol. Any of $R^{1-18}$ may comprise: a) 1 or more alkyl moieties optionally substituted with, or optionally connected by or to, b) 1 or more functional groups, such as C═C, C≡C, CO, CO$_2$, CON, NCO$_2$, OH, SH, O, S, N, N═C, F, Cl, Br, I, CN, NO$_2$, CO$_2$H, NH$_2$, etc.; or may be a substituent having no alkyl portion, such as F, Cl, Br, I, NO$_2$, CN, NH$_2$, OH, COH, CO$_2$H, etc. In some embodiments, each of R$^{1-18}$ is independently H, F, Cl, Br, I, or a substituent having a molecular weight of 15 Da to 300 Da, 15 Da to 200 Da, 15 Da to 100 Da, or 15 Da to 60 Da, and consisting of 2 to 5 chemical elements, wherein the chemical elements are independently C, H, O, N, S, F, Cl, or Br.

With respect to any relevant structural representation, such as Formula 2, some non-limiting examples of R$^{1-18}$ may include R$^A$, F, Cl, Br, CN, OR$^A$, C$_{1-3}$ fluoroalkyl, C$_{1-4}$ hydroxyalkyl, NO$_2$, NR$^A$R$^B$, COR$^A$, CO$_2$R$^A$, OCOR$^A$, NR$^A$COR$^B$, CONR$^A$R$^B$, etc. In some embodiments, R$^{1-18}$ may be H; F; Cl; Br; CN; C$_{1-3}$ fluoroalkyl, such as CHF$_2$, CF$_3$, etc; OH; NH$_2$; C$_{1-6}$ alkyl, such as methyl, ethyl, propyl isomers (e.g. n-propyl and isopropyl), cyclopropyl, butyl isomers, cyclobutyl isomers (e.g. cyclobutyl and methylcyclopropyl), pentyl isomers, cyclopentyl isomers, hexyl isomers, cyclohexyl isomers, etc.; C$_{1-6}$ alkoxy, such as —O-methyl, —O-ethyl, isomers of —O-propyl, —O-cyclopropyl, isomers of —O-butyl, isomers of —O-cyclobutyl, isomers of —O-pentyl, isomers of —O-cyclopentyl, isomers of —O-hexyl, isomers of —O-cyclohexyl, etc.; C$_{1-4}$ hydroxyalkyl, such as —CH$_2$OH, —C$_2$H$_4$—OH, —C$_3$H$_6$—OH, C$_4$H$_8$—OH, etc.; C$_{2-5}$—CO$_2$-alkyl, such as —CO$_2$—CH$_3$, —CO$_2$—C$_2$H$_5$, —CO$_2$—C$_3$H$_7$, —CO$_2$—C$_4$H$_9$, etc.

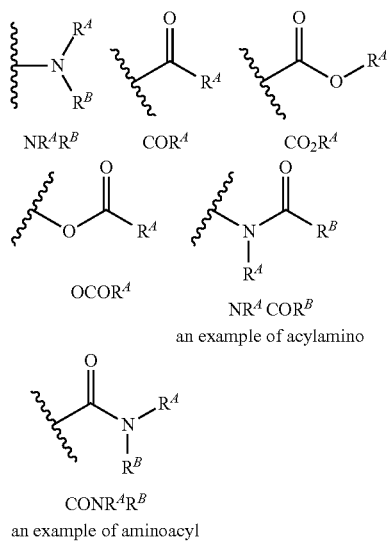

NR$^A$R$^B$      COR$^A$      CO$_2$R$^A$

OCOR$^A$

NR$^A$COR$^B$
an example of acylamino

CONR$^A$R$^B$
an example of aminoacyl

With respect to any relevant structural representation, each R$^A$ may independently be H, or C$_{1-12}$ alkyl, including: linear or branched alkyl having a formula C$_a$H$_{a+1}$, or cycloalkyl having a formula C$_a$H$_{a-1}$, wherein a is 1, 2, 3, 4, 5, 6, 7, 8, 9, 10, 11, or 12, such as linear or branched alkyl of a formula: CH$_3$, C$_2$H$_5$, C$_3$H$_7$, C$_4$H$_9$, C$_5$H$_{11}$, C$_6$H$_{13}$, C$_7$H$_{15}$, C$_8$H$_{17}$, C$_9$H$_{19}$, C$_{10}$H$_{21}$, etc., or cycloalkyl of a formula: C$_3$H$_5$, C$_4$H$_7$, C$_5$H$_9$, C$_6$H$_{11}$, C$_7$H$_{13}$, C$_8$H$_{15}$, C$_9$H$_{17}$, C$_{10}$H$_{19}$, etc. In some embodiments, R$^A$ may be H or C$_{1-6}$ alkyl. In some embodiments, R$^A$ may be H or C$_{1-3}$ alkyl. In some embodiments, R$^A$ may be H or CH$_3$. In some embodiments, R$^A$ may be H.

With respect to any relevant structural representation, each R$^B$ may independently be H, or C$_{1-12}$ alkyl, including: linear or branched alkyl having a formula C$_a$H$_{a+1}$, or cycloalkyl having a formula C$_a$H$_{a-1}$, wherein a is 1, 2, 3, 4, 5, 6, 7, 8, 9, 10, 11, or 12, such as linear or branched alkyl of a formula: CH$_3$, C$_2$H$_5$, C$_3$H$_7$, C$_4$H$_9$, C$_5$H$_{11}$, C$_6$H$_{13}$, C$_7$H$_{15}$, C$_8$H$_{17}$, C$_9$H$_{19}$, C$_{10}$H$_{21}$, etc., or cycloalkyl of a formula: C$_3$H$_5$, C$_4$H$_7$, C$_5$H$_9$, C$_6$H$_{11}$, C$_7$H$_{13}$, C$_8$H$_{15}$, C$_9$H$_{17}$, C$_{10}$H$_{19}$, etc. In some embodiments, R$^B$ may be H or C$_{1-3}$ alkyl. In some embodiments, R$^B$ may be H or CH$_3$. In some embodiments, R$^B$ may be H.

With respect to any relevant structural representation, such as Formula 2, in some embodiments R$^1$ is H, F, Cl, Br, CN, OCH$_3$, CHF$_2$, CF$_3$, C$_{1-4}$—CO$_2$-alkyl, C$_{1-4}$ alkyl, or C$_{1-4}$ hydroxyalkyl. In some embodiments, R$^1$ is H, Cl, Br, CN, OCH$_3$, CHF$_2$, CF$_3$, —CO$_2$CH$_2$CH$_3$, —CH$_2$OH,

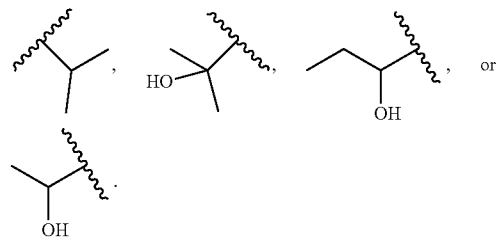

In some embodiments, R$^1$ is H. In some embodiments, R$^1$ is Cl. In some embodiments, R$^1$ is Br. In some embodiments, R$^1$ is CN. In some embodiments, R$^1$ is OCH$_3$. In some embodiments, R$^1$ is CHF$_2$. In some embodiments, R$^1$ is CF$_3$. In some embodiments, R$^1$ is —CO$_2$CH$_2$CH$_3$. In some embodiments, R$^1$ is —CH$_2$OH. In some embodiments, R$^1$ is

In some embodiments, R$^1$ is

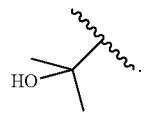

In some embodiments, R$^1$ is

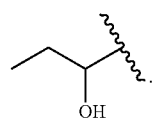

In some embodiments, R$^1$ is

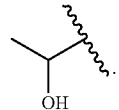

In some embodiments, $R^1$ is —$OCH_3$, —CN, —$CF_3$, —$CH_2OH$, —$COOCH_2CH_3$, —$C(CH_3)_2OH$, —$CHOHCH_2CH_3$, —$CHOHCH_3$, —$CHF_2$, —$CH(CH_3)_2$, —$C(CH_2CH_3)OH$, —$CH_2CO$ $OCH_2CH_3$, —$CH_2C(CH_3)_2OH$, —$CH_2COOH$, or —$CH_2CON(CH_3)_2$. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation, such as Formula 2, in some embodiments $R^2$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^2$ is H. In some embodiments, $R^2$ is $CH_2OH$. In some embodiments, $R^2$ is —$CO_2CH_3$. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl. In some embodiments, $R^2$ is —$CH_2OH$, —$CO_2Me$, or —$C(CH_3)_2OH$.

With respect to any relevant structural representation, such as Formula 2, in some embodiments $R^3$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^3$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation, such as Formula 2, in some embodiments $R^4$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^4$ is H. In some embodiments, $R^4$ is $CH_3$. In some embodiments, $R^4$ is $CF_3$. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation, such as Formula 2, in some embodiments $R^5$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^5$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation, such as Formula 2, in some embodiments $R^6$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^6$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation, such as Formula 2, in some embodiments $R^7$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^7$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation, such as Formula 2, in some embodiments $R^8$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^8$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation, such as Formula 2, in some embodiments $R^9$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^9$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation, such as Formula 2, in some embodiments $R^{10}$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^{10}$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation, such as Formula 2, in some embodiments $R^{11}$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^{11}$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation, such as Formula 2, in some embodiments $R^{12}$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^{12}$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation, such as Formula 2, in some embodiments $R^{13}$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^{13}$ is H. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

With respect to any relevant structural representation, such as Formula 2, in some embodiments $R^{14}$ is H, F, Cl, Br, CN, $OCH_3$, $CHF_2$, $CF_3$, $C_{1-4}$—$CO_2$-alkyl, $C_{1-4}$ alkyl, or $C_{1-4}$ hydroxyalkyl. In some embodiments, $R^{14}$ is H. In some embodiments, $R^{14}$ is F. With respect to the embodiments recited in this paragraph, in some embodiments, the remaining groups of $R^{1-18}$ may independently be $R^A$, F, Cl, Br, CN, $OR^A$, $C_{1-3}$ fluoroalkyl, $C_{1-4}$ hydroxyalkyl, $NO_2$, $NR^AR^B$, $COR^A$, $CO_2R^A$, OCORA, $NR^ACOR^B$, $CONR^AR^B$, etc. In some embodiments, the remaining groups of $R^{1-18}$ may be H, F, Cl, Br, CN, $C_{1-3}$ fluoroalkyl, OH, $NH_2$, $C_{1-6}$ alkyl, $C_{1-6}$ alkoxy, $C_{1-4}$—$CO_2$-alkyl, or $C_{1-4}$ hydroxyalkyl.

Some embodiments include:

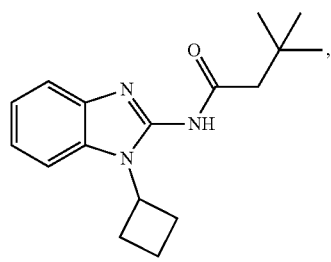

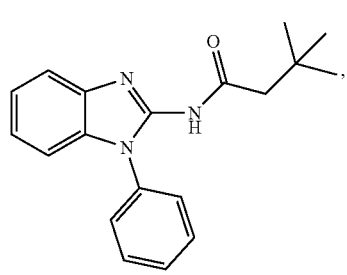

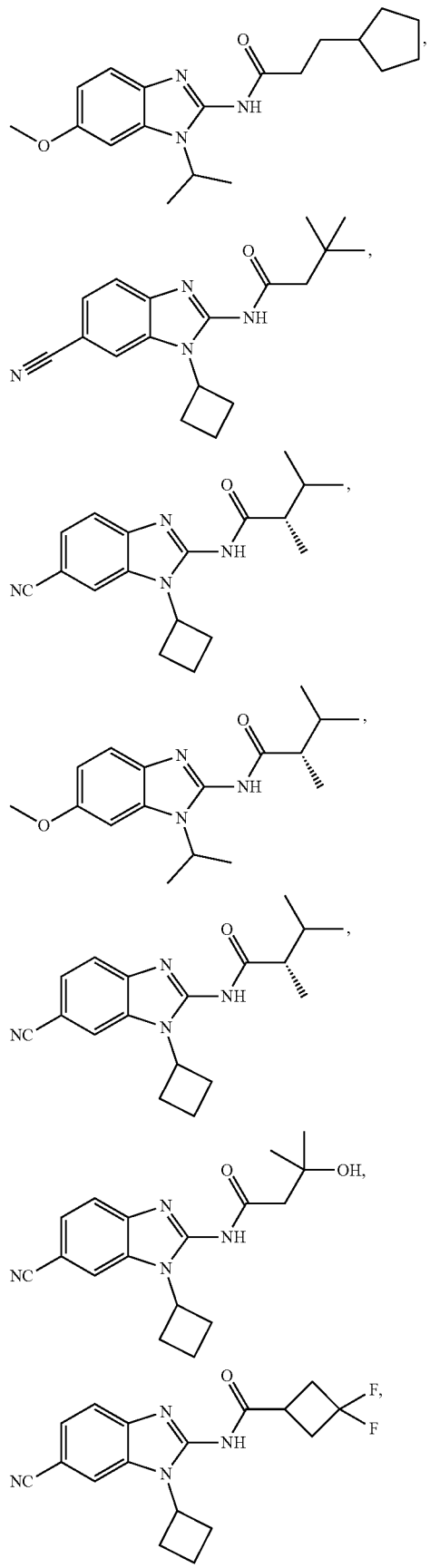

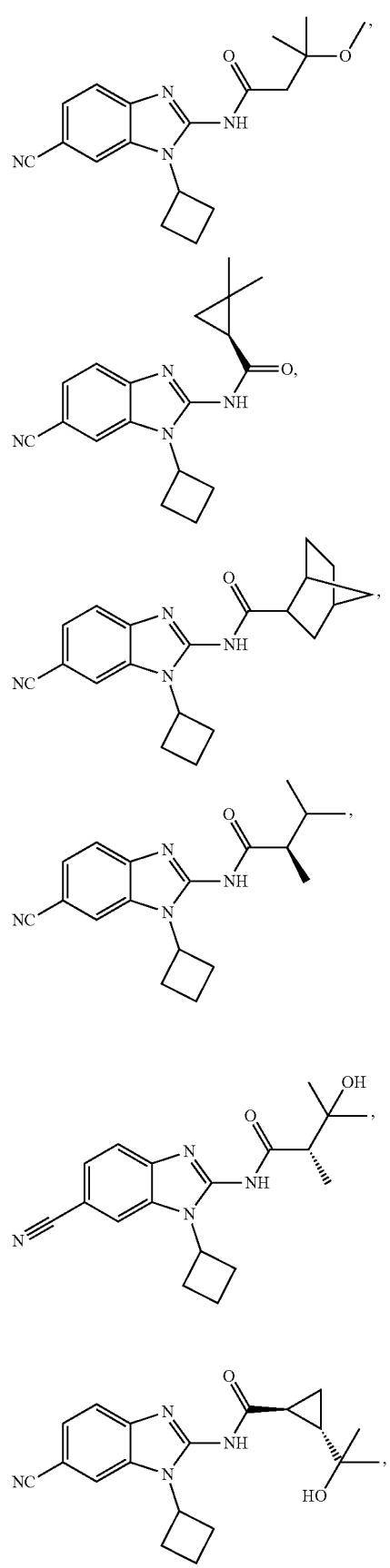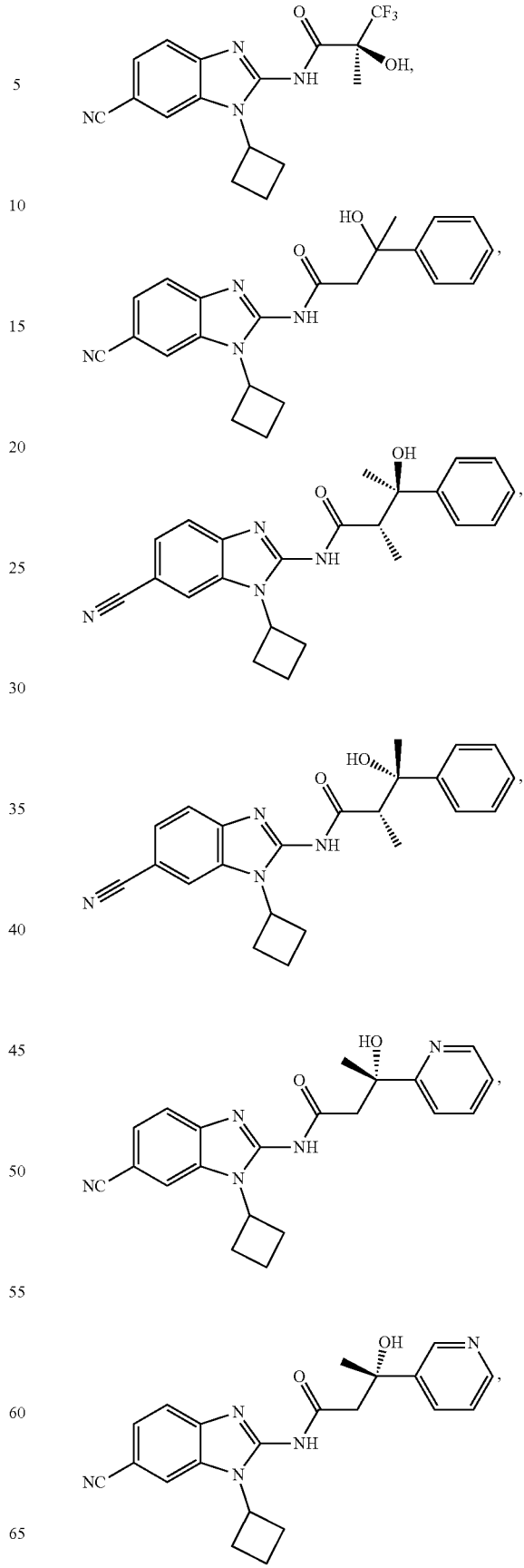

-continued
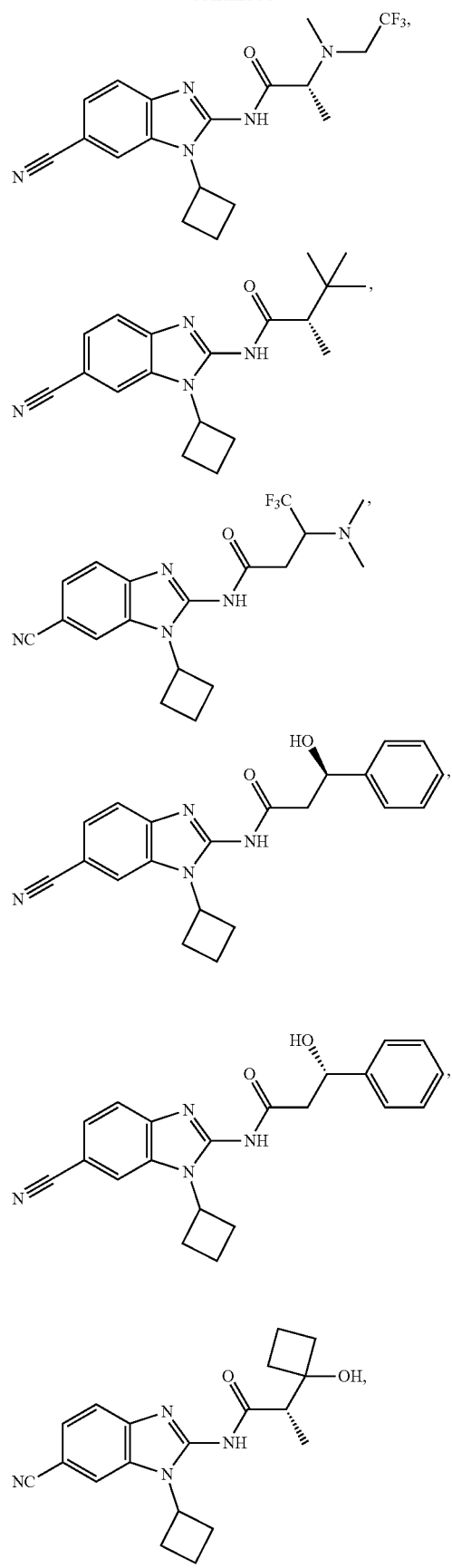
-continued
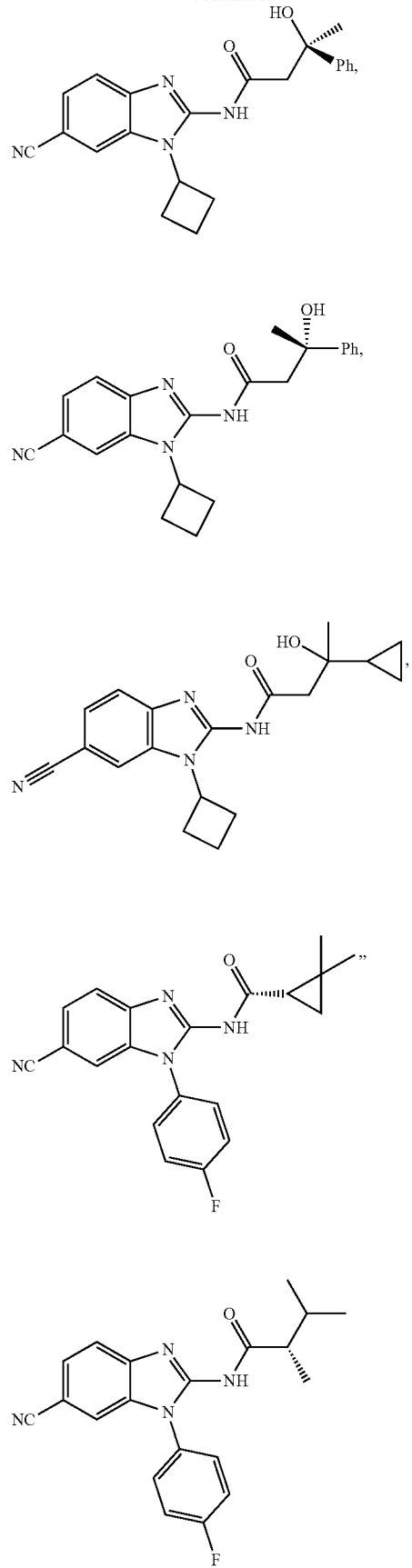

-continued
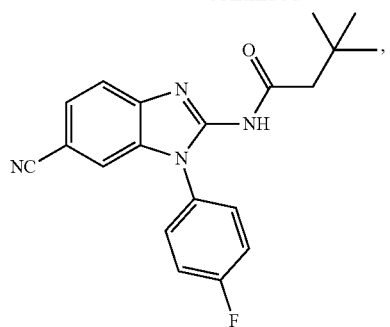
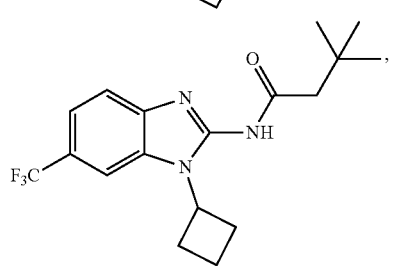
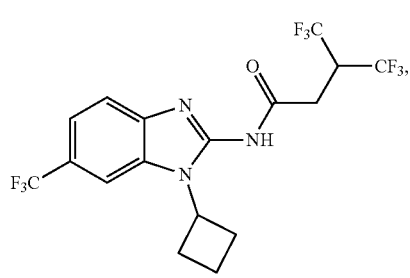
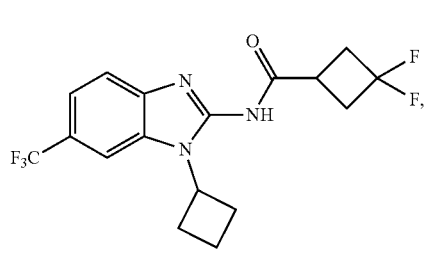
-continued
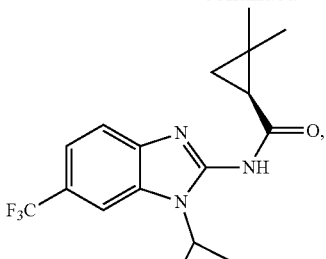
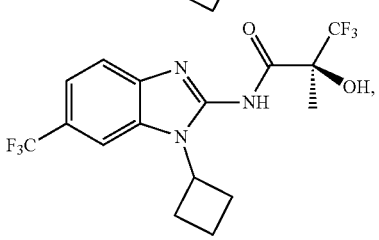
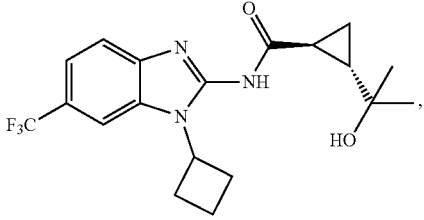
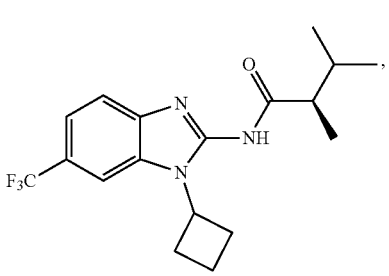
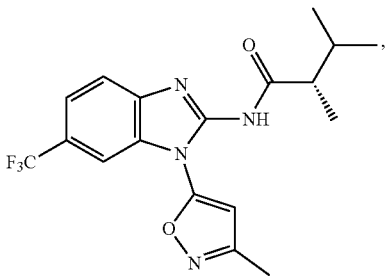
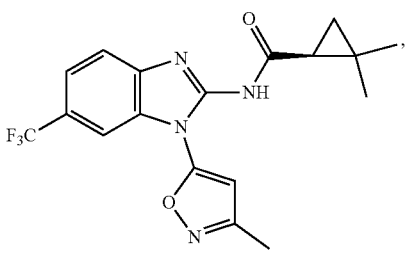

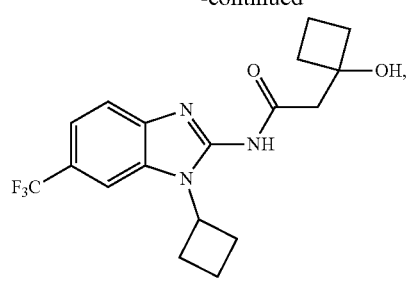
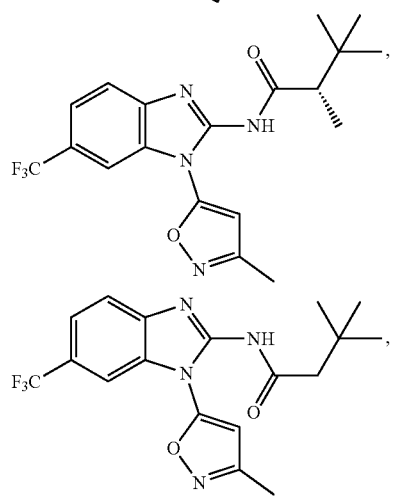
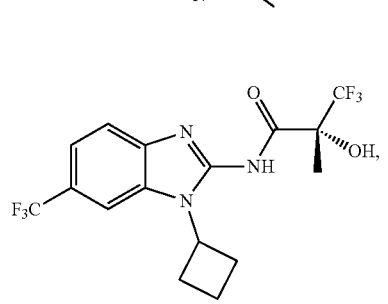
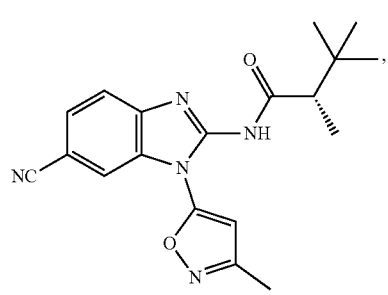
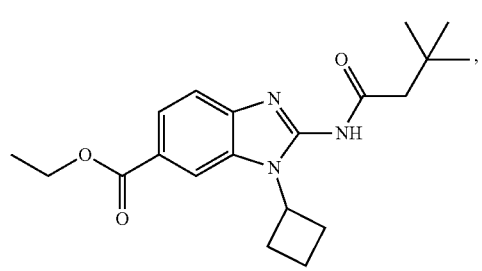
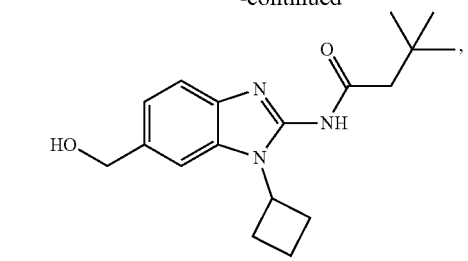
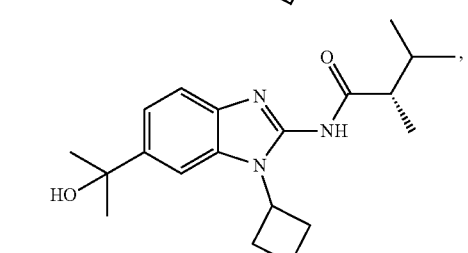
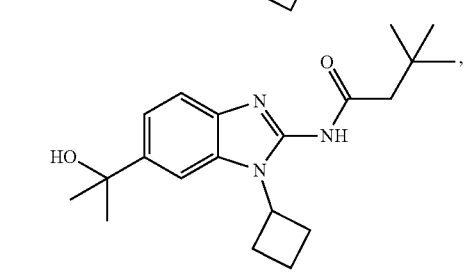
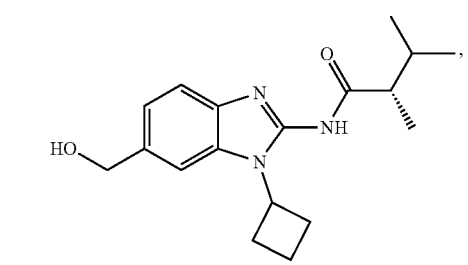
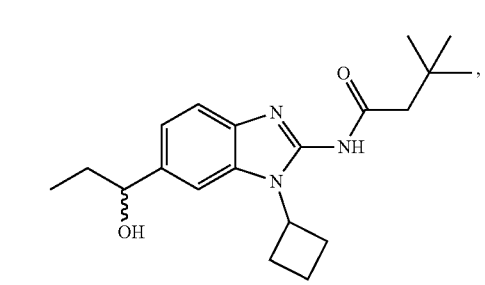
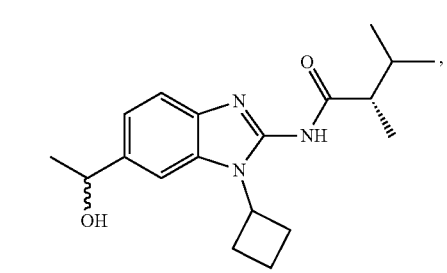

27
-continued
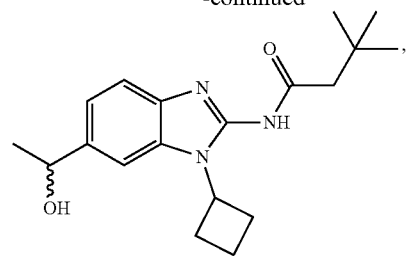
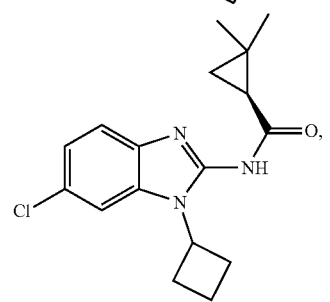
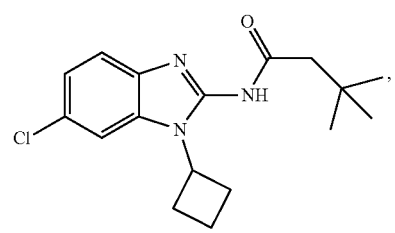
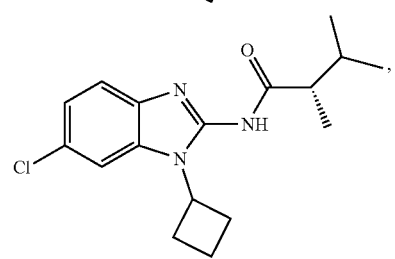
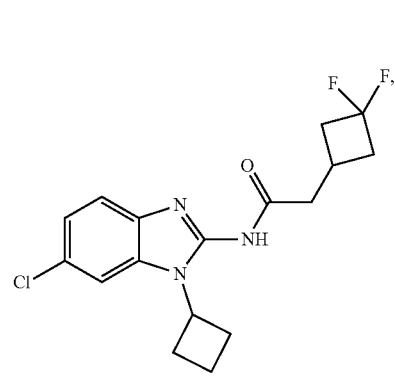
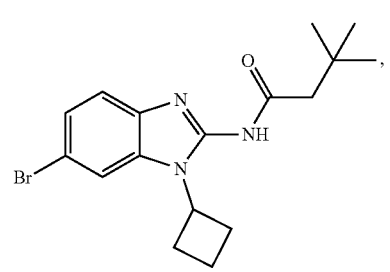
28
-continued
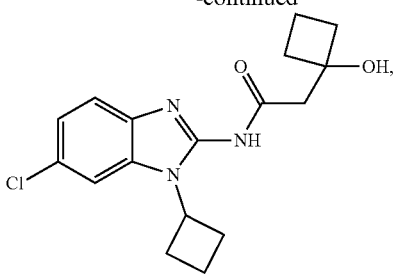
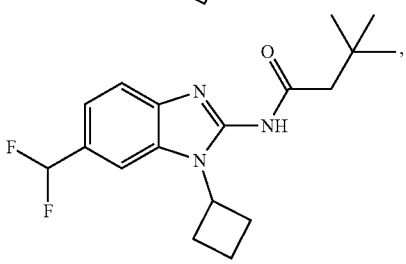
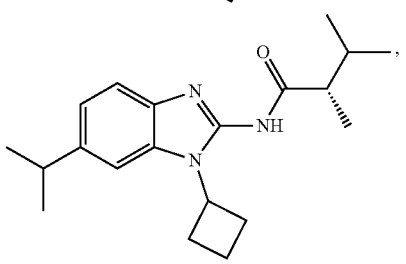
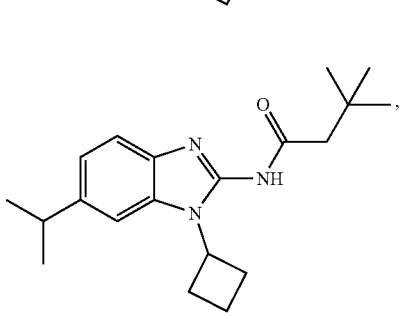
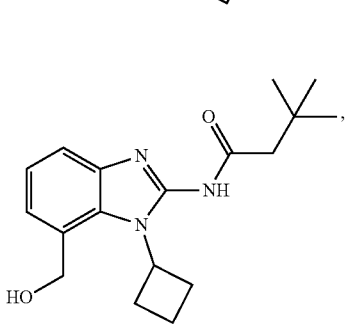
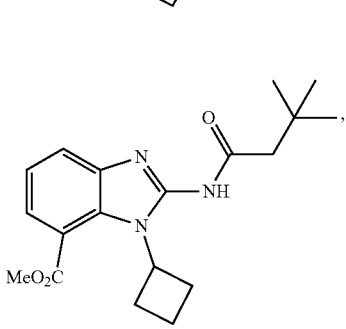

29
-continued
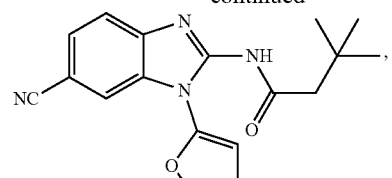
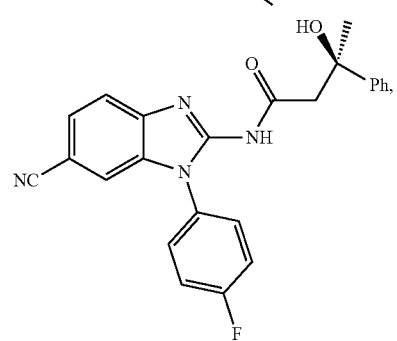
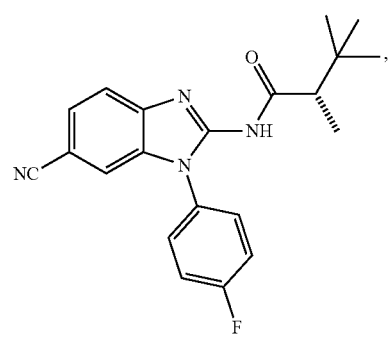
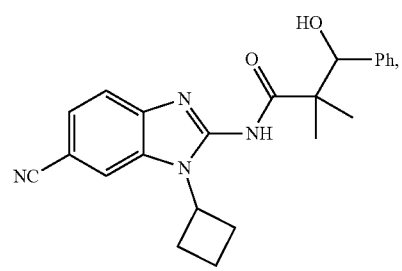
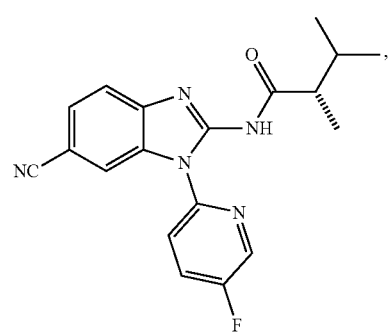
30
-continued
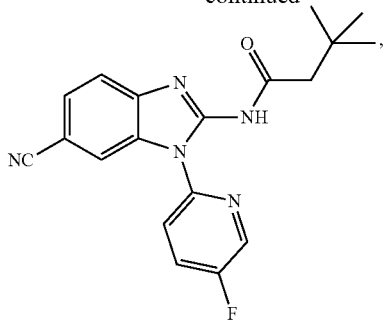
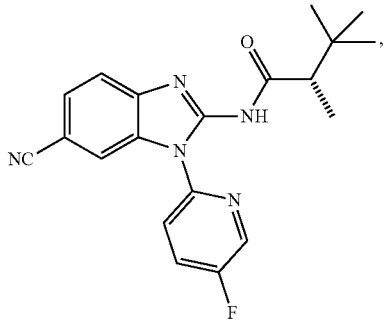
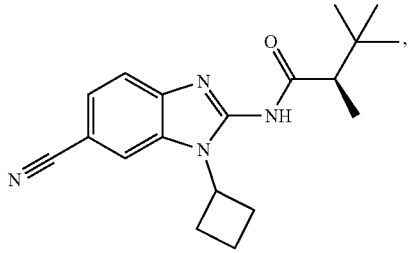
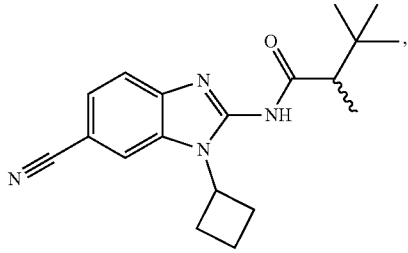
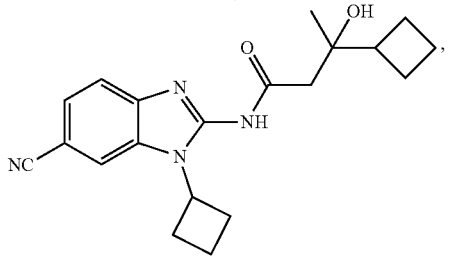
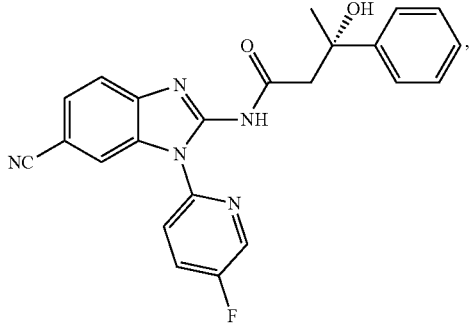

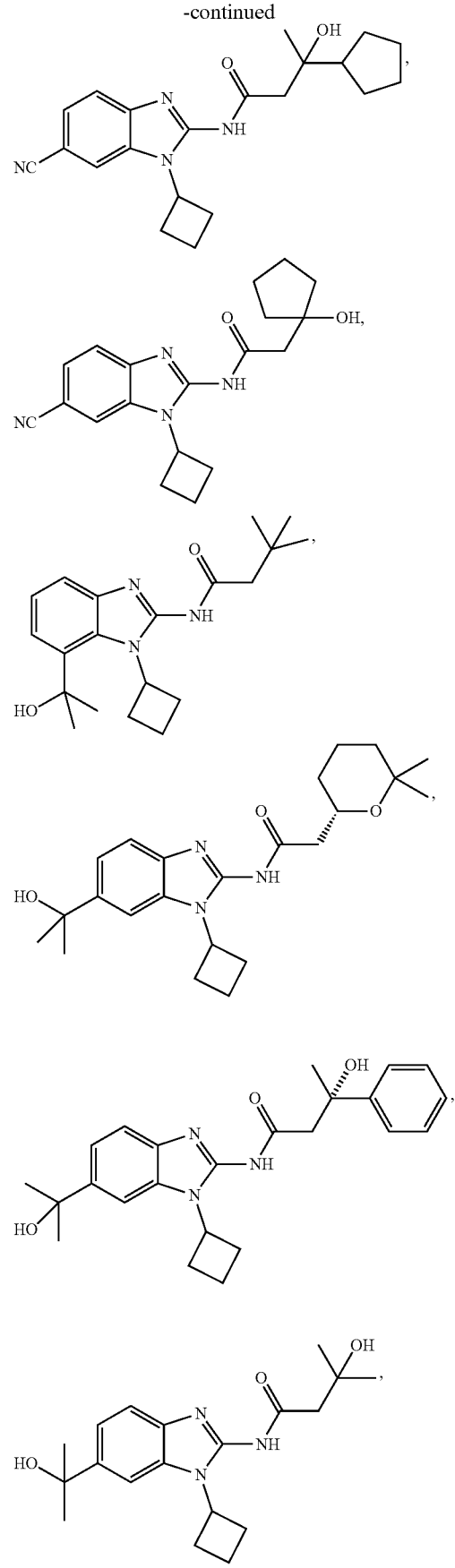
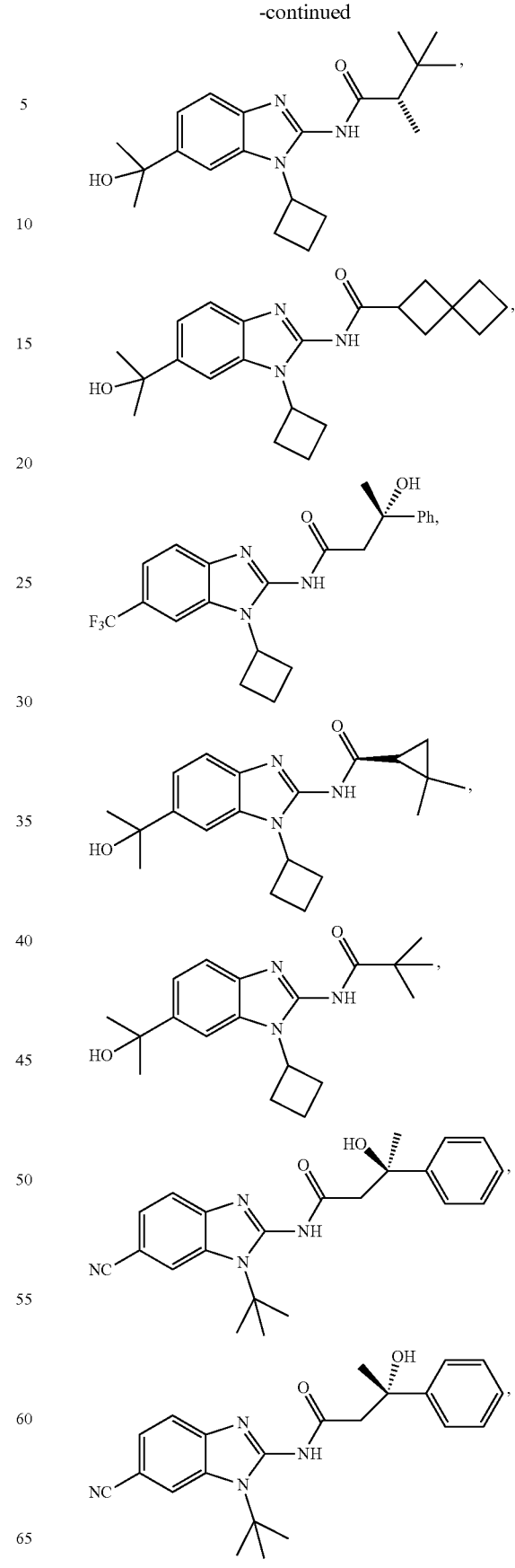

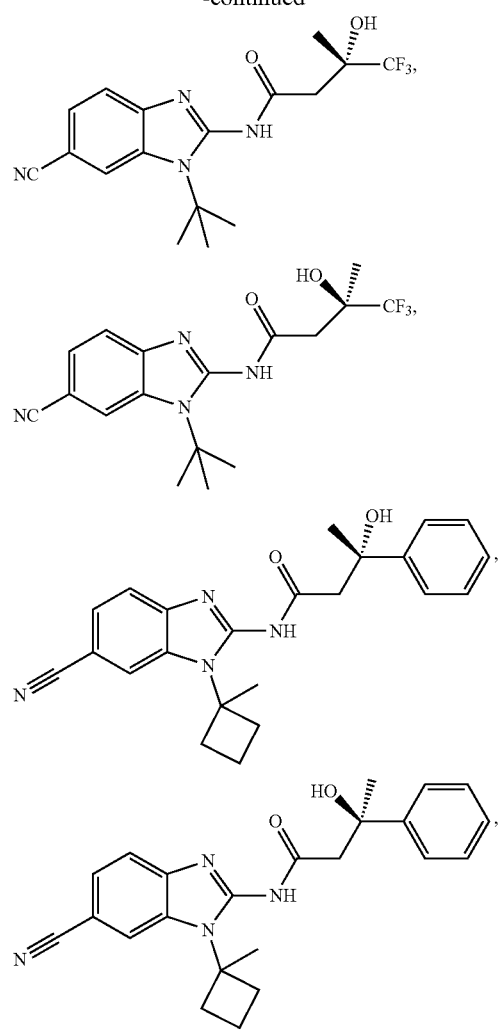
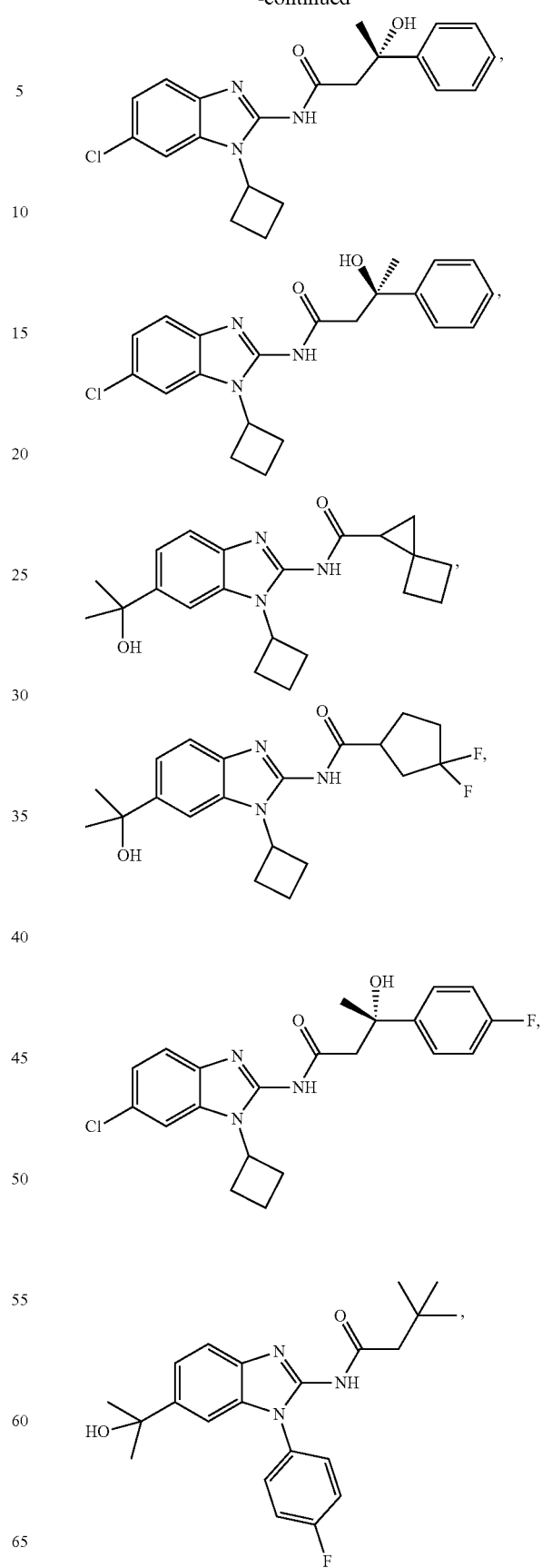

35
-continued
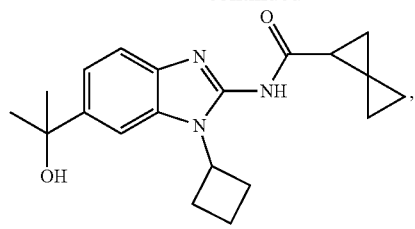
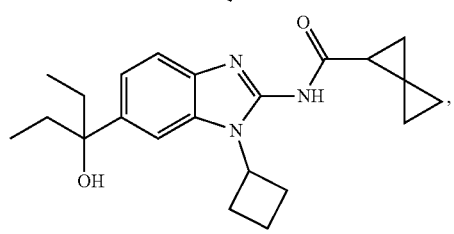
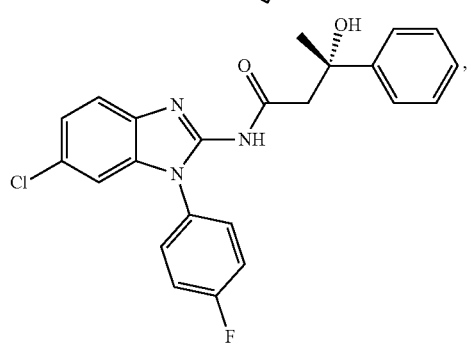
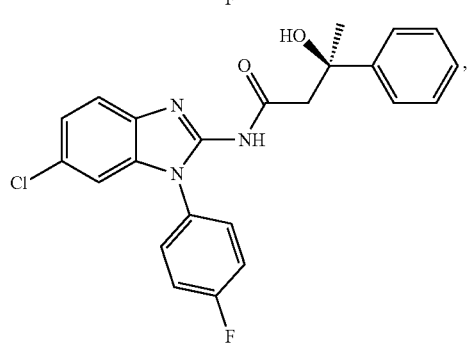
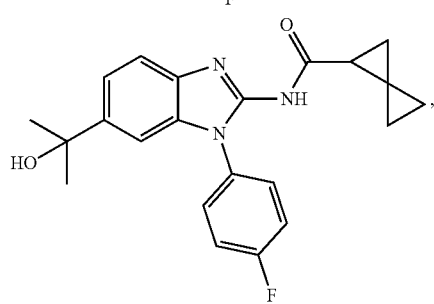
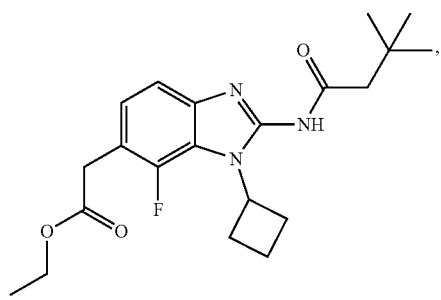
36
-continued
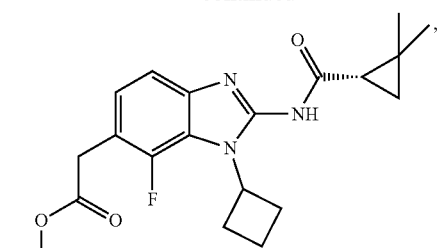
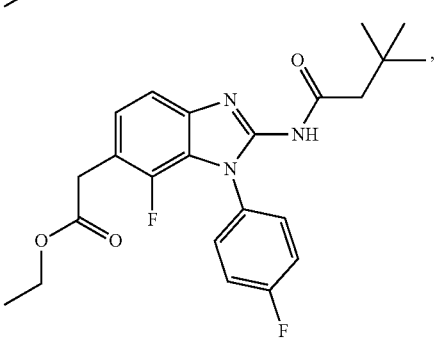
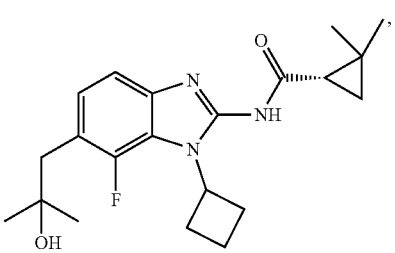
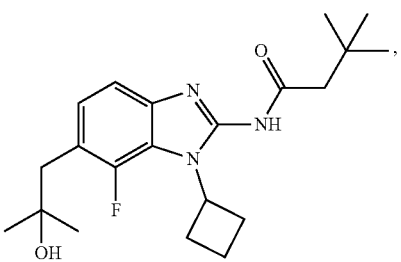
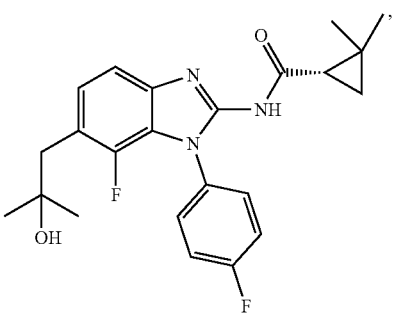

-continued
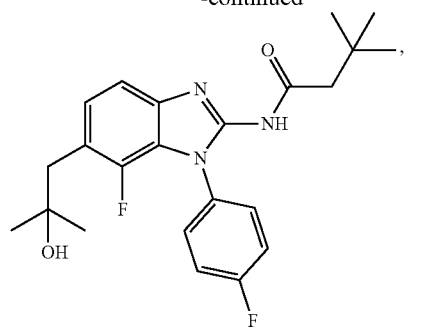
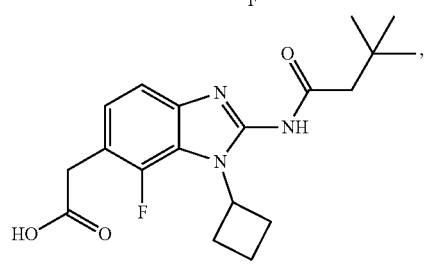
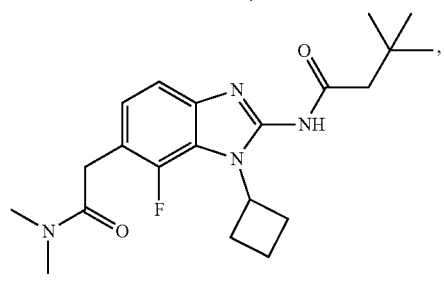
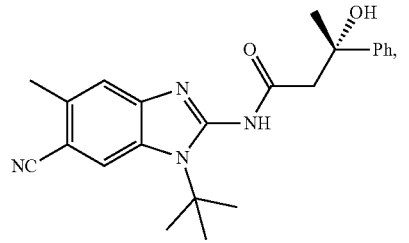
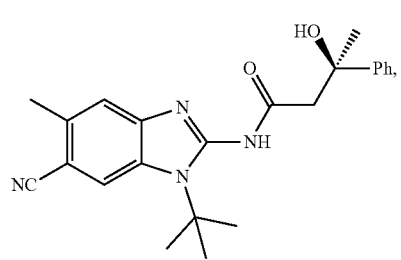
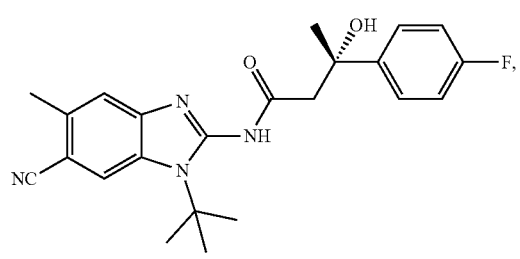
-continued
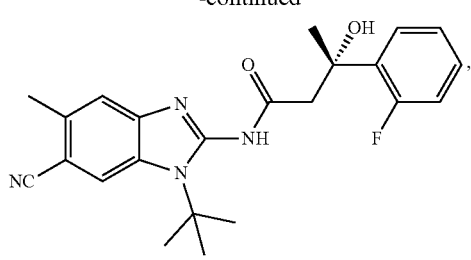
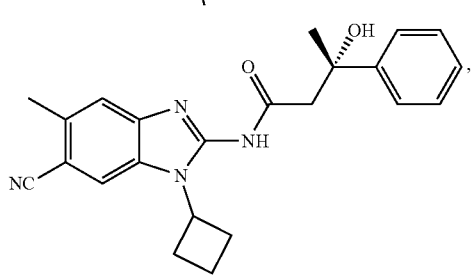
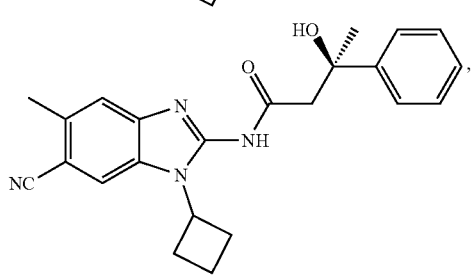
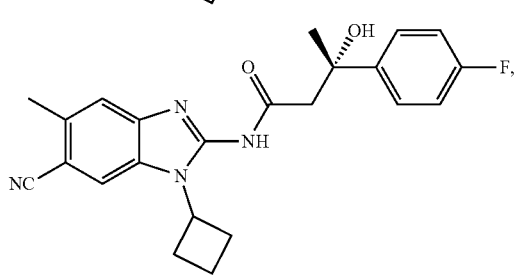
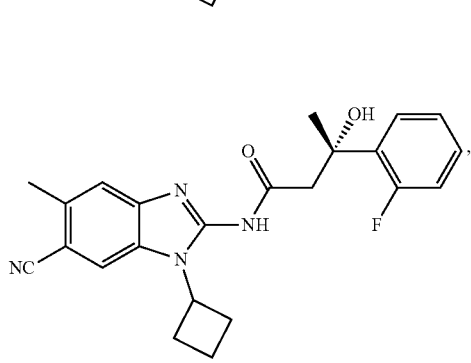
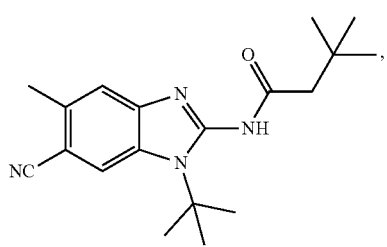

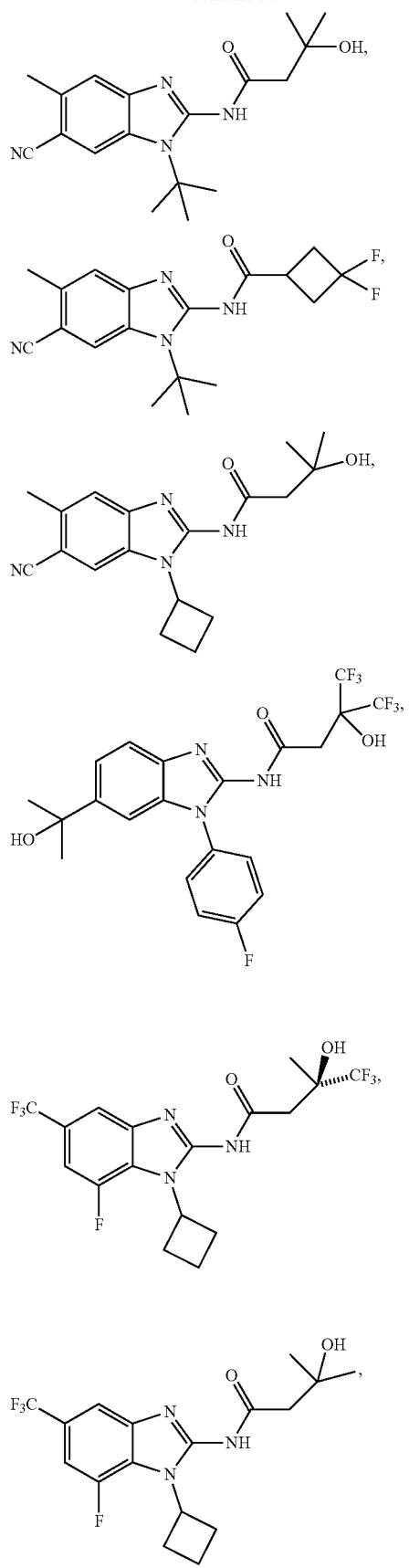
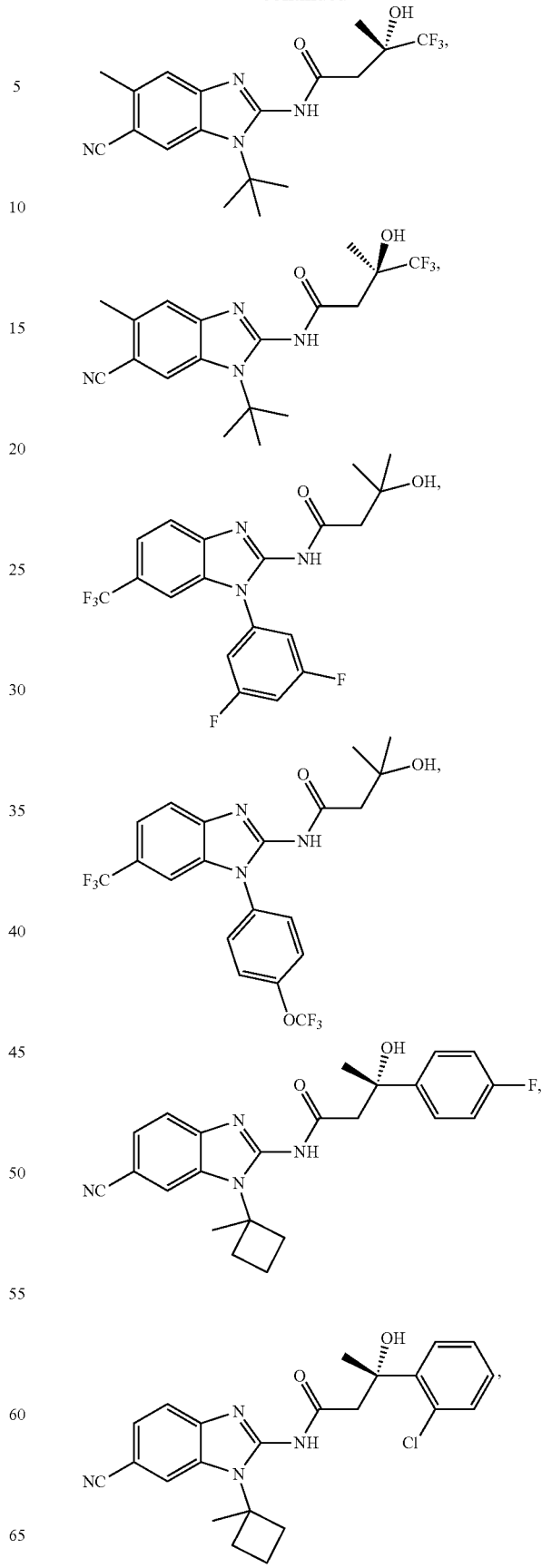

-continued

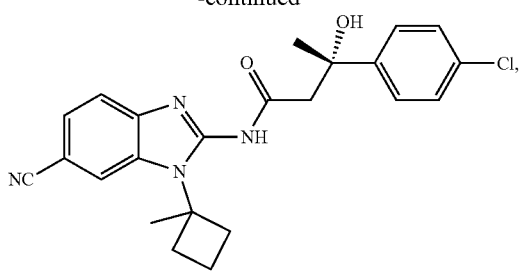

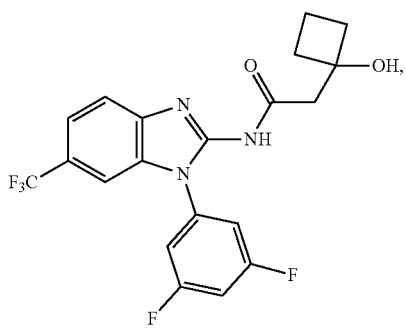

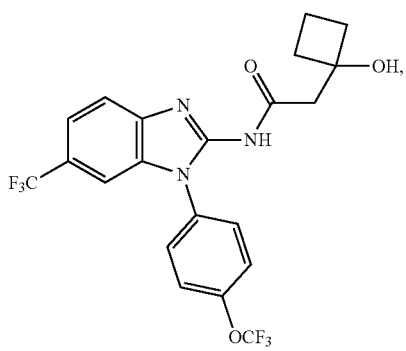

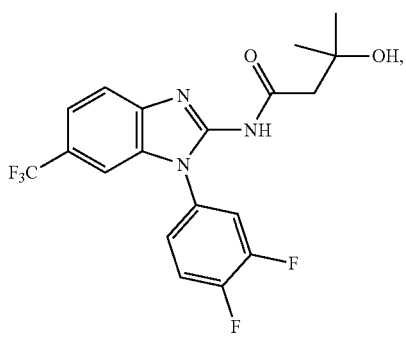

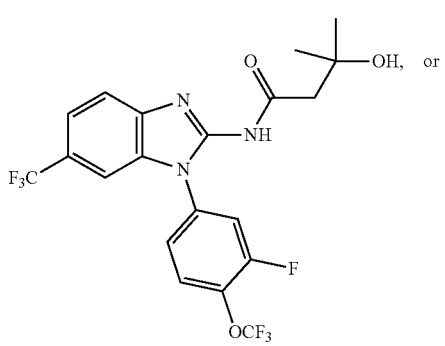 or

-continued

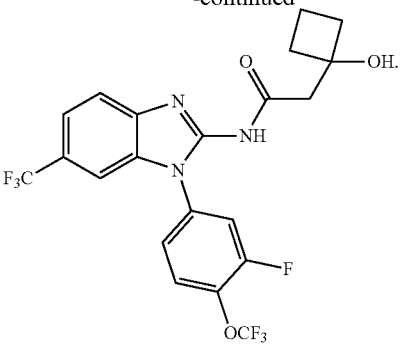

The compounds described herein, such as a compound of Formula 1 or Formula 2, (referred to hereafter as a "subject compound" or "subject compounds") can be used to treat a disorder associated with a Kv7 potassium channel activator. Treatment of a disorder includes diagnosis, cure, mitigation, treatment, or prevention of the disorder in man or other animals. In some embodiments, the disorder is epilepsy, pain, migraine, a disorder of neurotransmitter release, a smooth muscle contractility disorder, a dyskinesia, dystonia, mania, or a hearing disorder. In some embodiments, the disorder is epilepsy, neuropathic pain, inflammatory pain, persistent pain, cancer pain, postoperative pain, migraine, anxiety, substance abuse, schizophrenia, a bladder disorder, a vasculature disorder, a dyskinesia, dystonia, mania, a hearing disorder, or tinnitus.

Appropriate excipients for use in a pharmaceutical composition comprising a subject compound (referred to hereafter as "subject compositions" or a "subject composition") may include, for example, one or more carriers, binders, fillers, vehicles, disintegrants, surfactants, dispersion or suspension aids, thickening or emulsifying agents, isotonic agents, preservatives, lubricants, and the like or combinations thereof, as suited to a particular dosage from desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof.

A subject composition may be formulated for any desirable route of delivery including, but not limited to, parenteral, intravenous, intradermal, subcutaneous, oral, inhalative, transdermal, topical, transmucosal, rectal, interacisternal, intravaginal, intraperitoneal, buccal, and intraocular.

Parenteral, intradermal or subcutaneous formulations may be sterile injectable aqueous or oleaginous suspensions or solutions. Acceptable vehicles, solutions, suspensions and solvents may include, but are not limited to, water or other sterile diluent; saline; Ringer's solution; sodium chloride; fixed oils such as mono- or diglycerides; fatty acids such as oleic acid; polyethylene glycols; glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; and agents for the adjustment of tonicity such as sodium chloride or dextrose. The pH can be adjusted with acids or bases, such as hydrochloric acid or sodium hydroxide. A parenteral preparation may be enclosed in ampoules, disposable syringes or multiple dose vials made of glass or plastic.

Pharmaceutical compositions suitable for injectable use may include sterile aqueous solutions or dispersions and sterile powders for the extemporaneous preparation of sterile injectable solutions or dispersion. For intravenous administration, suitable carriers include, but are not limited to, saline, bacteriostatic water, CREMOPHOR EL® (BASF, Parsippany, N.J.) or phosphate buffered saline (PBS). The solvent or dispersion medium may contain, for example, water, ethanol, polyol (for example, glycerol, propylene glycol, and liquid polyethylene glycol, and the like), and suitable mixtures thereof. Proper fluidity can be maintained, for example, by the use of a coating such as lecithin, by the maintenance of the required particle size in the case of dispersion and by the use of surfactants. Preventing growth of microorganisms can be achieved by various antibacterial and antifungal agents, for example, parabens, chlorobutanol, phenol, ascorbic acid, thimerosal, and the like. The composition may also include isotonic agents such as, for example, sugars; polyalcohols such as mannitol; sorbitol; or sodium chloride. Prolonged absorption of injectable compositions can be enhanced by addition of an agent that delays absorption, such as, for example, aluminum monostearate or gelatin.

Oral compositions may include an inert diluent or an edible carrier. They may be enclosed in gelatin capsules or compressed into tablets. Tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

In addition to oral or injected administration, systemic administration may be by transmucosal or transdermal means. For transmucosal or transdermal administration, penetrants may be used. Such penetrants are generally known in the art and include, for example, detergents, bile salts, and fusidic acid derivatives. Transdermal administration may include a bioactive agent and may be formulated into ointments, salves, gels, or creams as generally known in the art. Transmucosal administration may be accomplished through the use of nasal sprays or suppositories.

A subject compound may be administered in a therapeutically effective amount, according to an appropriate dosing regimen. As understood by a skilled artisan, an exact amount required may vary from subject to subject, depending on a subject's species, age and general condition, the severity of the infection, the particular agent(s) and the mode of administration. In some embodiments, about 0.001 mg/kg to about 50 mg/kg, of the pharmaceutical composition based on the subject's body weight is administered, one or more times a day, to obtain the desired therapeutic effect. In other embodiments, about 0.01 mg/kg to about 25 mg/kg, of the pharmaceutical composition based on the subject's body weight is administered, one or more times a day, to obtain the desired therapeutic effect.

A total daily dosage of a subject compound can be determined by the attending physician within the scope of sound medical judgment. A specific therapeutically effective dose level for any particular patient or subject will depend upon a variety of factors including the disorder being treated and the severity of the disorder; the activity of the specific compound employed; the specific composition employed; the age, body weight, general health, sex and diet of the patient or subject; the time of administration, route of administration, and rate of excretion of the specific compound employed; the duration of the treatment; drugs used in combination or coincidental with the specific compound employed; and other factors well known in the medical arts.

EMBODIMENTS SECTION

The following example embodiments are contemplated.
Embodiment 1. A compound represented by a formula:

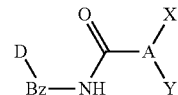

wherein D is optionally substituted $C_{3-6}$ carbocyclyl, optionally substituted $C_{2-5}$ heterocyclyl, isopropyl, or t-butyl;
Bz is optionally substituted benzoimidazol-1,2-diyl;
A is $C_{1-8}$ alkyl;
X is H, F, $CF_3$, optionally substituted phenyl, or optionally substituted pyridinyl; and
Y is H, F, Cl, Br, I, or a moiety having a molecular weight of 15 Da to 300 Da and consisting of 2 to 5 chemical elements, wherein the chemical elements are independently C, H, O, N, S, F, Cl, or Br.
Embodiment 2. The compound of embodiment 1, wherein each substituent of D, Bz, or X, if present, independently has a molecular weight of 15 Da to 200 Da and consists of 2 to 5 chemical elements, wherein the chemical elements are independently C, H, O, N, S, F, Cl, or Br.
Embodiment 3. The compound of embodiment 1 or 2, wherein Y is H, F, Cl, Br, I, CN, —COH, $C_{1-6}$—CO-alkyl, $CF_3$, OH, $C_{1-5}$ O-alkyl, $C_{0-6}$ amino, or $C_{0-6}$ fluoroamino.
Embodiment 4. The compound of embodiment 1, 2, or 3, further represented by a formula:

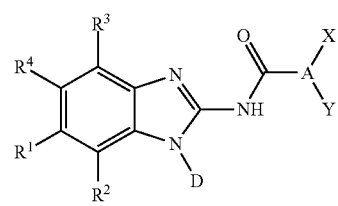

wherein $R^1$, $R^2$, $R^3$, and $R^4$ are independently H, F, Cl, Br, I, or a substituent having a molecular weight of 15 Da to 200 Da and consisting of 2 to 5 chemical elements, wherein the chemical elements are independently C, H, O, N, S, F, Cl, or Br.
Embodiment 5. The compound of embodiment 1, 2, 3, or 4, wherein Y is H, F, $CF_3$, OH, $C_{1-5}$ O-alkyl, $C_{0-6}$ alkylamino, optionally substituted tetrahydropyranyl, or $C_{0-6}$ fluoroalkylamino.
Embodiment 6. The compound of embodiment 4 or 5, wherein $R^1$ is H, Cl, Br, —$OCH_3$, —CN, —$CF_3$, —$CH_2OH$, —$COOCH_2CH_3$, —$C(CH_3)_2OH$, —$CHOHCH_2CH_3$, —$CHOHCH_3$, —$CHF_2$, —$CH(CH_3)_2$, —$C(CH_2CH_3)OH$, —$CH_2COOCH_2CH_3$, —$CH_2C(CH_3)_2OH$, —$CH_2COO$ H, or —$CH_2CON(CH_3)_2$.
Embodiment 7. The compound of embodiment 4, 5, or 6, wherein $R^2$ is H, F, —$CH_2OH$, —$CO_2Me$, or —$C(CH_3)_2OH$.

Embodiment 8. The compound of embodiment 4, 5, 6, or 7, wherein $R^3$ is H.

Embodiment 9. The compound of embodiment 4, 5, 6, 7, or 8, wherein $R^4$ is H, —$CH_3$, or —$CF_3$.

Embodiment 10. The compound of embodiment 1, 2, 3, 4, 5, 6, 7, 8, or 9, wherein D is optionally substituted cyclobutyl, optionally substituted phenyl, optionally substituted isoxazolyl, optionally substituted pyridinyl, isopropyl, or t-butyl.

Embodiment 11. The compound of embodiment 1, 2, 3, 4, 5, 6, 7, 8, 9, or 10, wherein each substituent of D, X, and Y, if present, independently has a molecular weight of 15 Da to 200 Da and consists of 2 to 5 chemical elements, wherein the chemical elements are independently C, H, O, N, S, F, Cl, or Br.

Embodiment 12. The compound of embodiment 4, 5, 6, 7, 8, 9, 10, or 11, wherein $R^1$ is H, Cl, Br, CN, $OCH_3$, $CF_3$, —$CO_2CH_2CH_3$, $C_{1-4}$ alkyl, or $C_{1-4}$ hydroxyalkyl.

Embodiment 13. The compound of embodiment 1, 2, 3, 4, 5, 6, 7, 8, 9, 10, 11, or 12, wherein D is optionally substituted cyclobutyl.

Embodiment 14. The compound of embodiment 1, 2, 3, 4, 5, 6, 7, 8, 9, 10, 11, or 12, wherein D is cyclobutyl.

Embodiment 15. The compound of embodiment 1, 2, 3, 4, 5, 6, 7, 8, 9, 10, 11, or 12, wherein D is optionally substituted phenyl.

Embodiment 16. The compound of embodiment 1, 2, 3, 4, 5, 6, 7, 8, 9, 10, 11, or 12, wherein D is optionally substituted isoxazolyl.

Embodiment 17. The compound of embodiment 1, 2, 3, 4, 5, 6, 7, 8, 9, 10, 11, or 12, wherein D is isopropyl.

Embodiment 18. The compound of embodiment 1, 2, 3, 4, 5, 6, 7, 8, 9, 10, 11, or 12, wherein D is t-butyl.

Embodiment 19. The compound of embodiment 1, 2, 3, 4, 5, 6, 7, 8, 9, 10, 11, or 12, wherein D is optionally substituted pyridinyl.

Embodiment 20. The compound of embodiment 1, 2, 3, 4, 5, 6, 7, 8, 9, 10, 11, 12, 13, 14, 15, 16, 17, 18, or 19, wherein X is optionally substituted phenyl.

Embodiment 21. The compound of embodiment 1, 2, 3, 4, 5, 6, 7, 8, 9, 10, 11, 12, 13, 14, 15, 16, 17, 18, or 19, wherein X is $CF_3$.

Embodiment 22. The compound of embodiment 1, 2, 3, 4, 5, 6, 7, 8, 9, 10, 11, 12, 13, 14, 15, 16, 17, 18, or 19, wherein X is F.

Embodiment 23. The compound of embodiment 1, 2, 3, 4, 5, 6, 7, 8, 9, 10, 11, 12, 13, 14, 15, 16, 17, 18, or 19, wherein X is optionally substituted pyridinyl.

Embodiment 24. The compound of embodiment 1, 2, 3, 4, 5, 6, 7, 8, 9, 10, 11, 12, 13, 14, 15, 16, 17, 18, or 19, wherein X is H.

Embodiment 25. The compound of embodiment 1, 2, 3, 4, 5, 6, 7, 8, 9, 10, 11, 12, 13, 14, 15, 16, 17, 18, 19, 20, 21, 22, 23, or 24, wherein Y is H.

Embodiment 26. The compound of embodiment 1, 2, 3, 4, 5, 6, 7, 8, 9, 10, 11, 12, 13, 14, 15, 16, 17, 18, 19, 20, 21, 22, 23, or 24, wherein Y is OH.

Embodiment 27. The compound of embodiment 1, 2, 3, 4, 5, 6, 7, 8, 9, 10, 11, 12, 13, 14, 15, 16, 17, 18, 19, 20, 21, 22, 23, or 24, wherein Y is F.

Embodiment 28. The compound of embodiment 1, 2, 3, 4, 5, 6, 7, 8, 9, 10, 11, 12, 13, 14, 15, 16, 17, 18, 19, 20, 21, 22, 23, or 24, wherein Y is $CF_3$.

Embodiment 29. The compound of embodiment 1, 2, 3, 4, 5, 6, 7, 8, 9, 10, 11, 12, 13, 14, 15, 16, 17, 18, 19, 20, 21, 22, 23, or 24, wherein Y is $C_{1-3}$ O-alkyl.

Embodiment 30. The compound of embodiment 1, 2, 3, 4, 5, 6, 7, 8, 9, 10, 11, 12, 13, 14, 15, 16, 17, 18, 19, 20, 21, 22, 23, or 24, wherein Y is $C_{0-6}$ fluoroamino.

Embodiment 31. The compound of embodiment 1, 2, 3, 4, 5, 6, 7, 8, 9, 10, 11, 12, 13, 14, 15, 16, 17, 18, 19, 20, 21, 22, 23, or 24, wherein Y is dimethylamino.

Embodiment 32. The compound of embodiment 1, 2, 3, 4, 5, 6, 7, 8, 9, 10, 11, 12, 13, 14, 15, 16, 17, 18, 19, 20, 21, 22, 23, or 24, wherein Y is methyl(2,2,2-trifluoroethyl)amino.

Embodiment 33. The compound of embodiment 1, 2, 3, 4, 5, 6, 7, 8, 9, 10, 11, 12, 13, 14, 15, 16, 17, 18, 19, 20, 21, 22, 23, or 24, wherein Y is optionally substituted tetrahydropyranyl.

Embodiment 34. The compound of embodiment 1, 2, 3, 4, 5, 6, 7, 8, 9, 10, 11, 12, 13, 14, 15, 16, 17, 18, 19, 20, 21, 22, 23, or 24, wherein Y is 1,1,1,3,3,3-hexafluoro-2-hydroxypropan-2-yl.

Embodiment 35. The compound of embodiment 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34, wherein A is $C_m$ alkyl; and wherein at least one of $R^1$, $R^2$, $R^3$, and $R^4$ are independently F, Cl, Br, I, or a substituent having a molecular weight of 15 Da to 200 Da and consisting of 2 to 5 chemical elements, wherein the chemical elements are independently C, H, O, N, S, F, Cl, or Br.

Embodiment 36. A compound represented by a formula:

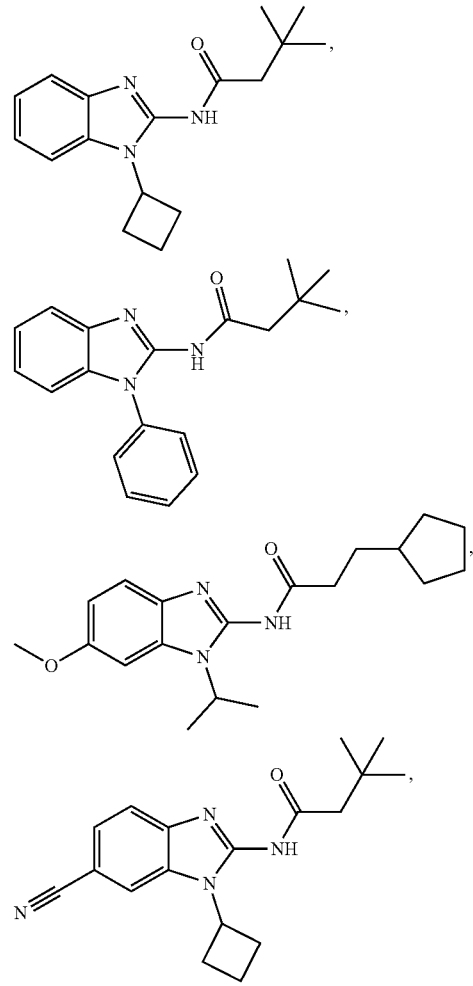

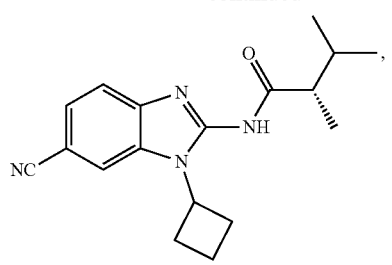
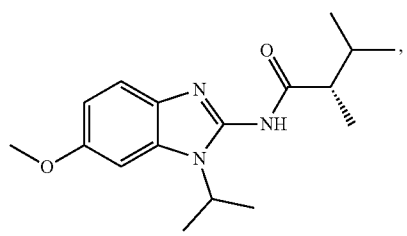
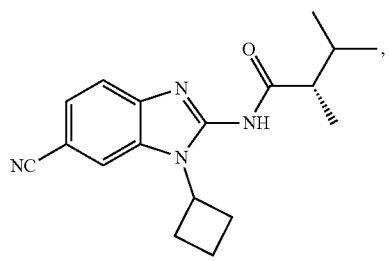
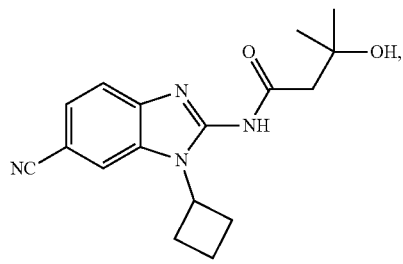
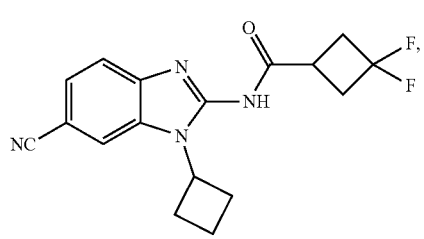
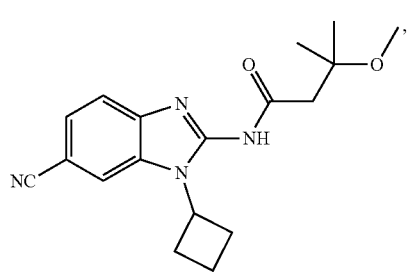
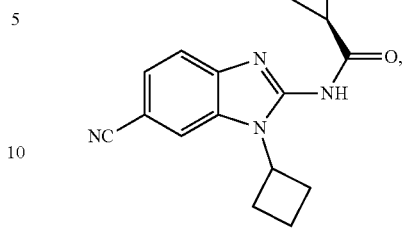
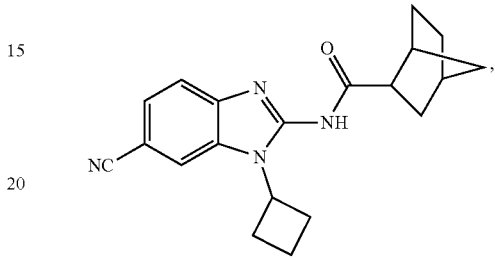
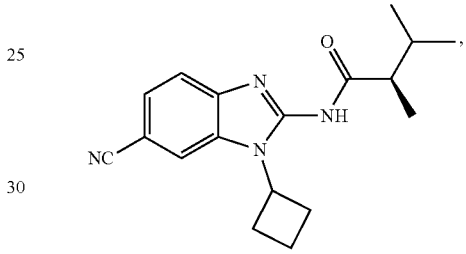
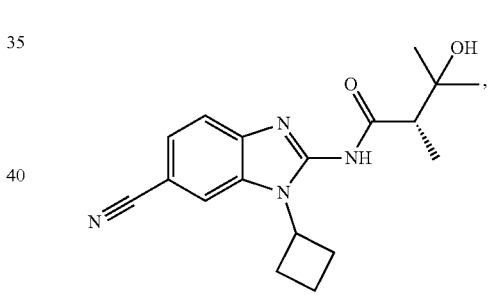
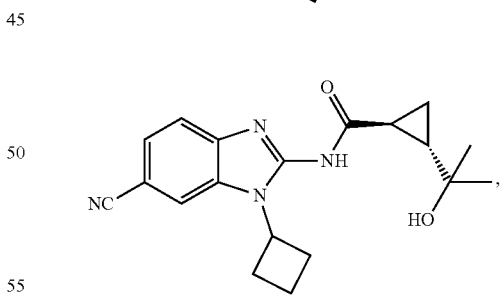
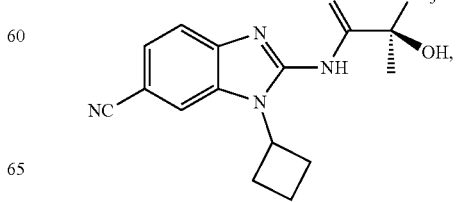

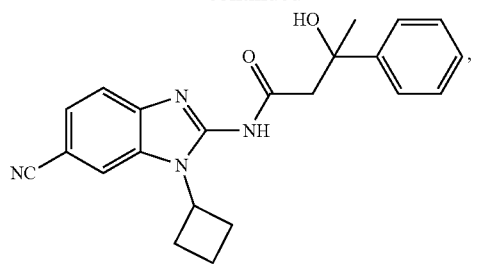
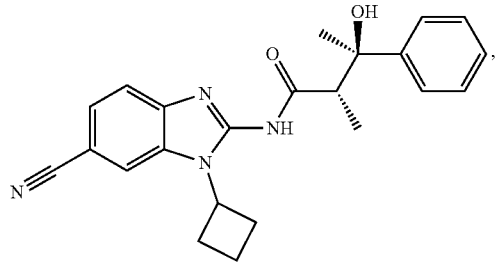
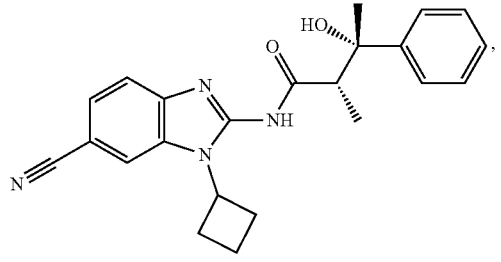
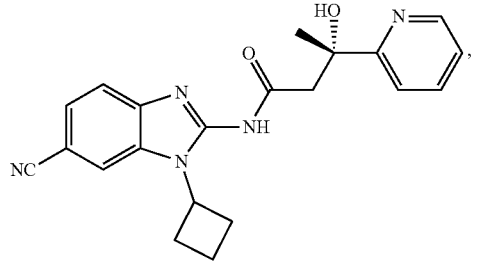
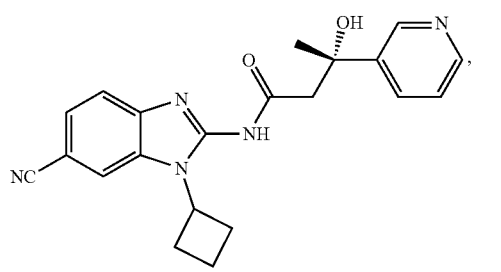
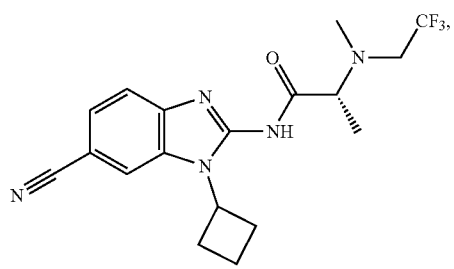
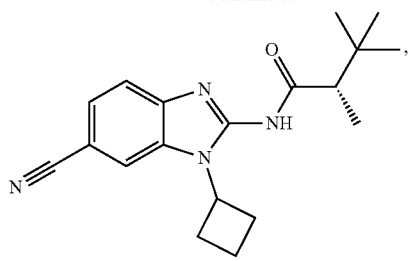
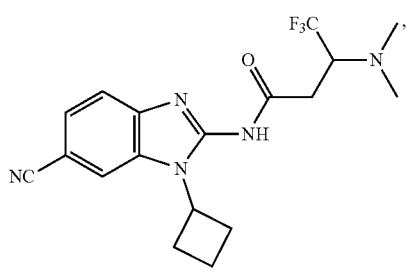
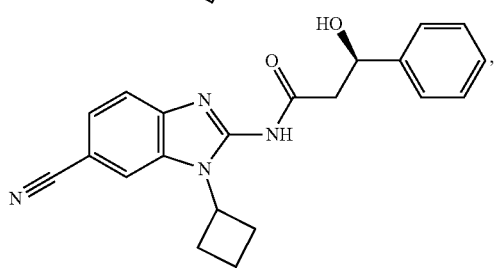
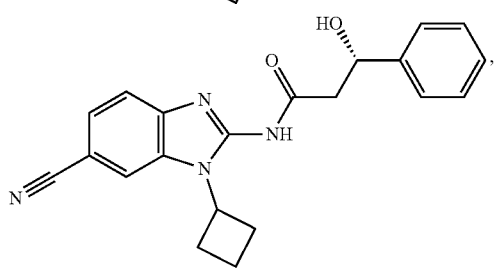
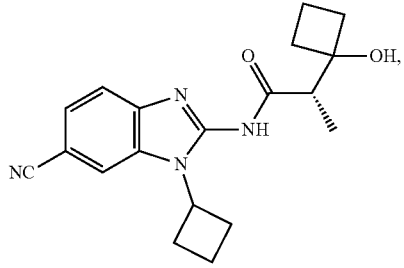
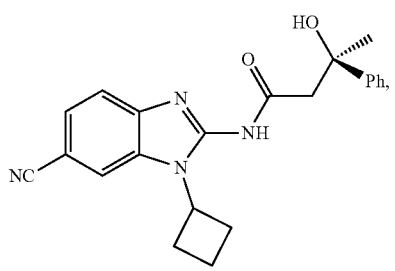

51
-continued
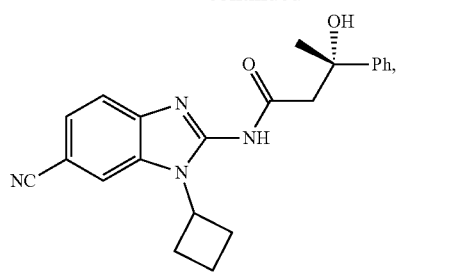
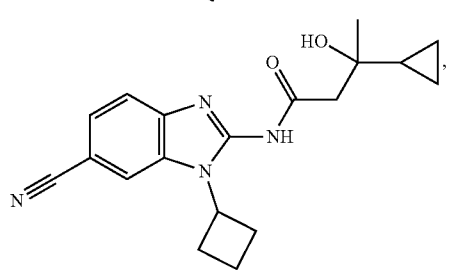
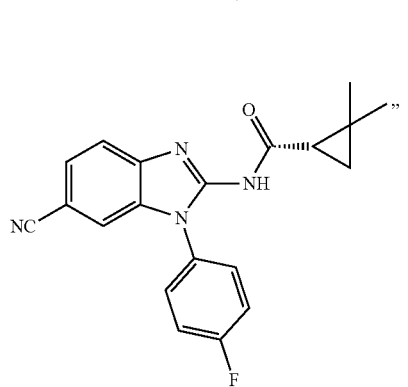
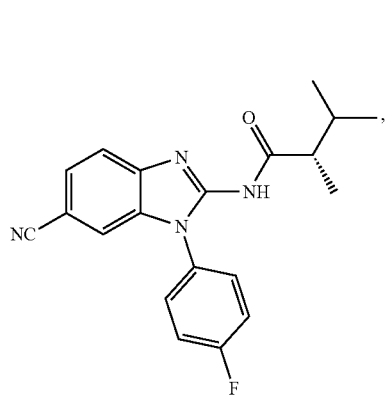
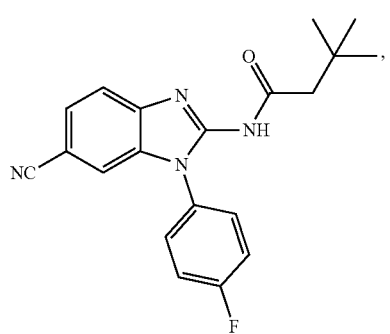
52
-continued
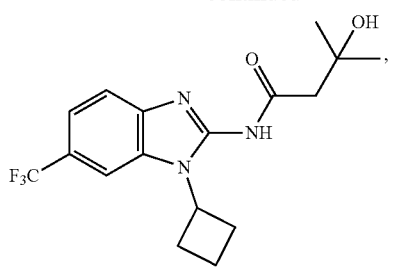
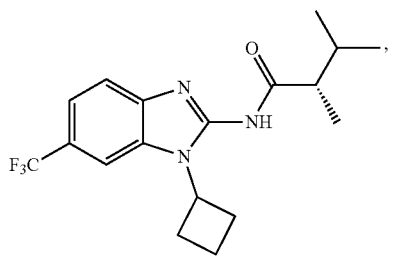
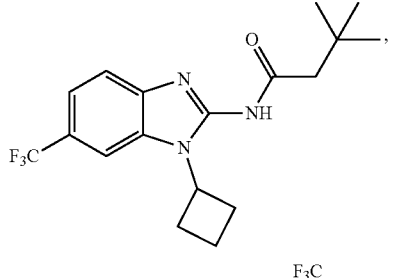
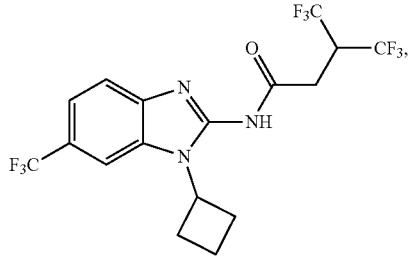
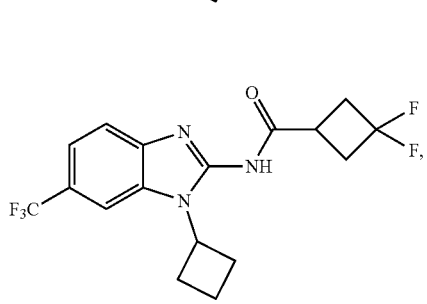
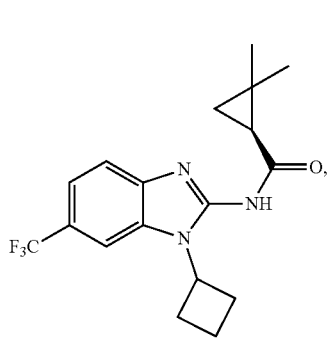

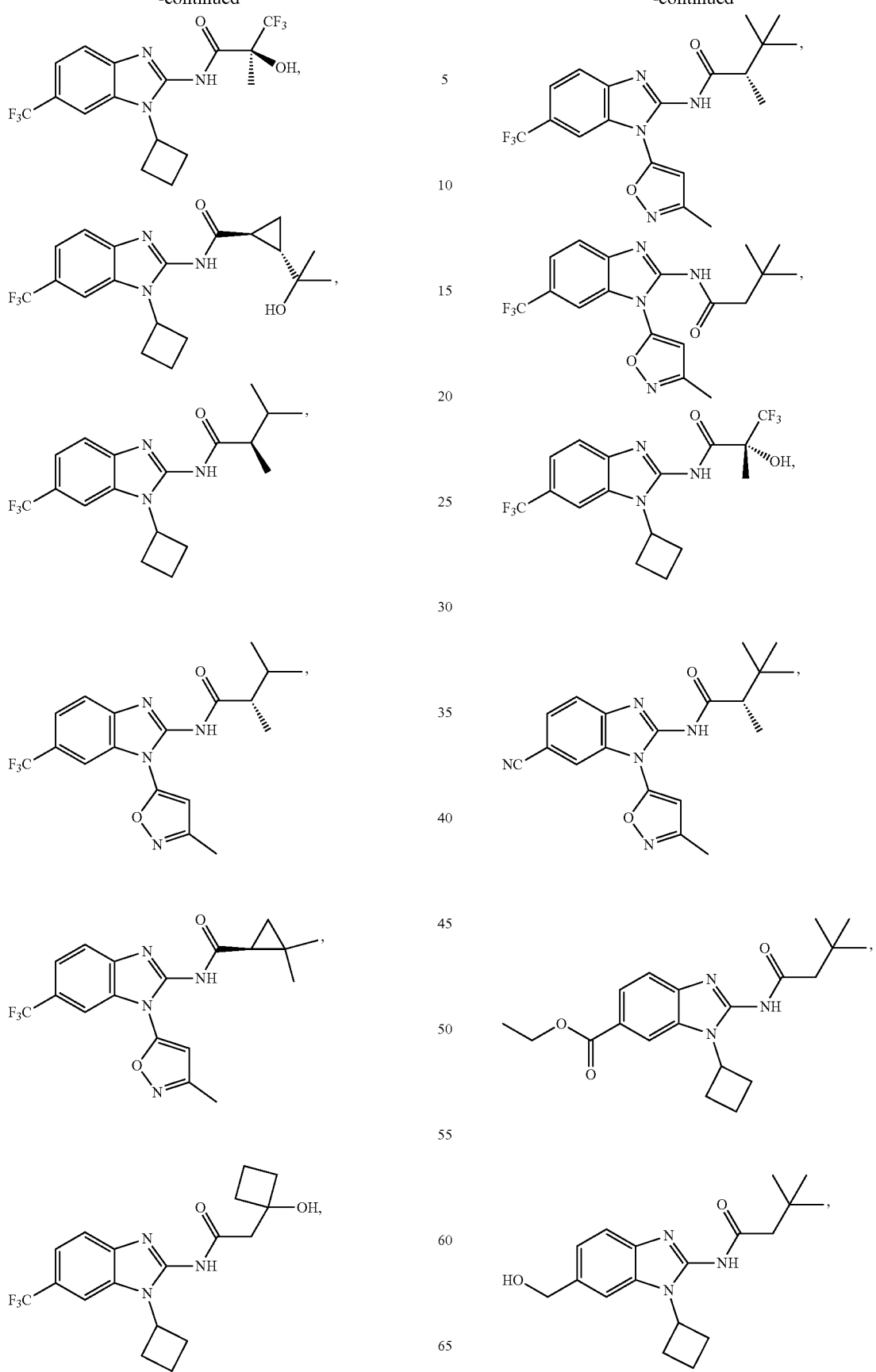

55
-continued
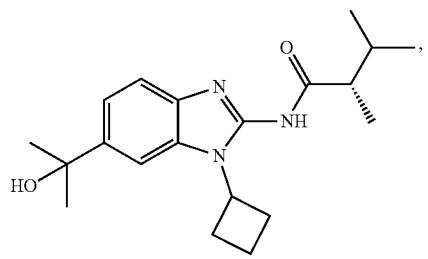
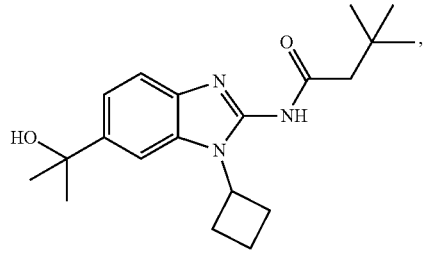
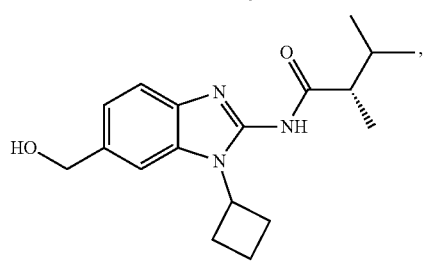
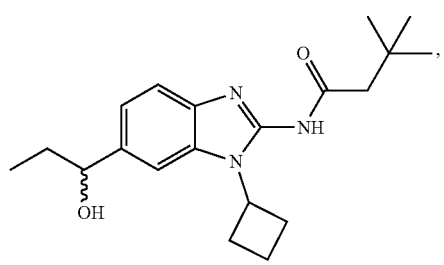
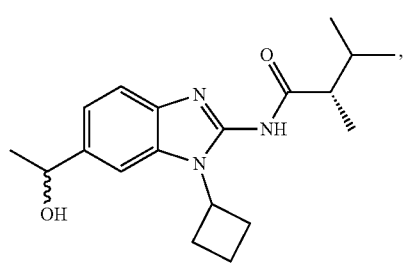
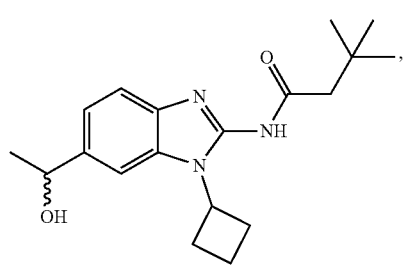
56
-continued
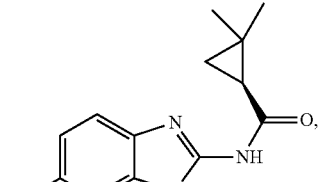
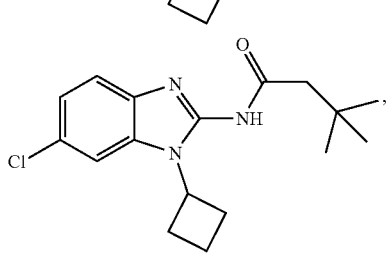
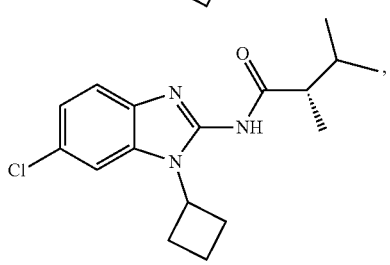
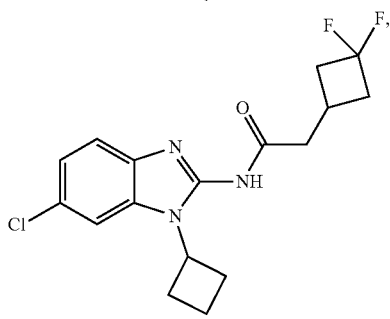
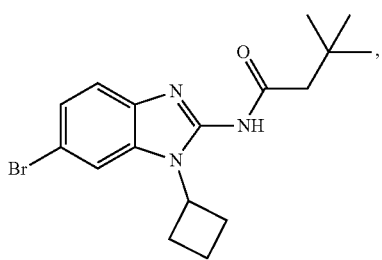
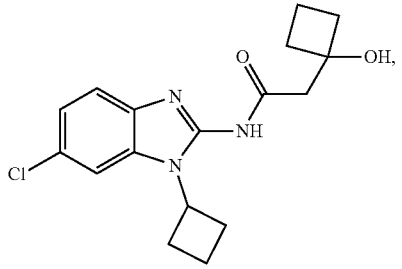

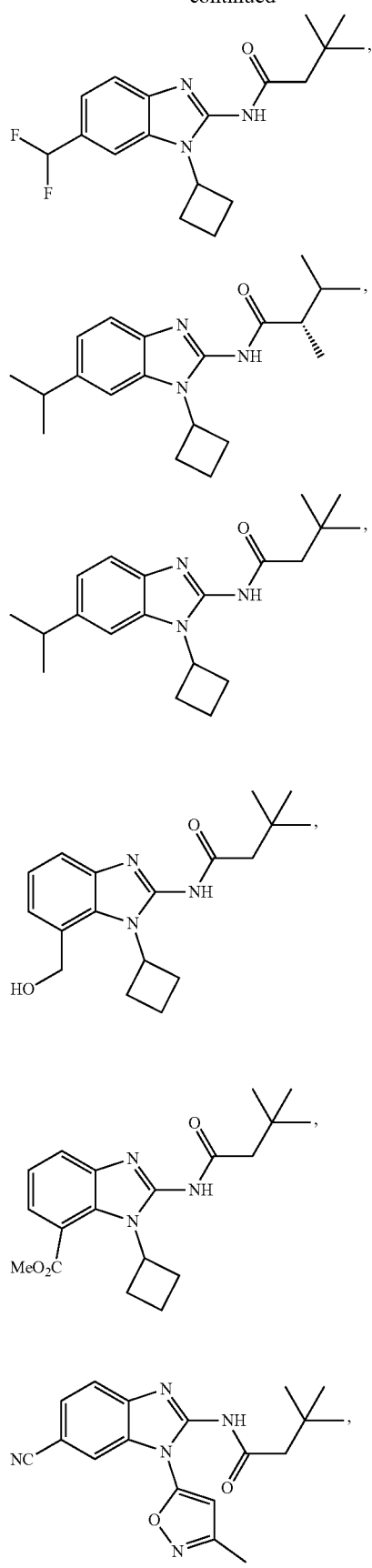
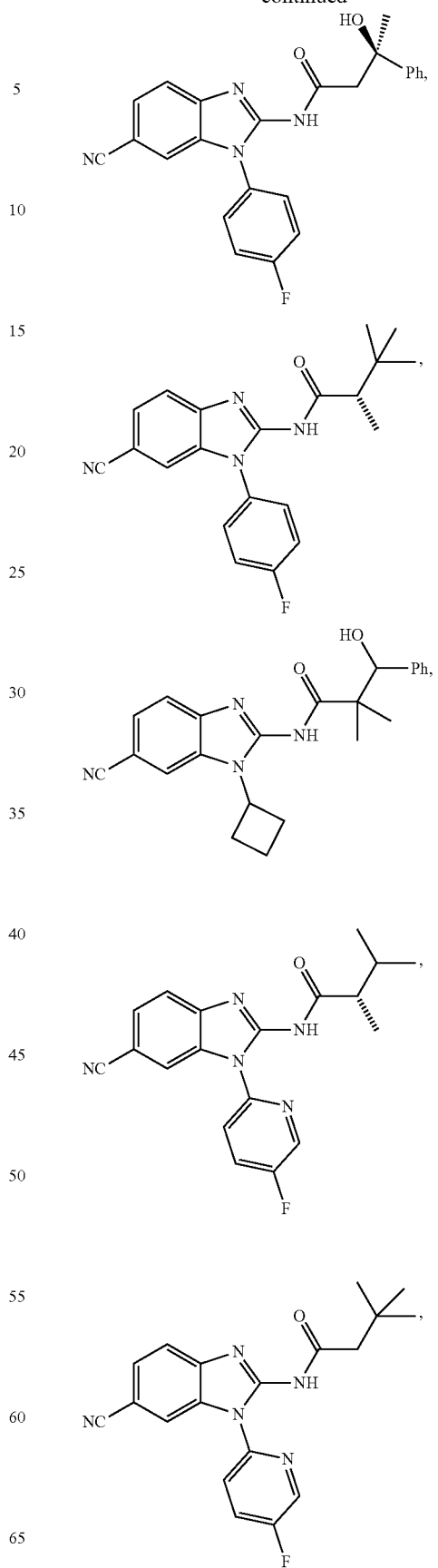

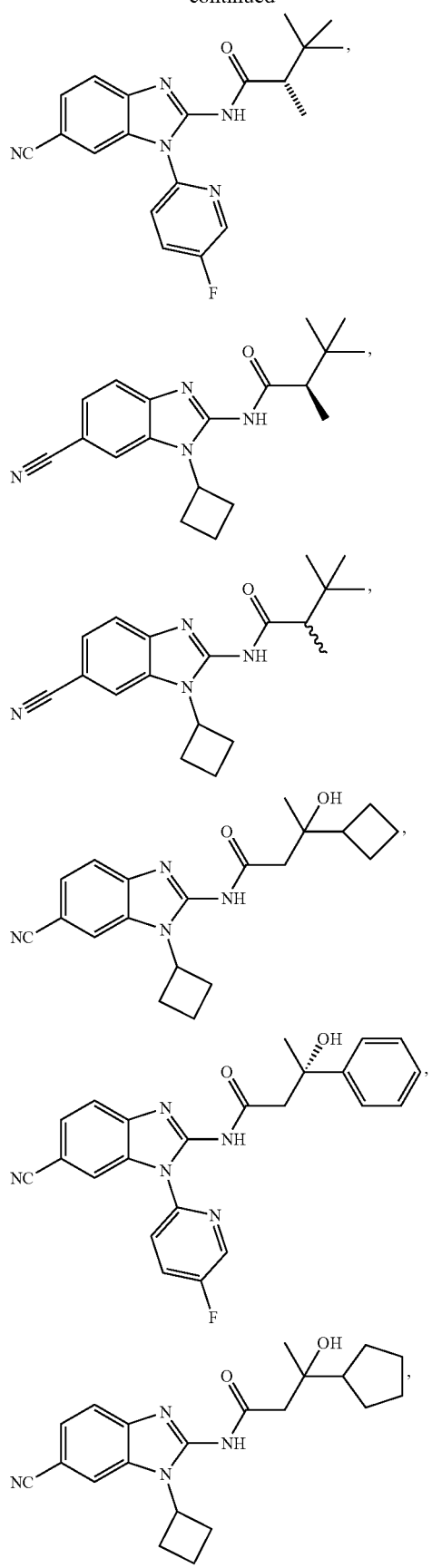

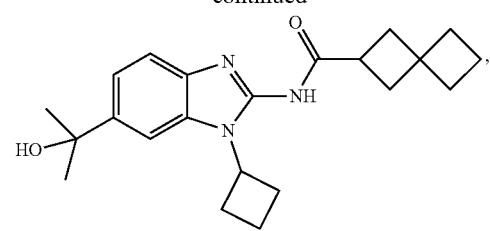
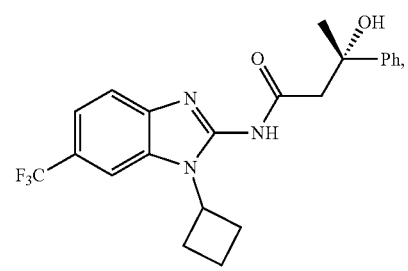
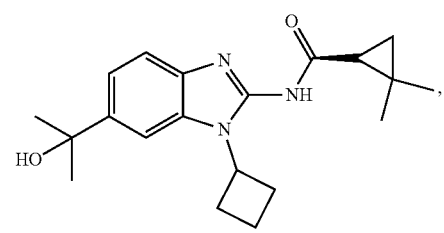
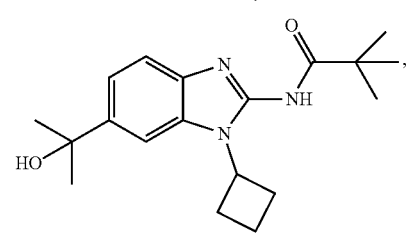
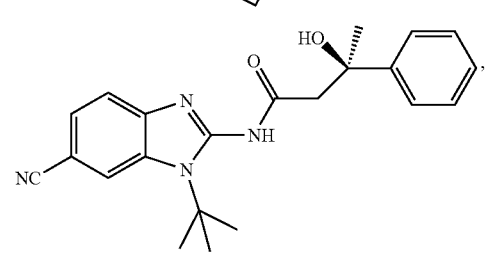
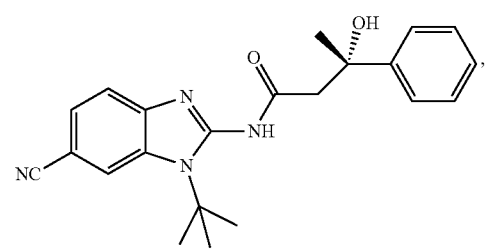
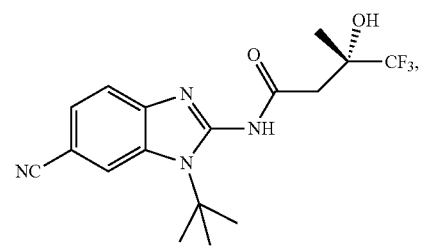
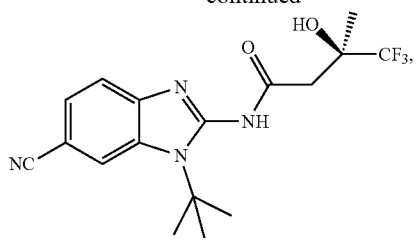
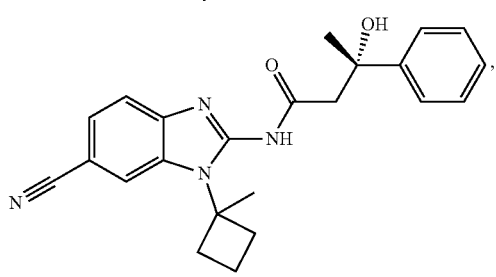
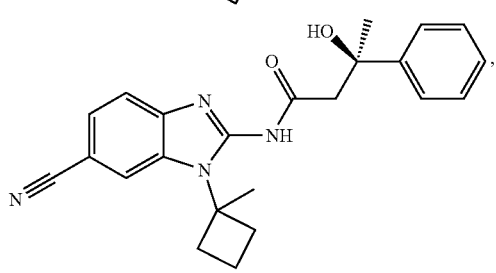
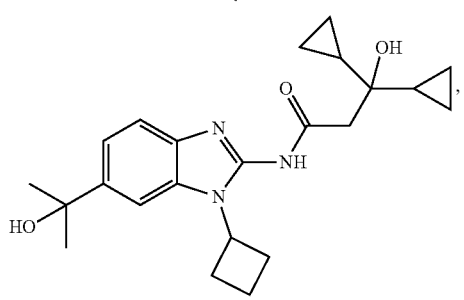
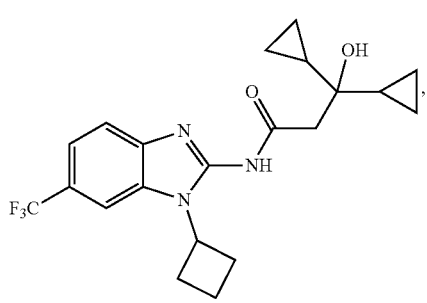
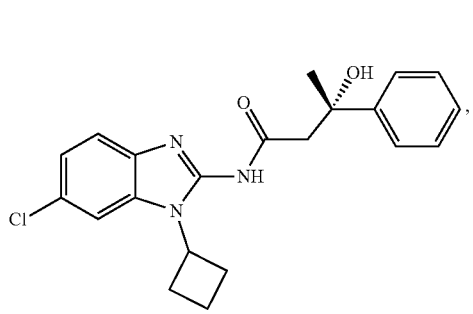

63
-continued
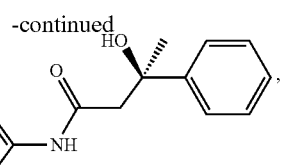
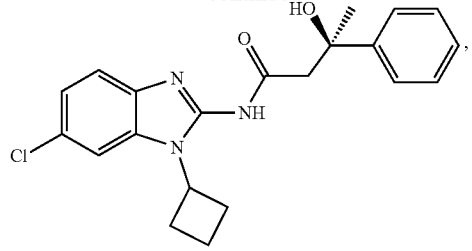
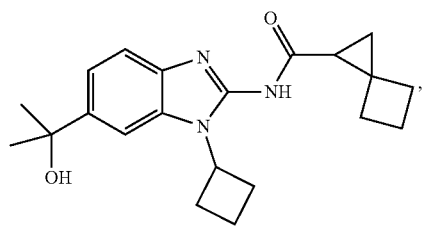
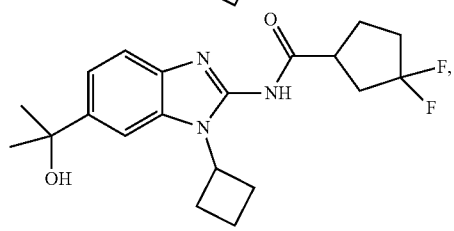
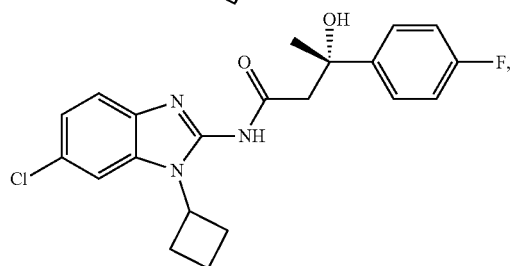
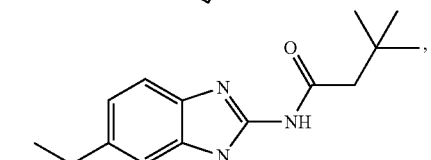
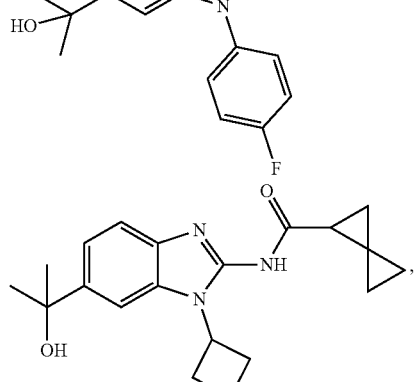
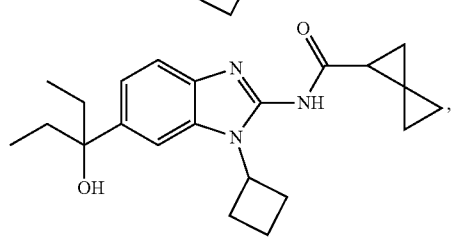
64
-continued
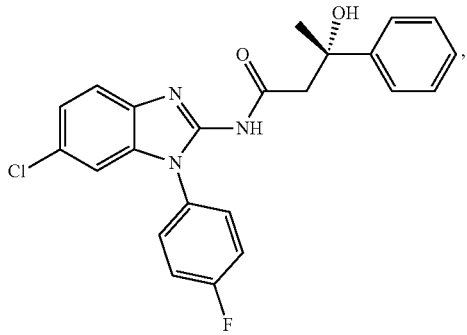
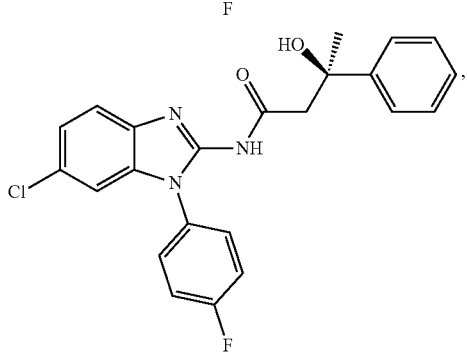
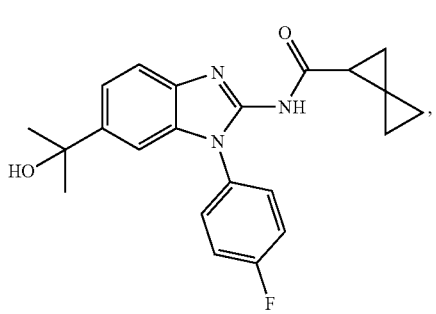
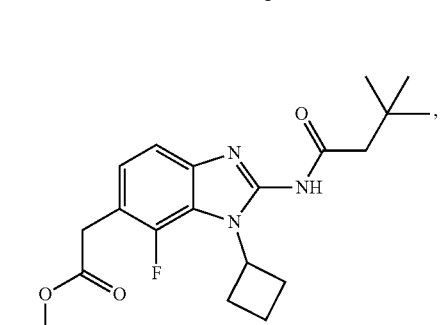
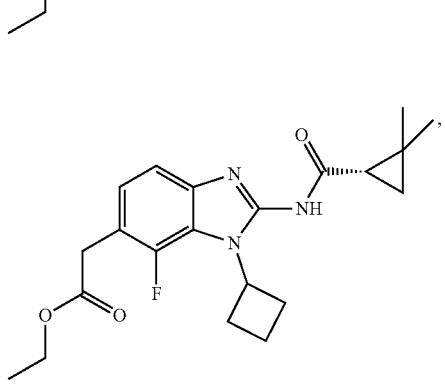

65
-continued
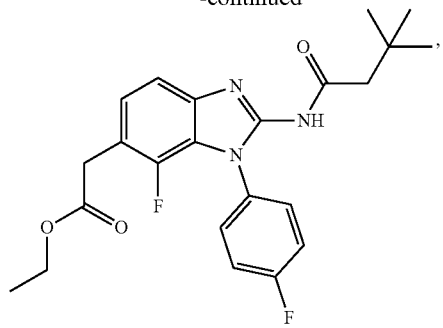
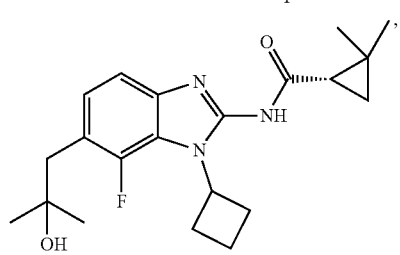
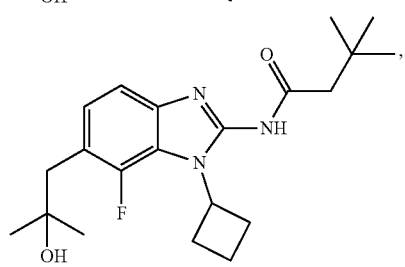
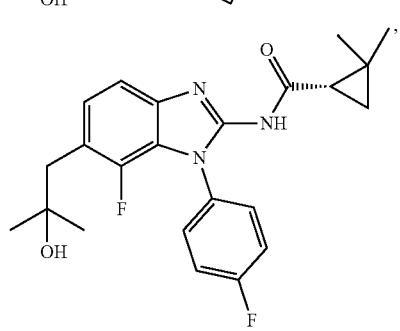
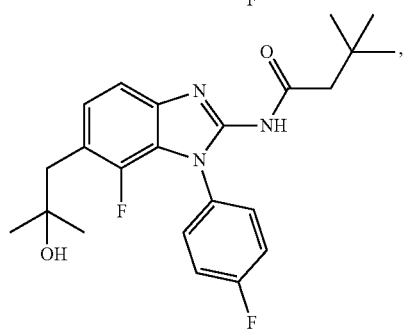
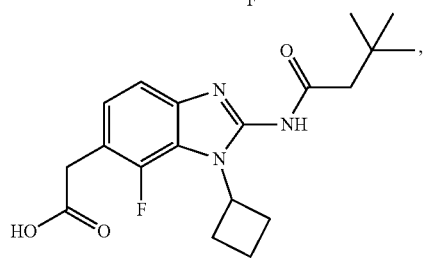
66
-continued
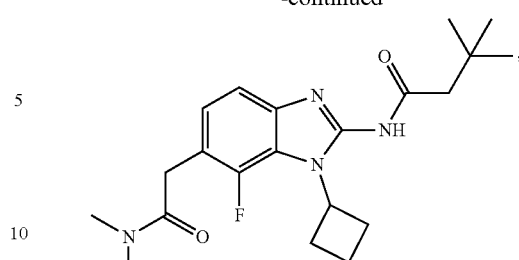
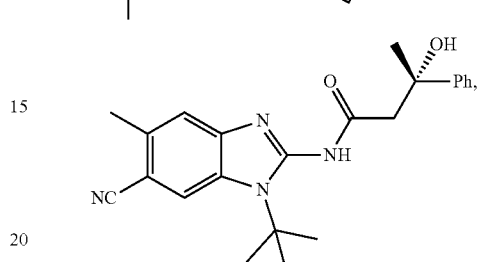
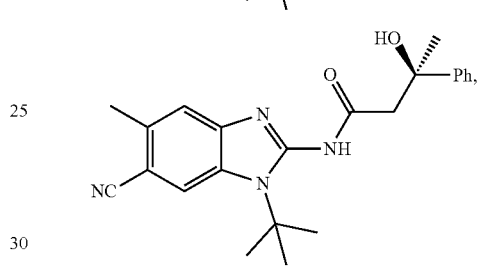
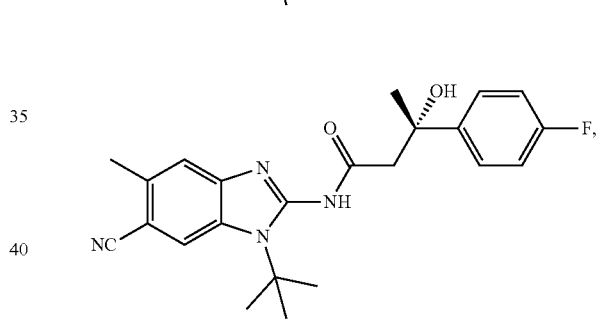
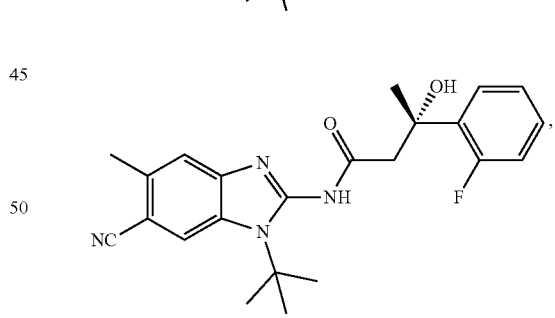
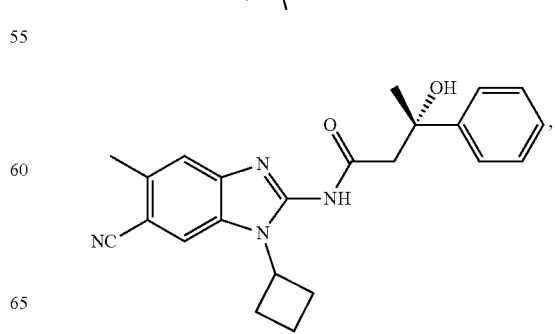

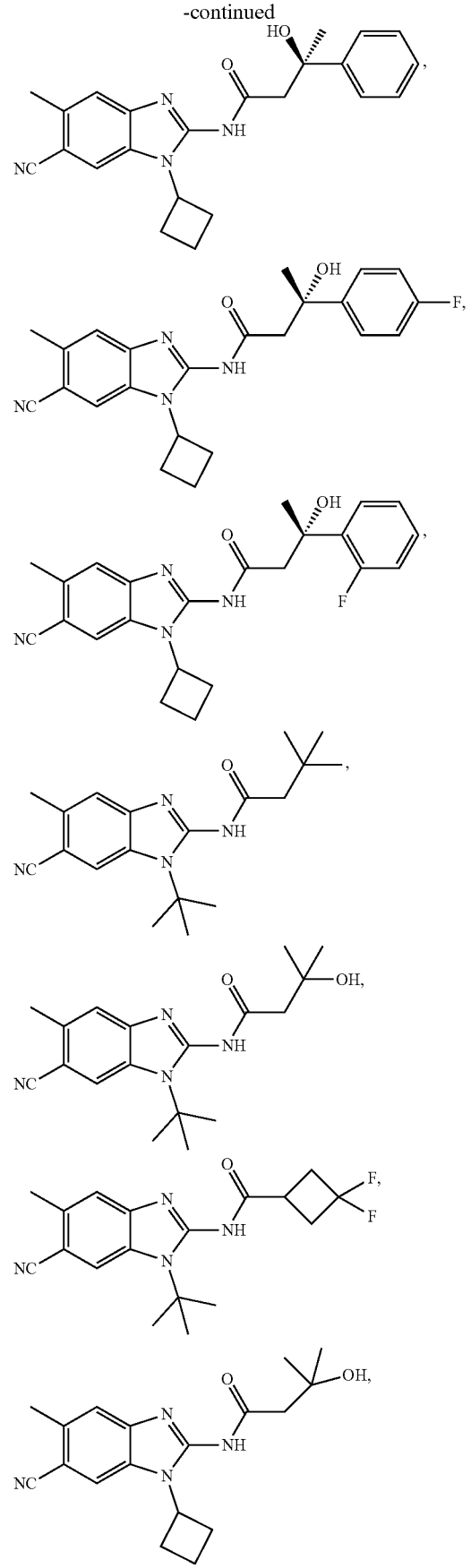
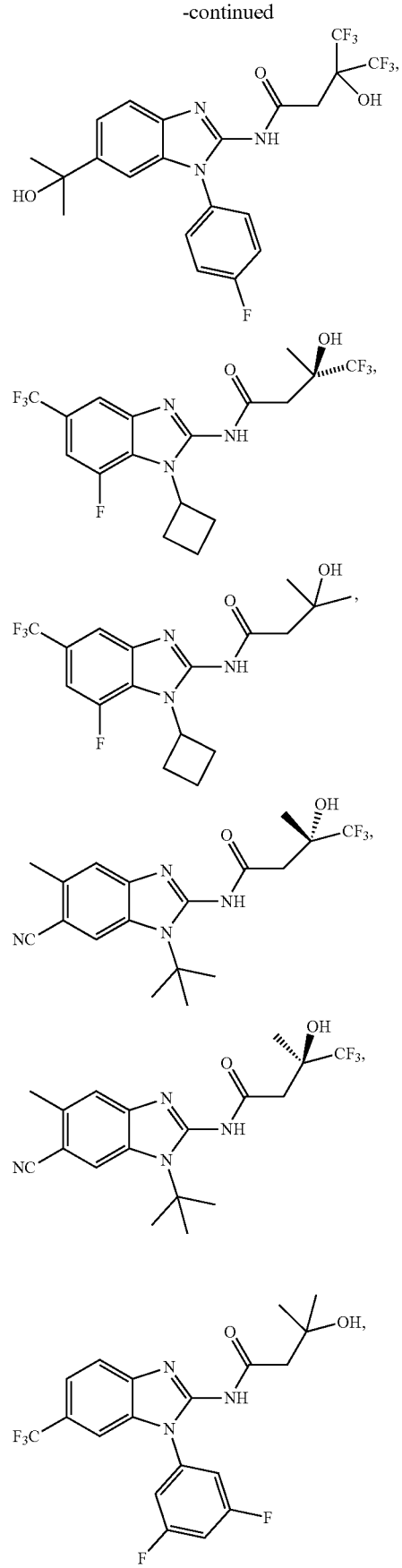

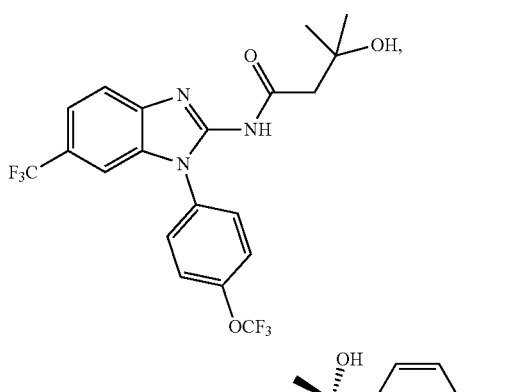

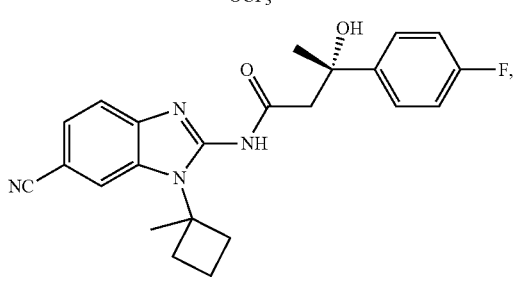

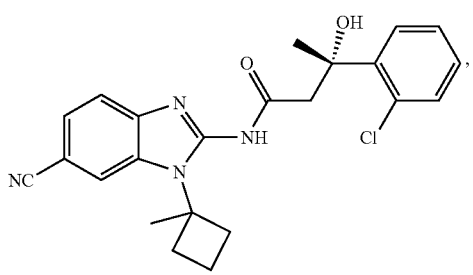

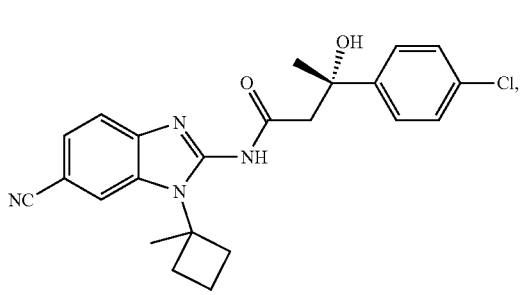

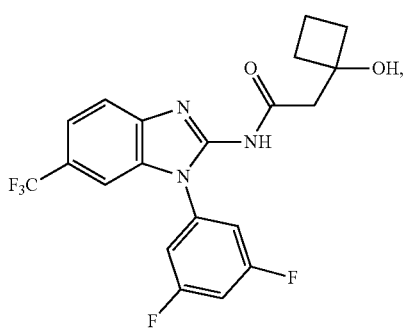

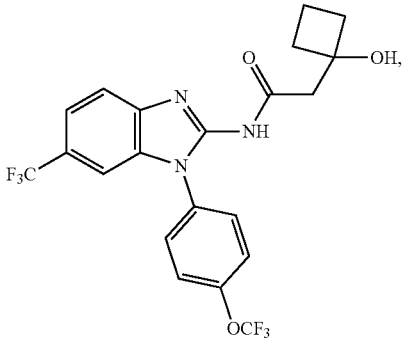

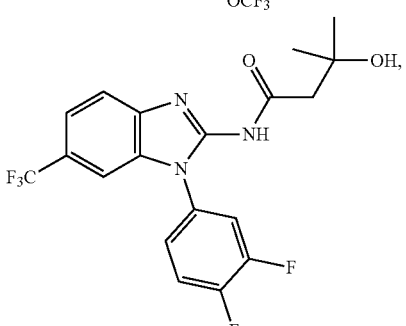

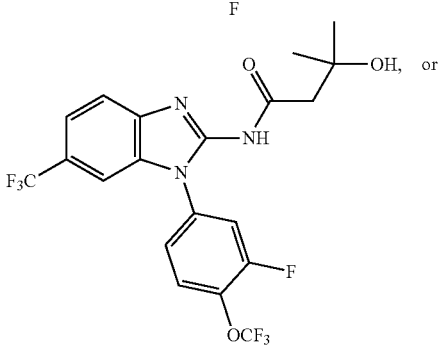

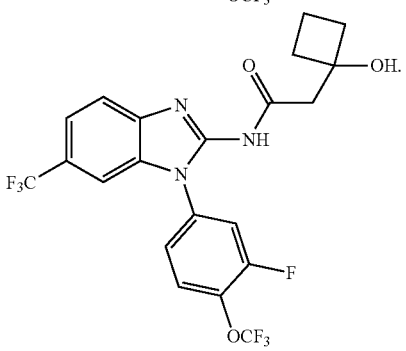

Embodiment 37. A composition comprising a compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36, wherein the composition is pharmaceutically acceptable.

Embodiment 38. A pharmaceutical dosage form comprising a compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36.

Embodiment 39. A method of treating a disorder associated with a Kv7 potassium channel activator comprising administering an effective amount of a compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36, to a mammal in need thereof.

Embodiment 40. The method of embodiment 39, wherein the disorder is epilepsy, pain, migraine, a disorder of neurotransmitter release, a smooth muscle contractility disorder, a dyskinesia, dystonia, mania, or a hearing disorder.

Embodiment 41. The method of embodiment 39, wherein the disorder is epilepsy, neuropathic pain, inflammatory pain, persistent pain, cancer pain, postoperative pain, migraine, anxiety, substance abuse, schizophrenia, a bladder disorder, a vasculature disorder, a dyskinesia, dystonia, mania, a hearing disorder, or tinnitus.

Embodiment 42. Use of a compound of embodiment 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36, in the manufacture of a medicament for the treatment of a disorder associated with a Kv7 potassium channel activator.

Embodiment 43. The use of embodiment 42, wherein the disorder is epilepsy, pain, migraine, a disorder of neurotransmitter release, a smooth muscle contractility disorder, a dyskinesia, dystonia, mania, or a hearing disorder.

Embodiment 44. The use of embodiment 42, wherein the disorder is epilepsy, neuropathic pain, inflammatory pain, persistent pain, cancer pain, postoperative pain, migraine, anxiety, substance abuse, schizophrenia, a bladder disorder, a vasculature disorder, a dyskinesia, dystonia, mania, a hearing disorder, or tinnitus.

Experimental Section

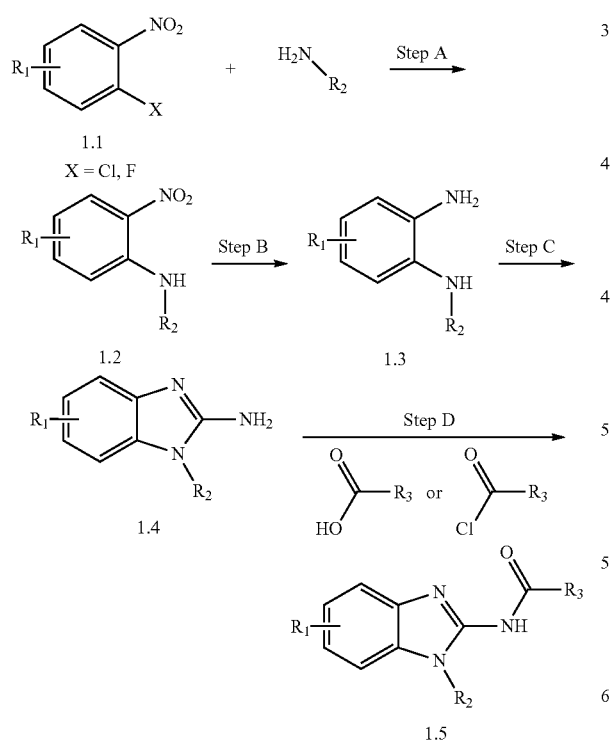

Scheme 1 shows a general methodology for the synthesis of 1H-benzo[d]imidazol-2-yl amides 1.5. An appropriately substituted 1-fluoro-2-nitrobenzene 1.1 is reacted with a primary amine to afford 1-amino-2-nitrobenzene 1.2. Alternatively, a 1-chloro-2-nitrobenzene is reacted with a primary amine under palladium catalysis to provide the desired 1-amino-2-nitrobenzene 1.2. The nitro group may be reduced to the corresponding amine by a variety of well-established methods to provide 1,2-diaminobenzenes 1.3. Reaction of 1.3 with cyanogen bromide affords 1H-benzo[d]imidazol-2-amines 1.4. Amide coupling with either an appropriate carboxylic acid or acyl chloride can afford 1H-benzo[d]imidazol-2-yl amides such as 1.5.

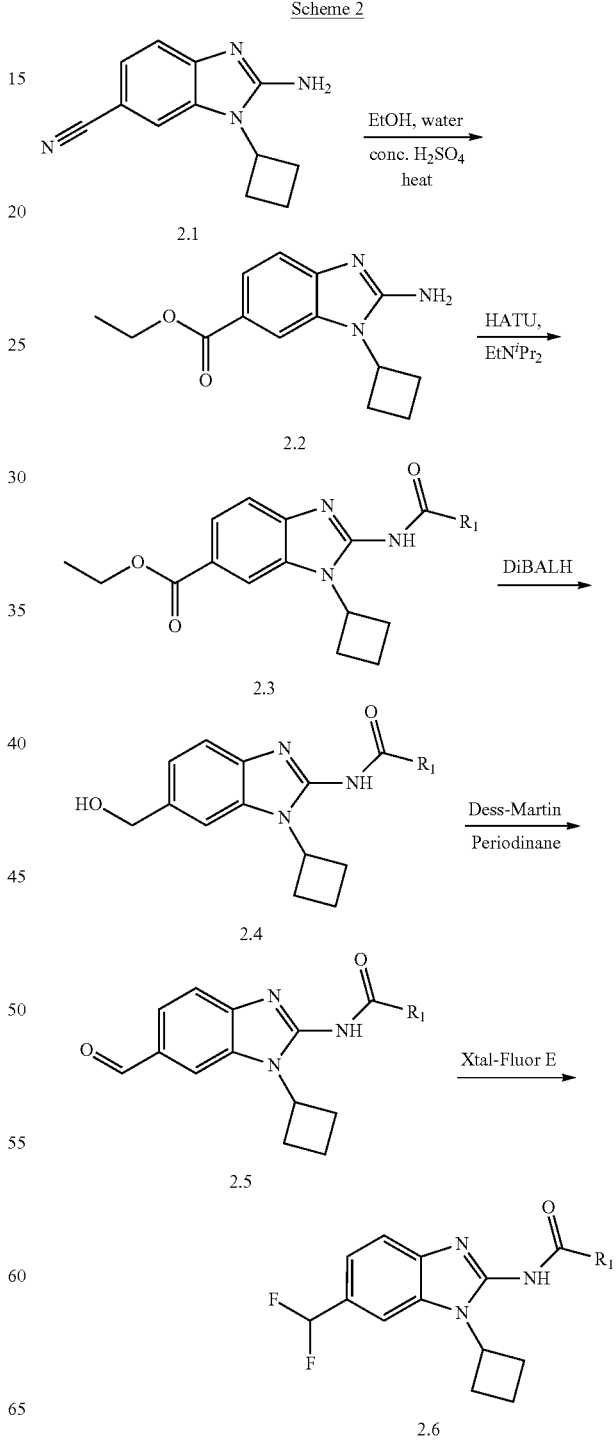

-continued

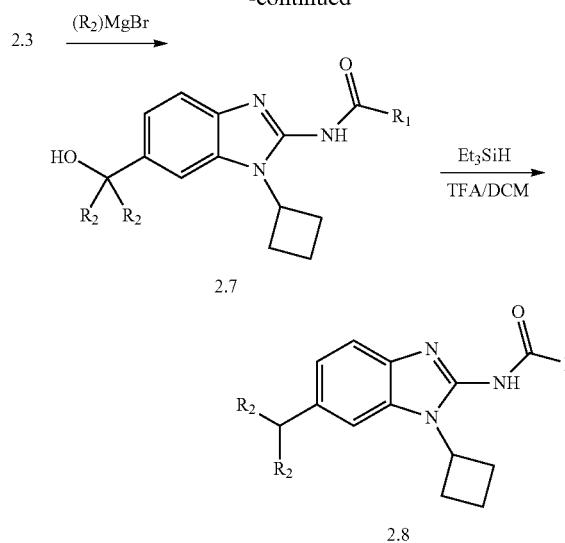

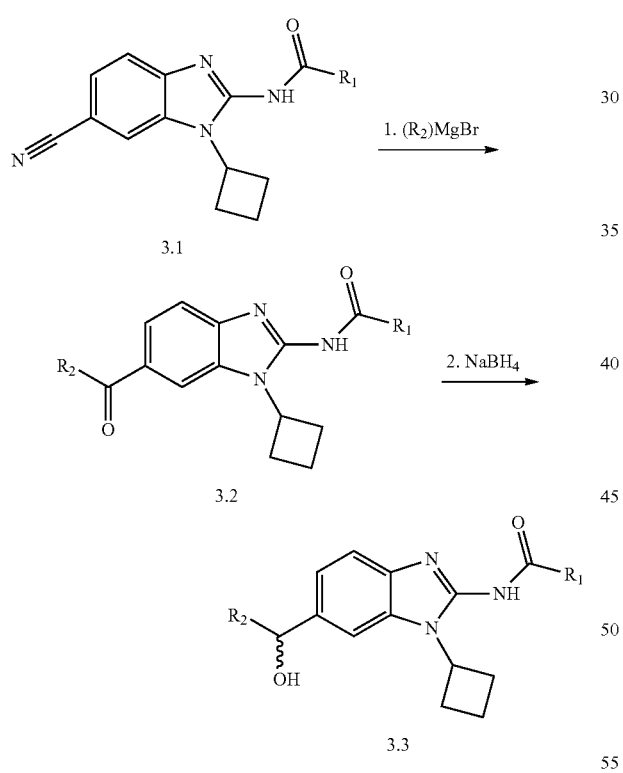

Scheme 2 and Scheme 3 describe general methodologies that may be used to create novel Kv7 modulators after the initial amide bond forming reaction has been used to synthesize 1H-benzo[d]imidazol-2-yl amides such as 2.3. Sulfuric acid-promoted ethanolysis of the nitrile in 2-amino-1-cyclobutyl-1H-benzo[d]imidazole-6-carbonitrile (2.1) gives the ethyl ester 2.2. This amino-heterocycle may be used as the amine in a standard amide bond forming reaction to give the ester amide 2.3. The ethyl ester may serve as a synthetic handle to access various other functional groups. The ester may be reduced with DiBAL-H to the primary alcohol 2.4.

Alternatively, excess Grignard reagent may be used to generate a tertiary alcohol 2.7. The primary alcohol 2.4 may be readily oxidized with the Dess-Martin periodinane or a similar oxidant to generate an intermediate aldehyde 2.5. The aldehyde 2.5 may serve as the input for a difluorination reaction, for example using Xtal-FluorE reagent, to provide the difluoromethyl-substituted amides 2.6 (see Couturier, M, et al, *J. Org. Chem.* 2010, 75, 3401-3411). The tertiary alcohols 2.7 may be reduced under the action of triethylsilane and trifluoroacetic acid in dichloromethane to give the branched benzylic alkyl groups present in amides 2.8. It is noteworthy that the new molecules 2.4-2.8 are convenient as intermediates for further conversion into additional benzo-ring substituents, such as amides, ethers, and heterocycles, using known methodologies.

A range of functional groups may be orthogonally transformed in the presence of the amide functionality of 1H-benzo[d]imidazol-2-yl amides. Scheme 3 shows how the nitrile 3.1 may be selectively reacted with a Grignard reagent to produce an aryl ketone 3.2. This ketone may be reduced with common hydride reagents, such as sodium borohydride, to give the secondary alcohol 3.3. Such ketone reductions may be conducted in a stereochemically-defined manner, using a variety of chiral reducing reagents known in the literature (e.g. via CBS reagent, see Corey, E J, Shibata, S, Bakshi, R K, *J. Org. Chem.* 1988, 53, 2861-2863).

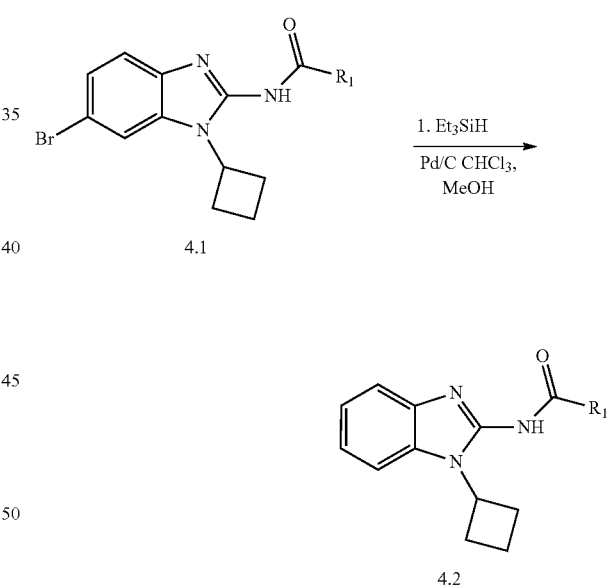

The general methodology of Scheme 1 may be used to synthesize a wide range of functionalized 1H-benzo[d] imidazol-2-yl amides. Bromide 4.1 in Scheme 4 is an example of a halogenated-1H-benzo[d]imidazol-2-yl amide that also provides an orthogonally reactive functional group. The bromide may be reduced with the action of triethylsilane in chloroform and methanol with a catalytic amount of palladium on charcoal to give the debrominated product 4.2 (see Mandal, P K, McMurray, J S, *J. Org. Chem.* 2007, 72, 6599-6601). The aromatic bromide in 4.1 may also be used to perform palladium cross coupling reactions such as Sonogashira, Suzuki, or Stille reactions to provide alkynes, biaryl or other cross coupled products.

Scheme 5

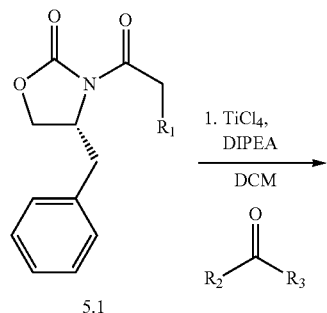

5.1

1. TiCl₄, DIPEA
DCM $R_2\text{COR}_3$

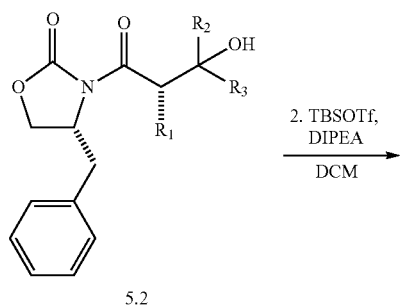

5.2

2. TBSOTf, DIPEA
DCM

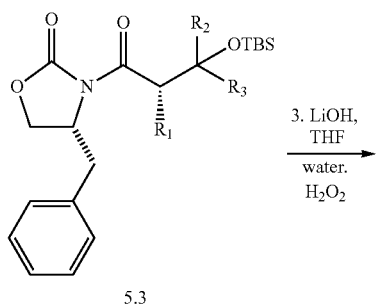

5.3

3. LiOH, THF
water.
H₂O₂

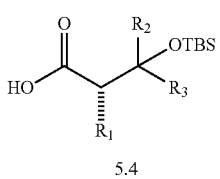

5.4

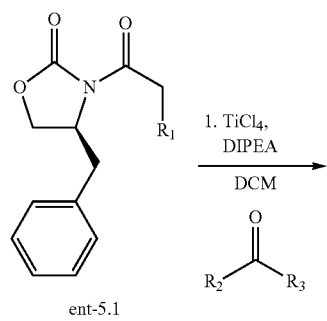

ent-5.1

1. TiCl₄, DIPEA
DCM $R_2\text{COR}_3$

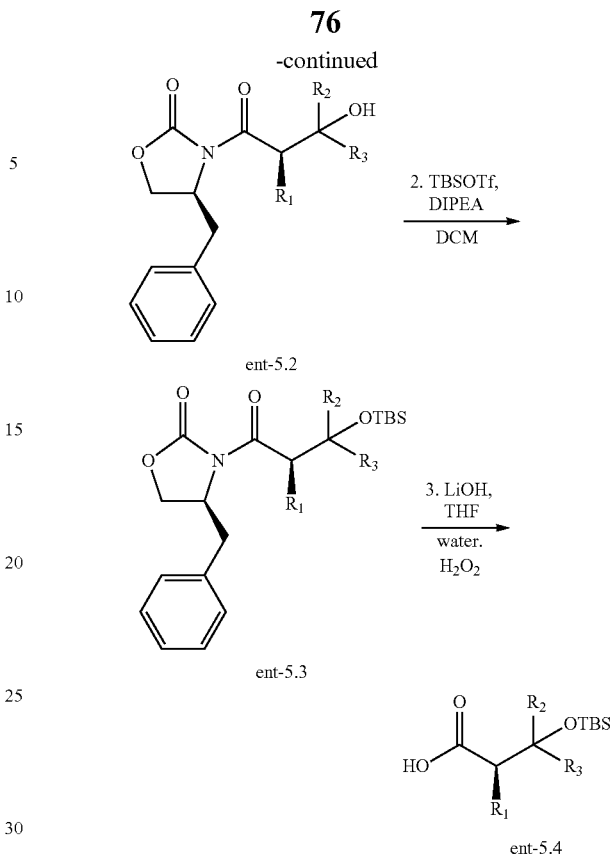

Scheme 5 describes a general synthetic method for the synthesis of chiral α-alkyl carboxylic acids that contain β-silyloxy ether protected acids 5.4 or ent-5.4. These optically active acids are used as the acid component in amide forming reaction (Step D of Scheme 1) to give β-tertiary alcohol amides. The diastereoselective bond construction via titanium enolate chemistry described by Evans was used to condense chiral imide 5.1 or ent-5.1 with a ketone or other electrophile to give diastereomerically pure aldol adducts 5.2 or ent-5.2, respectively (see Evans, D A, Urpi, F, Somers, T C, Clark, J S, Bilodeau, M T, *J. Am. Chem. Soc.* 1990, 112, 8215-8216). The proper choice of chiral imide 5.1 will give rise to the desired absolute stereochemistry of the α-stereocenter in the carboxylic acids 5.4 or ent-5.4. Silyl ether protection of the aldol adducts 5.2 and ent-5.2 with tert-butyldimethylsilyltriflate and diisopropylethylamine gives the tert-butyldimethylsilyl ethers 5.3 and ent-5.3. Standard acyl oxazolidinone hydrolysis conditions using lithium hydroxide and hydrogen peroxide in tetrahydrofuran and water provides the desired acids 5.4 or ent-5.4 (see Evans, D A, Britton, T C, Ellman, J A, *Tetrahedron Lett.* 1987, 28(49), 6141-6144). Proper selection of ketones or other electrophiles in the titanium enolate chemistry will give rise to appropriately substituted aldol adducts that vary in the nature of the $R_2$ and $R_3$ groups. Changing the $R_1$ group of the starting imides 5.1 and ent-5.1 may be used to vary the size and nature of the $R_1$ group in the acids 5.4 or ent-5.4. This methodology allows one to synthesize a wide range of optically active acids with absolute stereocontrol of the α-chiral center to the carbonyl of the carboxylic acid.

Scheme 6

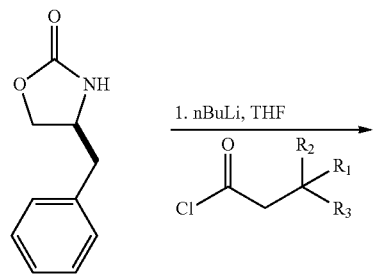

6.1

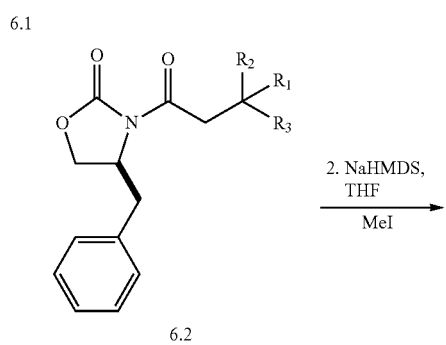

6.2

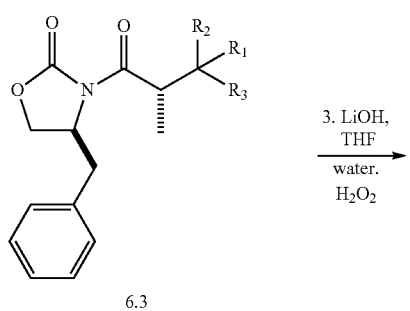

6.3

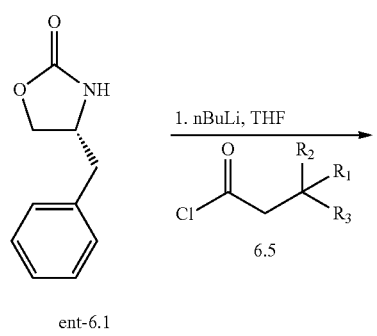

ent-6.1

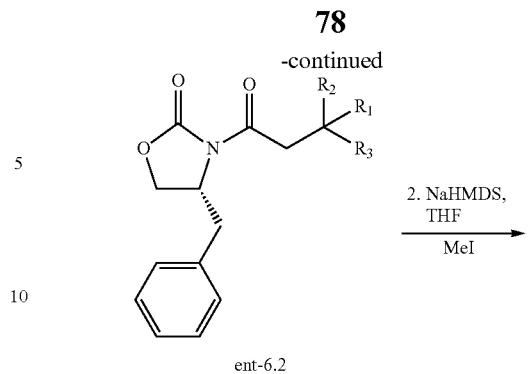

ent-6.2

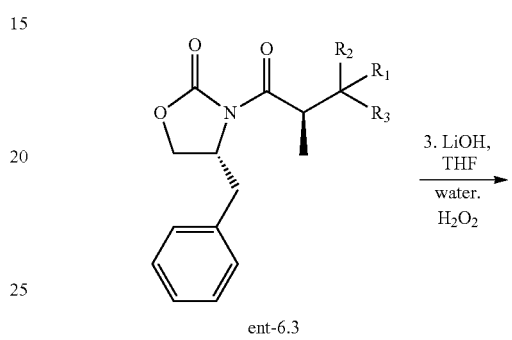

ent-6.3

ent-6.4

A general synthetic method for the synthesis of enantiomerically pure α-methyl-β-branched chiral carboxylic acids 6.4 or ent-6.4 is described in Scheme 6. Both of the enantiomerically pure oxazolidinones (S)-4-benzyloxazolidin-2-one 6.1 and (R)-4-benzyloxazolidin-2-one ent-6.1 are commercially available. These oxazolidinones may be readily acylated by deprotonation with n-butyl lithium followed by reaction with acid chlorides 6.5 to give the chiral imides 6.2 and ent-6.2, respectively. There are a large number of commercially available acid chlorides 6.5 with wide variation about the $R_1$, $R_2$ and $R_3$ groups of this input. This allows for the rapid synthesis of chiral imides 6.2 and ent-6.2 that have differing substitution at the β-position to the exocyclic carbonyl group. The asymmetric alkylation reaction of chiral imide sodium enolates as developed by Evans may then be used to introduce a methyl group in a stereoselective fashion (see Evans, D A, Ennis, M D, Mathre, D J, *J. Am. Chem. Soc.* 1982, 104, 1737-1739). The sodium enolate of imide 6.2 may be produced by treatment of 6.2 with sodium hexamethyldisilazide in tetrahydrofuran. The resultant sodium enolate may then be stereoselectively methylated by the addition of methyl iodide. The pure and single diastereomers 6.3 and ent-6.3 may be isolated by silica gel column chromatography. Alternatively, the single diastereomers may be obtained by recrystallization of crystalline products 6.3 and ent-6.3. The well-known chiral auxiliary hydrolysis conditions as described above for Scheme 5 give the optically active α-methyl β-branched chiral carboxylic acids 6.4 or ent-6.4, respectively.

Scheme 7

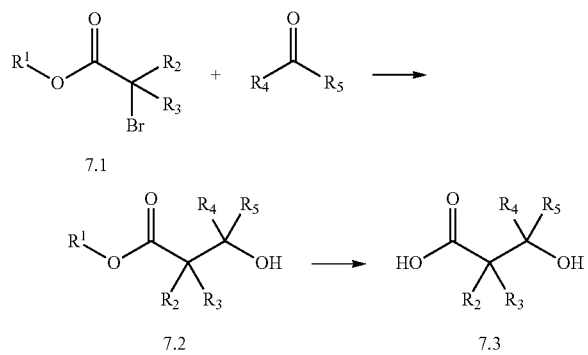

Scheme 7 shows a general methodology for the synthesis of 3-hydroxypropanoic acids such as 7.3. An appropriately substituted 2-bromoethanoic ester 7.1 is reacted with a ketone or aldehyde to afford 3-hydroxypropanoic esters 7.2. The ester group may be hydrolyzed to the corresponding acid by saponification to provide 3-hydroxypropanoic acids such as 7.3.

Scheme 8

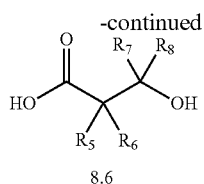

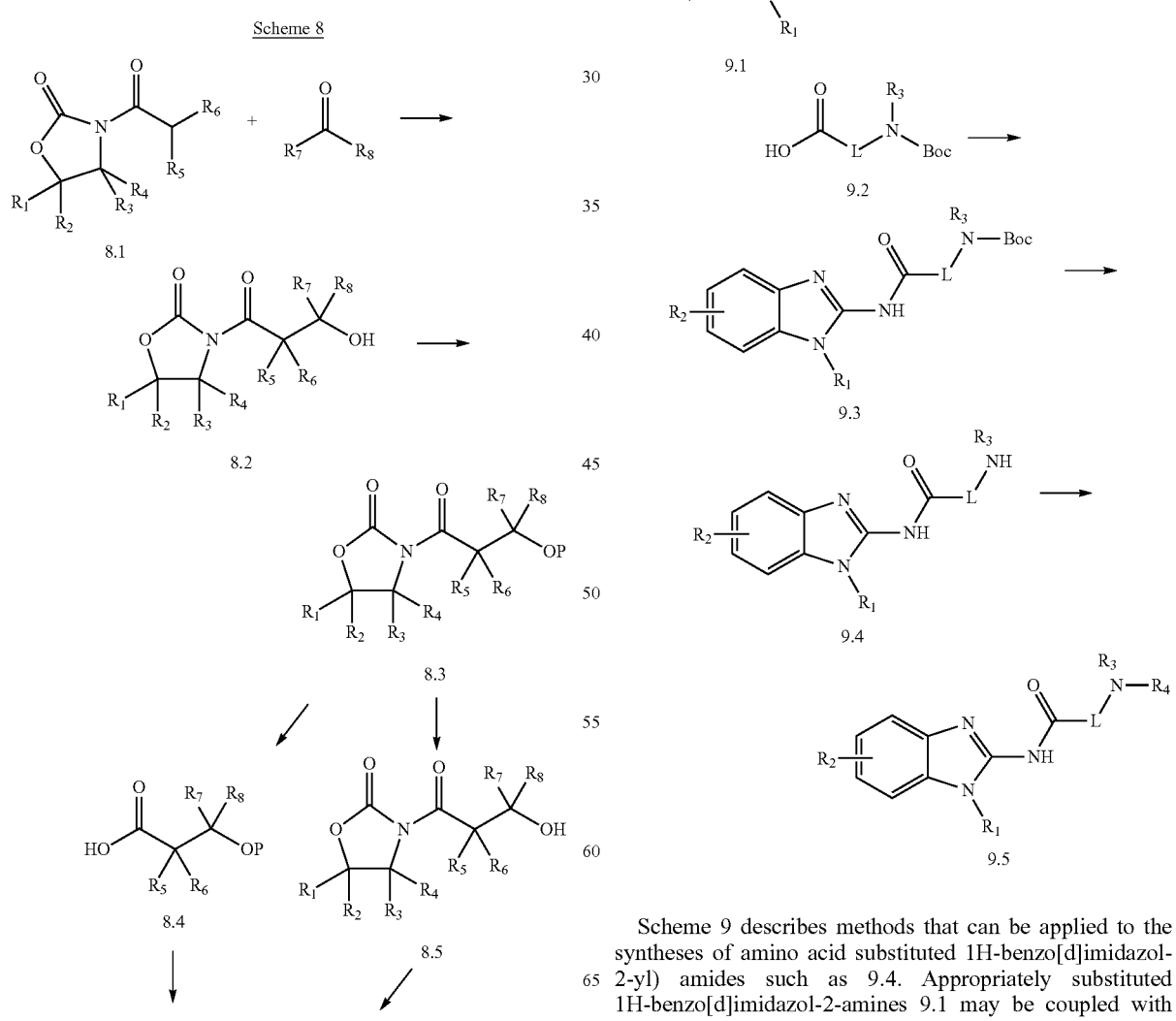

Scheme 8 depicts additional methods for the preparation of optionally substituted 3-hydroxypropanoic acids. An appropriately substituted 3-acetyloxazolidin-2-one 8.1 is reacted with a ketone or aldehyde to afford 3-(3-hydroxypropanoyl)oxazolidin-2-ones 8.2. The hydroxyl group is functionalized with a protecting group to provide diastereomers 8.3 that are separable by silica gel chromatography. Each diastereomer 8.3 is then reacted in a two-step sequence, in either order, of hydroxyl group deprotection and oxazolidinone cleavage to provide 3-hydroxypropanoic acids such as 8.6.

Scheme 9 describes methods that can be applied to the syntheses of amino acid substituted 1H-benzo[d]imidazol-2-yl) amides such as 9.4. Appropriately substituted 1H-benzo[d]imidazol-2-amines 9.1 may be coupled with carbamate-protected amino acid derivatives such as 9.2 to afford the corresponding amides 9.3. The carbamate protecting group can be removed from the amine via one of a number of strongly acidic reagents to afford amines like 9.4. Such secondary amines can then be further functionalized under standard amine alkylation conditions to provide tertiary amine-containing 1H-benzo[d]imidazol-2-yl)amides such as such as 9.5.

Scheme 10

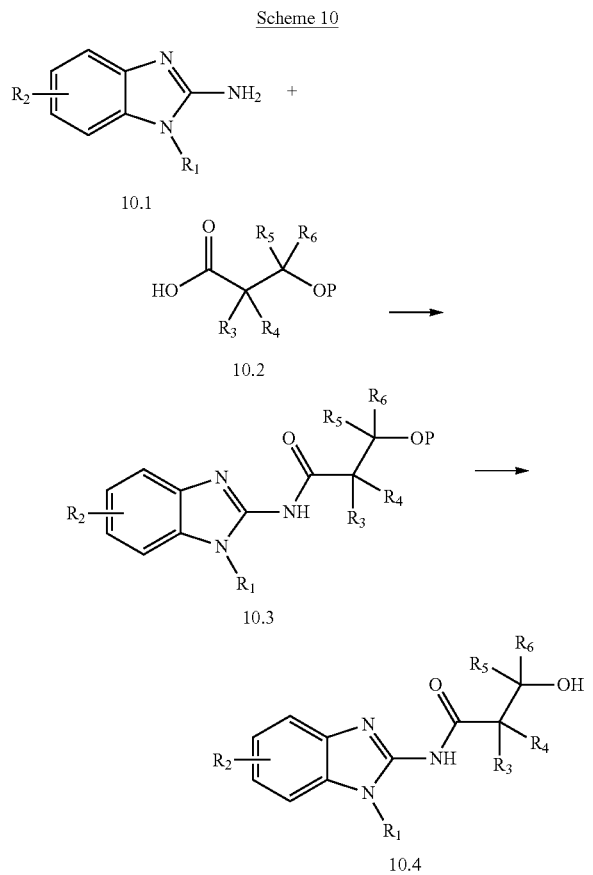

Scheme 10 describes methods that can be employed to prepare 1H-benzo[d]imidazol-2-yl)amides substituted with hydroxyl-containing amides such as 10.4. Appropriately substituted 1H-benzo[d]imidazol-2-amines 10.1 may be coupled with protected alcohol derivatives such as 10.2 to afford the corresponding amides 10.3. The alcohol protecting group can be removed via several methods including tetrabutylammonium fluoride to provide alcohol-containing 1H-benzo[d]imidazol-2-yl) amides such as such as 10.4.

Synthetic Methods
Section 1. Representative Procedures for the Preparation of 1H-benzo[d]imidazol-2-amines Intermediates (Compounds 1.4, Scheme 1).
Method 1:

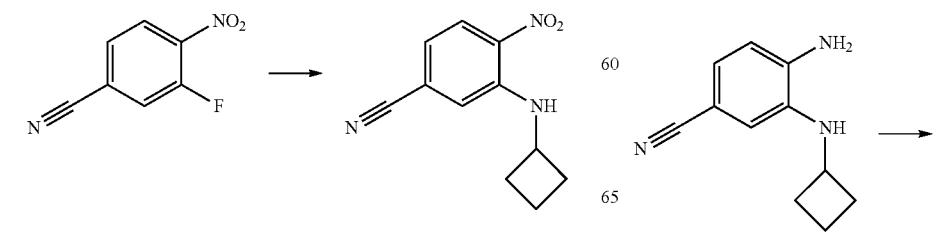

Step A. Preparation of 3-(cyclobutylamino)-4-nitrobenzonitrile. A 500 mL round-bottom flask was charged with of 3-fluoro-4-nitrobenzonitrile (5.00 g, 30.1 mmol) and tetrahydrofuran (100 mL) and placed in a 0° C. bath. After 5 minutes, cyclobutylamine hydrochloric acid (3.60 g, 33.0 mmol) was added in one portion with stirring before the dropwise addition of diisopropylethylamine (15 mL, 82 mmol). The mixture was allowed to stir at 0° C. for 1 hour. The ice bath was removed and the flask was allowed to warm to room temperature and allowed to stir overnight. The bulk of the tetrahydrofuran was removed on a rotary evaporator before the mixture was diluted with EtOAc (200 mL). The organic layer was washed with saturated aqueous ammonium chloride twice, saturated aqueous sodium bicarbonate, and brine and then dried over anhydrous sodium sulfate. The dried solution was filtered and concentrated to give the desired product as a crude orange solid (6.25 g). TLC $R_f$=0.70-0.45 streak in 20% EtOAc in hexanes. MS (ESI) m/z 218.0 (MH$^+$). $^1$H NMR (CDCl$_3$): δ 8.24 (d, J=8.68 Hz, 1H), 8.11 (bs, 1H), 7.01 (d, J=1.48 Hz, 1H), 6.86 (dd, J=8.72, 1.64, 1H), 4.09-4.00 (m, 1H), 2.60-2.51 (m, 2H), 2.11-1.88 (m, 4H).

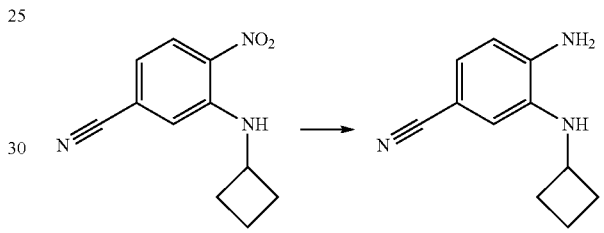

Step B. Preparation of 4-amino-3-(cyclobutylamino) benzonitrile. To a solution of 3-(cyclobutylamino)-4-nitrobenzonitrile (6.50 g, 30.1 mmol) in EtOH (160 mL) was added iron powder (8.8 g, 150 mmol) and a solution of ammonium chloride (8.1 g, 150 mmol) in water (30 mL). The mixture was heated in a sand bath at 90° C. for 16 hours while being exposed to air. The mixture was allowed to cool, diluted with EtOAc (200 mL) and the resulting mixture was filtered through Celite. The Celite was rinsed with saturated aqueous sodium bicarbonate and EtOAc. The combined filtrates were separated and the aqueous layer was extracted with EtOAc. The combined organics were washed with brine, dried with anhydrous sodium sulfate and concentrated to provide the crude title compound (6.2 g). The material was subjected to a 120 g Isco silica gel column (10 to 40% EtOAc in hexanes) to provide the desired product (4.17 g) in a 74% yield for two steps as a pink colored solid. MS (ESI) m/z 188.0 (MH$^+$). $^1$H NMR (CDCl$_3$): δ 7.01 (dd, J=8.00, 1.76 Hz, 1H), 6.73 (d, J=1.72 Hz, 1H), 6.68 (d, J=8.0 Hz, 1H), 3.92-3.85 (m, 1H), 3.65-3.45 (br m, 2H), 2.53-2.44 (m, 2H), 1.88-1.83 (m, 4H).

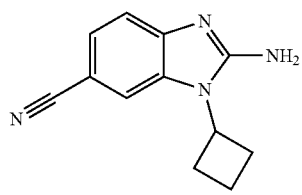

Step C. Preparation of 2-amino-1-cyclobutyl-1H-benzo[d]imidazole-6-carbonitrile. To a solution of 4-amino-3-(cyclobutylamino) benzonitrile (4.0 g, 21.3 mmol) in EtOH (100 mL) was added a solution of cyanogen bromide (3 M in CH$_2$Cl$_2$, 14 mL, 42 mmol. The mixture was stirred at room temperature for 18 hours and then concentrated in vacuo. The residue was partitioned between EtOAc (150 mL) and aqueous Na$_2$CO$_3$ (10%, 100 mL). The aqueous layer was extracted twice with EtOAc. The combined organic layers were washed with brine, dried (Na$_2$SO$_4$) and concentrated to give a pink solid (4.5 g). The solid was subjected to a hexanes and EtOAc trituration to provide the title compound as a pale pink solid (3.1 g, 69%). R$_f$=0.1 streak in 100% EtOAc. MS (ESI) m/z 213.2 (MH$^+$). $^1$H NMR (MeOH-d$_4$): δ 7.78 (s, 1H), 7.38 (d, J=8.28, 1H), 7.28 (d, J=8.20, 1H), 4.92-4.81 (m, 1H), 2.88-2.78 (m, 2H), 2.54-2.45 (m, 2H), 2.08-1.78 (m, 2H). An additional portion of the desired product (1.0 g) was recovered from the trituration solvent and showed to be desired product with >90% purity by $^1$H NMR.

The following 1H-benzo[d]imidazol-2-amines were prepared using the general procedures described in Section 1, Method 1, with appropriate starting materials. Alternative procedures for certain starting materials are described in the Methods 2-5.

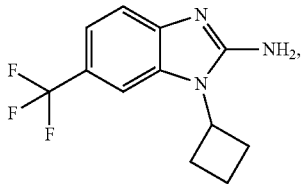

1-cyclobutyl-6-(trifluoromethyl)-1H-benzo[d]imidazol-2-amine

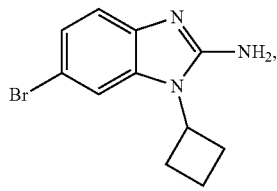

6-bromo-1-cyclobutyl-1H-benzo[d]imidazol-2-amine

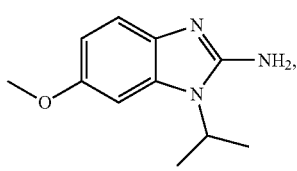

1-isopropyl-6-methoxy-1H-benzo[d]imidazol-2-amine

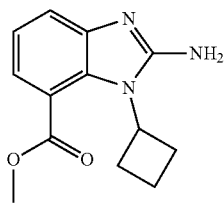

methyl 2-amino-1-cyclobutyl-1H-benzo[d]imidazole-7-carboxylate

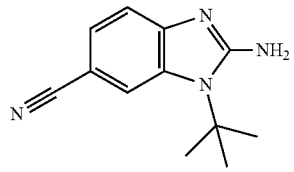

2-amino-1-(tert-butyl)-1H-benzo[d]imidazole-6-carbonitrile

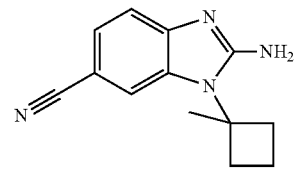

2-amino-1-(1-methylcyclobutyl)-1H-benzo[d]imidazole-6-carbonitrile

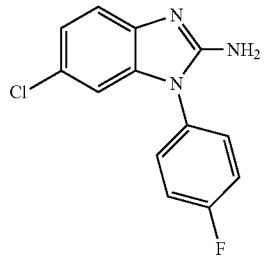

6-chloro-1-(4-fluorophenyl)-1H-benzo[d]imidazol-2-amine

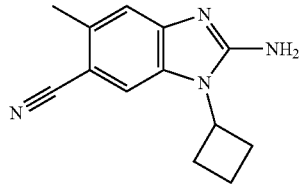

2-amino-1-cyclobutyl-5-methyl-1H-benzo[d]imidazole-6-carbonitrile

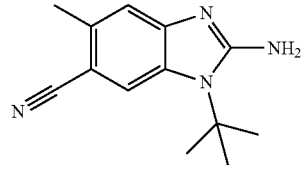

2-amino-1-(tert-butyl)-5-methyl-1H-benzo[d]imidazole-6-carbonitrile

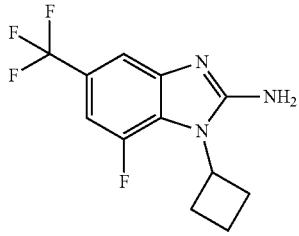

1-cyclobutyl-7-fluoro-5-(trifluoromethyl)-1H-benzo[d]imidazol-2-amine

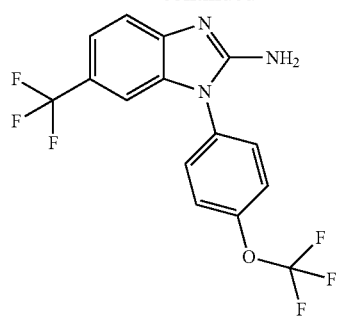

1-(4-(trifluoromethoxy)phenyl)-6-(trifluoromethyl)-1H-benzo[d]imidazol-2-amine

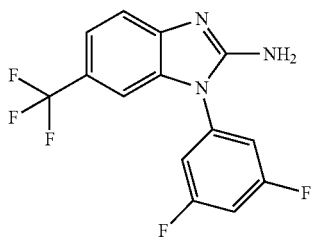

1-(3,5-difluorophenyl)-6-(trifluoromethyl)-1H-benzo[d]imidazol-2-amine

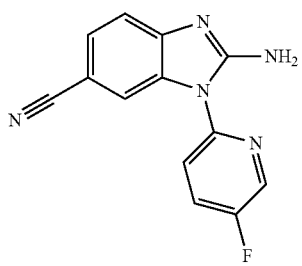

2-amino-1-(5-fluoropyridin-2-yl)-1H-benzo[d]imidazole-6-carbonitrile

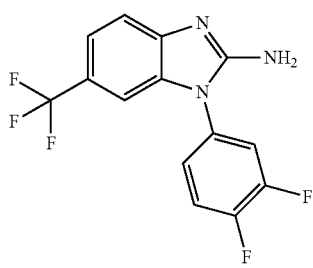

1-(3,4-difluorophenyl)-6-(trifluoromethyl)-1H-benzo[d]imidazol-2-amine

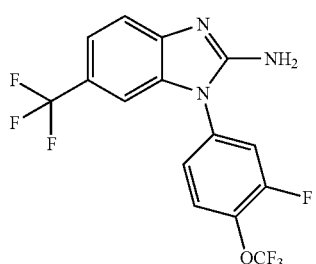

1-(3-fluoro-4-(trifluoromethoxy)phenyl)-6-(trifluoromethyl)-1H-benzo[d]imidazol-2-amine

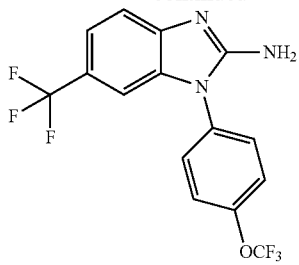

1-(4-(trifluoromethoxy)phenyl)-6-(trifluoromethyl)-1H-benzo[d]imidazol-2-amine

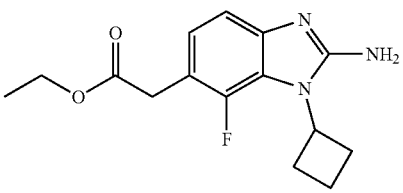

ethyl 2-(2-amino-1-cyclobutyl-7-fluoro-1H-benzo[d]imidazol-6-yl)acetate

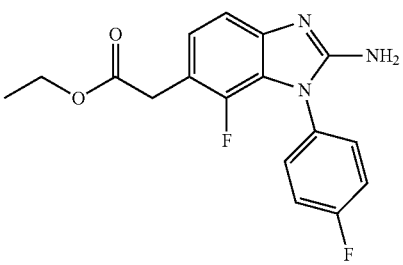

ethyl 2-(2-amino-7-fluoro-1-(4-fluorophenyl)-1H-benzo[d]imidazol-6-yl)acetate

Method 2: Preparation of 3-((4-fluorophenyl)amino)-4-nitrobenzonitrile for Use in Method 1, Step B.

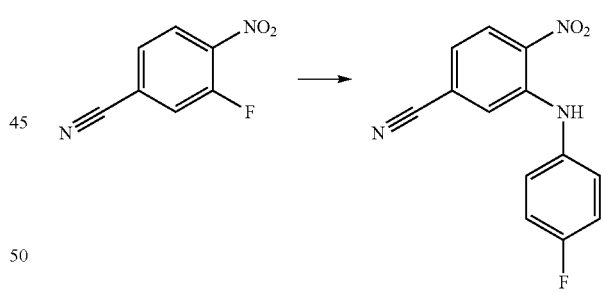

A mixture of 3-fluoro-4-nitrobenzonitrile (2 g, 12 mmol), triethylamine (1.7 mL, 1.5 equivalents) and 4-fluoroaniline (1.7 mL, 1.5 equivalents) was heated at 60° C. under a nitrogen atmosphere for 60 hours. The resulting solid red-brown mass was cooled to ambient temperature and suspended in 50 mL of 1 N aqueous hydrochloric acid. The mixture was extracted extensively with dichloromethane and the organic extracts dried over anhydrous magnesium sulfate. Concentration of the organic extracts under reduced pressure afforded 2.9 g of a red solid, practically pure by LC/MS. MS (ESI) m/z 256 (M-H⁻).

Method 3: Preparation of 5-chloro-N-cyclobutyl-2-nitroaniline for Use in Method 1, Step B.

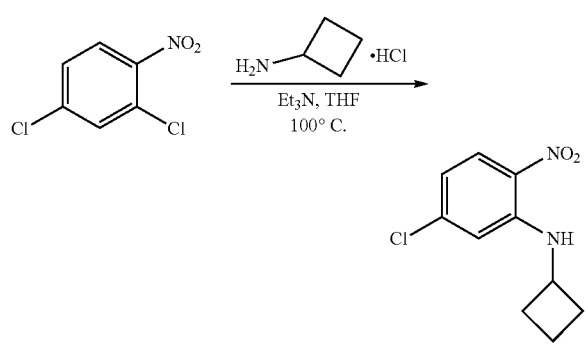

A mixture of cyclobutylamine hydrochloride (2.15 g), triethylamine (2.8 mL), 2,4-dichloro-1-nitrobenzene (3.84 g, 20 mmol, limiting reagent) and tetrahydrofuran (40 mL) was heated in a sealed vial at 100° C. for 16 hours. The reaction mixture was cooled to room temperature, and 0.2 equivalents of both cyclobutylamine hydrochloride and triethylamine added, and the resulting mixture was heated at 100° C. for an additional 17 hours. The cooled reaction mixture was diluted with water, extracted thoroughly with dichloromethane and ethyl acetate, the organic extracts dried over anhydrous magnesium sulfate and concentrated. Purification of the crude product by chromatography on silica with 20% dichloromethane in hexanes as eluent afforded the desired product (1.65 g) as an orange solid. $^1$H NMR (CDCl$_3$): δ 8.16 (NH, bs), 8.12 (1H, d), 6.70 (1H, s), 6.60 (1H, d), 4.02 (1H, m), 2.53 (2H, m), 2.03 (2H, m), 1.92 (2H, m).

Method 4: Preparation of 3-Methyl-N-(2-nitro-5-(trifluoromethyl)phenyl)isoxazol-5-amine for Use in Method 5.

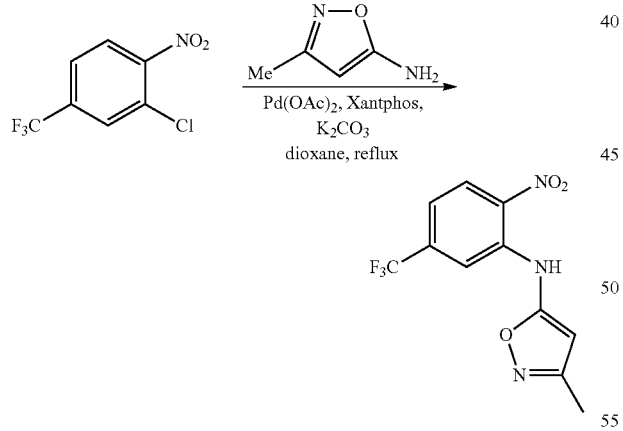

Palladium(II) acetate (1.00 g, 0.443 mmol) was added to Xantphos (0.513 g, 0.887 mmol) in degassed dioxane (10 mL) and the suspension was stirred for 15 minutes under N$_2$. The resulting solution was added to a mixture of 2-chloro-3-nitro-6-(trifluoromethyl)benzene (1.00 g, 4.43 mmol), 3-methylisoxazol-5-amine (0.522 g, 5.32 mmol) and K$_2$CO$_3$ (0.919 g, 6.65 mmol) in degassed dioxane (40 mL) and the reaction mixture was refluxed overnight. Conversion was confirmed by TLC and the solution was filtered through a plug of celite. The volatiles were removed and the crude residue was purified by chromatography on silica (0-100% EtOAc/hexanes) to give 0.811 g (63%) of the title compound. MS (ESI) m/z 288 (MH$^+$).

The following intermediates were prepared for use in Method 1, Step B using the general procedure described in Section 1, Method 4, with appropriate starting materials.

3-((5-fluoropyridin-2-yl)amino)-4-nitrobenzonitrile

N-(3,5-difluorophenyl)-2-nitro-5-(trifluoromethyl)aniline

N-(3-fluoro-4-(trifluoromethoxy)phenyl)-2-nitro-5-(trifluoromethyl)aniline 2-nitro-N-(4-(trifluoromethoxy)phenyl)-5-(trifluoromethyl)aniline N-(3,4-difluorophenyl)-2-nitro-5-(trifluoromethyl)aniline Method 5: Preparation of N$^1$-(3-methylisoxazol-5-yl)-5-(trifluoromethyl)benzene-1,2-diamine for Use in Method 1, Step C.

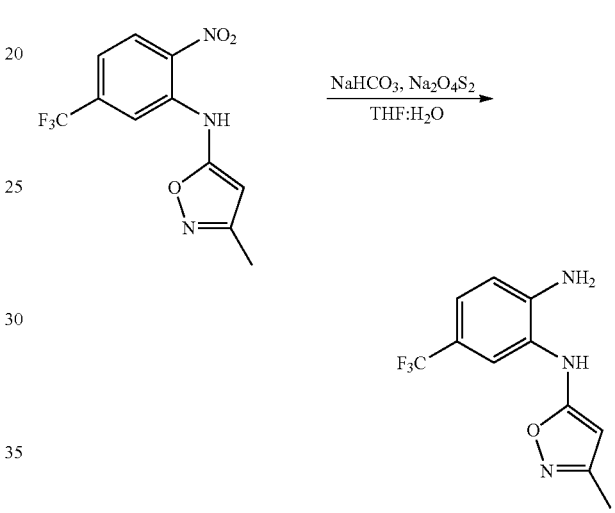

Sodium bicarbonate (0.410 g, 4.88 mmol) then sodium hydrosulfite (1.27 g, 7.31 mmol) were added to a solution of the nitro aromatic core (0.700 g, 2.44 mmol) in tetrahydrofuran:H$_2$O (2:1; 24 mL). The resulting reaction mixture was allowed to stir for 4 hours, diluted with H$_2$O and then extracted with EtOAc. The combined organics were dried (MgSO$_4$) and the volatiles removed to leave a crude residue that was purified by chromatography on silica (0-5% MeOH/dichloromethane) to give 380 mg (61%) of the title compound. MS (ESI) m/z 258 (MH$^+$).

The following benzene-1,2-diamine was prepared using the general procedures described in Section 1, Methods 4 and 5, with appropriate starting materials, for use in Method 1, Step C:

4-amino-3-((3-methylisoxazol-5-yl)amino)benzonitrile

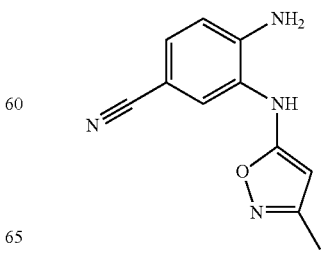

Method 6: Preparation of ethyl 2-amino-1-cyclobutyl-1H-benzo[d]imidazole-6-carboxylate.

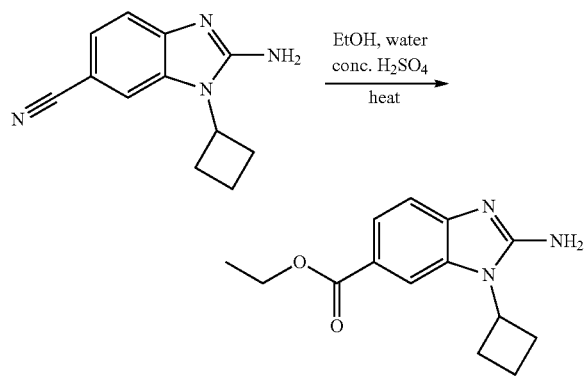

To a solution of 4-amino-3-(cyclobutylamino) benzonitrile (1.5 g, 7.0 mmol) in EtOH (30 mL) was added water (3 mL) and concentrated sulfuric acid (3 mL). The solution was placed in a 150° C. sand bath with stirring for 4 days. The reaction was allowed to cool to ambient temperature and carefully quenched by pouring slowly into saturated aqueous sodium bicarbonate. The mixture was diluted with EtOAc and the layers were separated. The aqueous layer was back extracted with dichloromethane and the combined organic layers were washed with brine, dried with sodium sulfate, filtered and concentrated to give the title compound as a tan solid (790 mg, 43% yield). MS (ESI) m/z 260.0 (MH+), retention time=2.21 min (Method B).

Section 2. Representative Procedures for the Preparation of 1H-benzo[d]imidazol-2-yl amides (1.5, Scheme 1).

Method 7: General Procedure for Amide Formation Using HATU (1-((dimethylamino)(dimethyliminio)methyl)-1H-benzo[d][1,2,3]triazole 3-oxide hexafluorophosphate(V)) as Coupling Reagent.

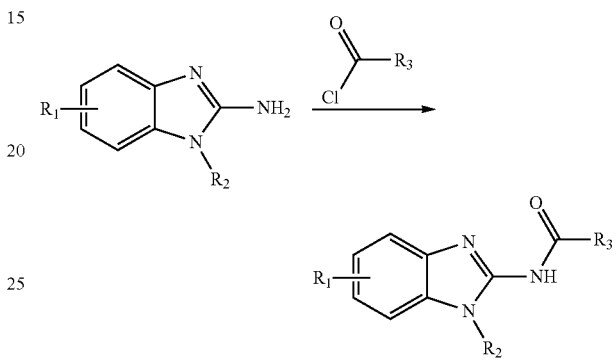

The appropriate carboxylic acid was dissolved in dimethyformamide or THF (0.20-0.7 M) and diisopropylethylamine or pyridine (2 equivalents) was added prior to the addition of 1-((dimethylamino)(dimethyliminio)methyl)-1H-benzo[d][1,2,3]triazole 3-oxide hexafluorophosphate(V) (HATU, 1.2 equivalents) in one portion. The reaction was allowed to stir at room temperature for 0 to 15 minutes prior to the addition of the required substituted 2-aminobenzimidazole (1 equivalent) and the flask was placed in a heated sand bath (40-65° C.) for 8 to 48 hours. The mixture was diluted with EtOAc and washed sequentially with saturated aqueous NH$_4$Cl (2×), saturated aqueous NaHCO$_3$ (2×), 10% aqueous Na$_2$CO$_3$ (2×), and brine. The organic layer was dried over Na$_2$SO$_4$ and concentrated. Purification by chromatography on silica (0-100% EtOAc/hexanes or 0-10% MeOH/dichloromethane) provided the title corresponding 1H-benzo[d]imidazol-2-yl amides.

Method 8: General Procedure for Amide Formation Using Acyl Chlorides

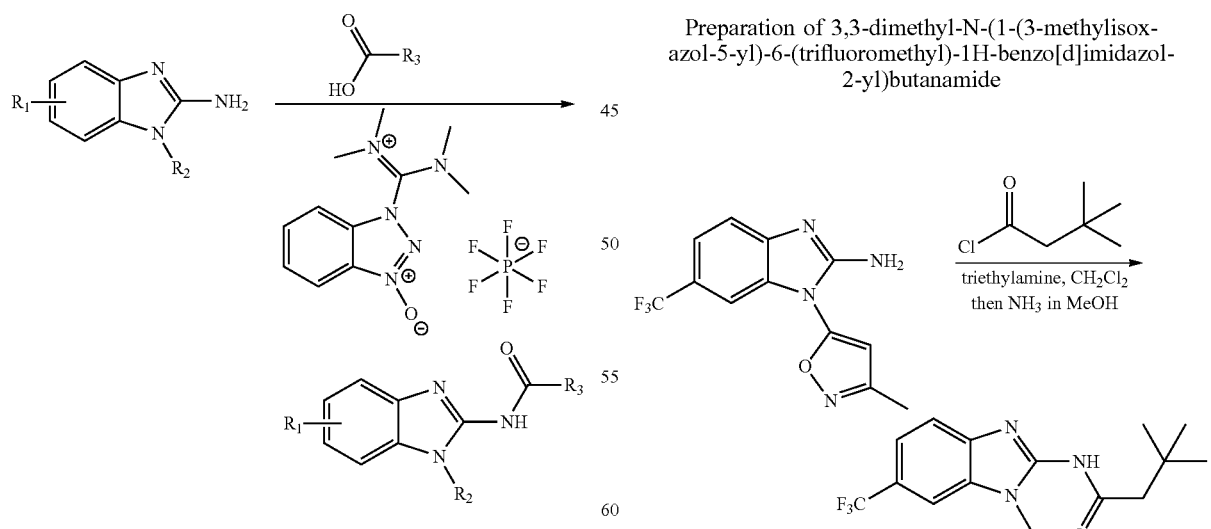

To a solution appropriate 1H-benzo[d]imidazol-2-amine intermediate (0.22 mmol) in tetrahydrofuran (1 mL) was added pyridine (1.5 equivalents) and acyl chloride (1.2 equivalents). The reaction mixture was stirred for 18 hours. The mixture was partitioned between EtOAc and water. The organic layer was dried (Na$_2$SO$_4$) and concentrated. The residue was purified by chromatography on silica (0-100% EtOAc/hexanes) to provide title compounds.

Method 9: General Procedure for Amide Coupling Using Excess Acid Chloride Followed by Treatment with Ammonia.

Example 46

Preparation of 3,3-dimethyl-N-(1-(3-methylisoxazol-5-yl)-6-(trifluoromethyl)-1H-benzo[d]imidazol-2-yl)butanamide 3,3-Dimethylbutanoyl chloride (0.187 mL, 1.04 mmol) was added dropwise to a 0° C. solution of 1-(3-methylisoxazol-5-yl)-6-(trifluoromethyl)-1H-benzo[d]imidazol-2-amine (0.030 g, 0.104 mmol) and triethylamine (0.180 mL, 1.56 mmol) in CH$_2$Cl$_2$ (1 mL) and the reaction mixture was allowed to warm to ambient temperature and stir for 30 minutes. Ammonia (2.0 M in MeOH, 1 mL) was added and the mixture was stirred at 50° C. for two hours before quenching with saturated aqueous NH$_4$Cl. The aqueous portion was extracted with EtOAc, the combined organics were dried (MgSO$_4$) and the volatiles removed to give a crude residue that was purified by chromatography on silica (0-5% MeOH/DCM) to yield 0.017 g (43%) of the title compound. MS (ESI) m/z 381 (MH$^+$).

Method 10: General Procedure for Amide Formation Using EDC (1-Ethyl-3-(3-dimethylaminopropyl)carbodiimide hydrochloride) and HOBt (1-hydroxybenzotriazole) as Coupling Reagents.

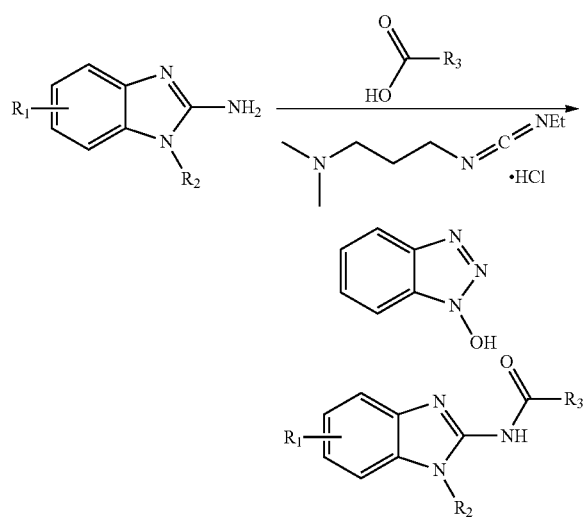

A solution of the appropriate 1H-benzo[d]imidazol-2-amine (0.13 mmol), carboxylic acid (0.16 mmol), EDC (0.19 mmol), HOBt (0.19 mmol) and diisopropylethylamine (0.66 mmol) in tetrahydrofuran (1 mL) was heated at 50° C. under nitrogen for 2-4 hours. The reaction was cooled to room temperature, diluted with EtOAc and washed with water. The organic solution was concentrated in vacuo and purified by flash column chromatography (silica gel, 0-10% MeOH/DCM) to afford the title compounds.

Method 11: Representative Procedure for Amide Formation Using Yamaguchi Conditions.

Example 45

Preparation of (S)-2,2-Dimethyl-N-(1-(3-methylisoxazol-5-yl)-6-(trifluoromethyl)-1H-benzo[d]imidazol-2-yl)cyclopropanecarboxamide

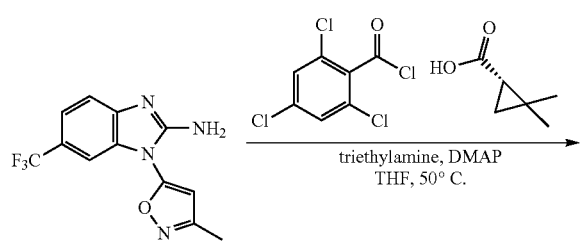

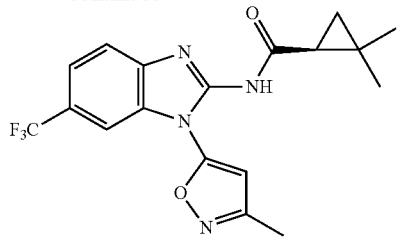

(S)-2,2-Dimethylcyclopropyl carboxylic acid (0.018 g, 0.159 mmol), triethylamine (0.042 mL, 0.318 mmol) and 2,4,6-trichlorobenzoyl chloride (0.025 mL, 0.159 mmol) was stirred in 1 mL tetrahydrofuran for 30 minutes. 1-(3-Methylisoxazol-5-yl)-6-(trifluoromethyl)-1H-benzo[d]imidazol-2-amine (0.030 g, 0.106 mmol) and 4-(dimethylamino)pyridine (0.003 g, 0.026 mmol) were added to the reaction mixture and the resulting solution was heated to 50° C. and stirred overnight. The reaction was quenched with H$_2$O, extracted (EtOAc 3×) and the combined organics were dried (MgSO$_4$) and the volatiles removed to give a crude product that was purified by chromatography on silica (0-100% EtOAc/hexanes) followed by HPLC (0-100% MeCN/H$_2$O) to yield 21 mg (71%) of the desired product. MS (ESI) m/z 379 (MH$^+$).

Method 12: General Procedure for Amide Formation Using Acylbenzotriazoles.

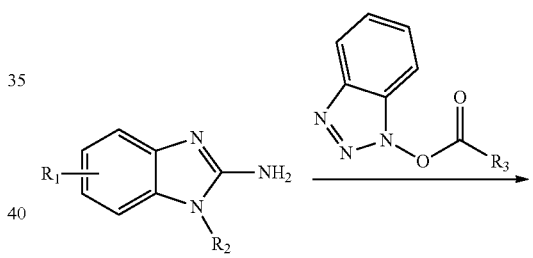

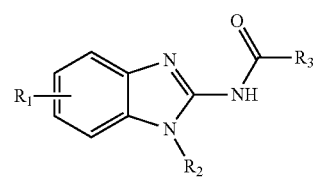

A solution of appropriate 1H-benzo[d]imidazol-2-amine intermediate (0.66 mmol) and triethylamine (0.5 mL, 3.3 mmol, 5 equivalents) in tetrahydrofuran (3 mL) was stirred for 5 min at room temperature. To this solution was added a solution of an appropriate acylbenzotriazole (0.7 M in dichloromethane, 3.0 mL, 2.0 mmol, 3 equivalents; see Katritzky, A R, et al, *Synlett*, 2005, 11, 1656) and the mixture was placed in a 50° C. sand bath for 12 hours. The mixture was allowed to cool to room temperature and diluted with EtOAc (50 mL) and washed sequentially with saturated aqueous Na$_2$CO$_3$ (three times) and brine. The organic layer was dried over Na$_2$SO$_4$ and concentrated. Purification by chromatography on silica (0-100% EtOAc/hexane or 0-10% MeOH/dichloromethane) provided the title compounds.

Section 3. Exemplary Syntheses for Examples in Table 1 Involving Further Transformation of 1H-benzo[d]imidazol-2-yl amides.

Example 51

Preparation of N-(1-cyclobutyl-6-(hydroxymethyl)-1H-benzo[d]imidazol-2-yl)-3,3-dimethylbutanamide

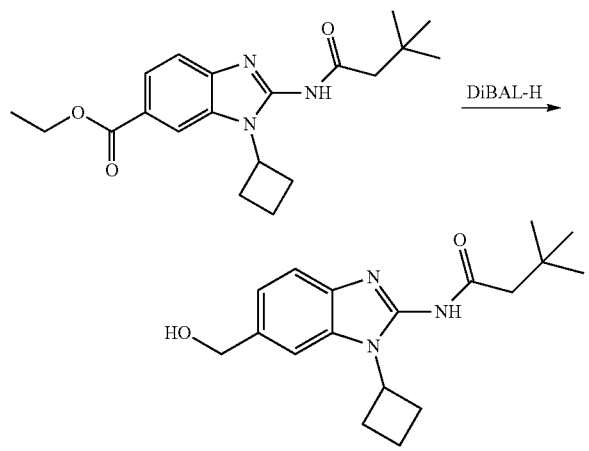

A CH$_2$Cl$_2$ (15 mL) solution of ethyl 1-cyclobutyl-2-(3,3-dimethylbutanamido)-1H-benzo[d]imidazole-6-carboxylate (112 mg) was placed in a −78° C. bath for 10 minutes prior to the dropwise addition of diisobutylaluminum hydride (1.0 M in CH$_2$Cl$_2$, 2 mL). The reaction was allowed to stir at −78° C. for 1 h before being quenched by the dropwise addition of MeOH (2 mL). The quenched reaction was diluted with CH$_2$Cl$_2$ (50 mL) and sodium/potassium tartrate (1 M, 50 mL) was added and the mixture was allowed to vigorously stir overnight. In this time frame, two clear layers developed and the aqueous portion was extracted with CH$_2$Cl$_2$ (2×), the combined organics were washed with brine, dried (Na$_2$SO$_4$) and the volatiles removed to give a crude residue that was purified via chromatography (Isco 12 g silica gel column, 0-10% MeOH/CH$_2$Cl$_2$) to yield 56 mg (57%) of the title compound. MS (ESI) m/z 316.4 (MH$^+$), retention time=2.35 min. The material was further purified by subjecting to another Isco 12 g silica gel column (40 to 100% EtOAc in hexanes) to give 10 mg of the title compound.

Example 53

Preparation of N-(1-cyclobutyl-6-(2-hydroxypropan-2-yl)-1H-benzo[d]imidazol-2-yl)-3,3-dimethylbutanamide

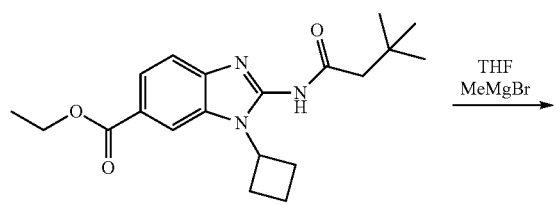

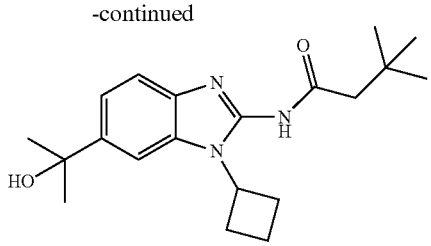

A tetrahydrofuran (2 mL) solution of ethyl 1-cyclobutyl-2-(3,3-dimethylbutanamido)-1H-benzo[d]imidazole-6-carboxylate (50 mg, 0.14 mmol) was allowed to chill at 0° C. for 10 minutes under nitrogen prior to the dropwise addition of methylmagnesium bromide (2 M in ether, 0.3 mL). The reaction was allowed to stir at 0° C. for 1.5 hours and then quenched by the addition of saturated sodium bicarbonate (25 mL) and EtOAc (25 mL). The aqueous layer was extracted twice with EtOAc and the combined organics were washed with brine, dried with sodium sulfate, filtered and concentrated to give a crude residue. The crude material was subjected to column chromatography (two 4 g silica gel Isco columns in series, 5 to 50% EtOAc in hexanes) to give the title compound as a white solid (16 mg, 33% yield). MS (ESI) m/z 344.4 (MH$^+$), retention time=2.44 minutes (Method B).

Example 57

Preparation of N-(1-cyclobutyl-6-(1-hydroxyethyl)-1H-benzo[d]imidazol-2-yl)-3,3-dimethylbutanamide

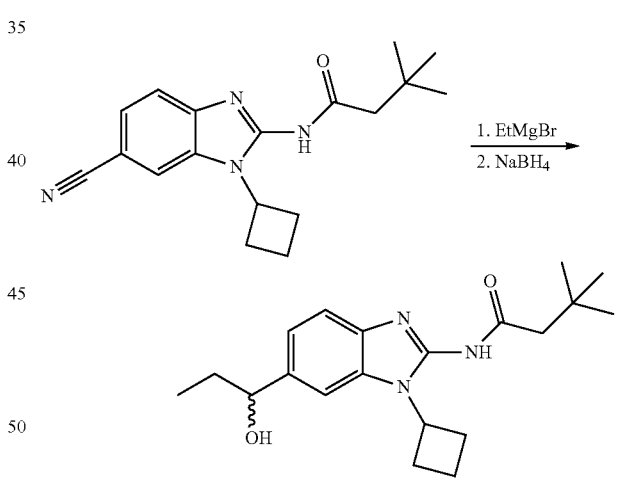

Step A. A tetrahydrofuran (2 mL) solution of N-(6-cyano-1-cyclobutyl-1H-benzo[d]imidazol-2-yl)-3,3-dimethylbutanamide (112 mg) was placed in a 0° C. bath for 10 minutes prior to the dropwise addition of ethylmagnesium bromide (3 M in diethyl ether, 0.45 mL). The reaction was allowed to stir at 0° C. for 1 h and then allowed to warm up to room temperature. The reaction was allowed to stir at room temperature overnight and then placed back in a 0° C. bath for 10 minutes before it was quenched with MeOH (0.5 mL). After 5 minutes, the quenched reaction was partioned between saturated aqueous ammonium chloride (25 mL) and ethyl acetate (25 mL). The aqueous layer was extracted twice with ethyl acetate. The combined organics were washed with brine and dried with sodium sulfate. The dried reaction was filtered, concentrated and subjected to a 12 g silica gel Isco column (15 to 100% EtOAc in hexanes) to give the ethyl ketone compound N-(1-cyclobutyl-6-propionyl-1H-benzo[d]imidazol-2-yl)-3,3-dimethylbutanamide (75 mg, 70%) as a white solid. MS (ESI) m/z 342.4 (MH$^+$), retention time=3.51 minutes (Method B).

Step B. N-(1-Cyclobutyl-6-propionyl-1H-benzo[d]imidazol-2-yl)-3,3-dimethylbutanamide (41 mg) was placed in a roundbottom flask with ethanol (6 mL) and the flask was allowed to chill in a 0° C. bath for 10 minutes before the portionwise addition of sodium borohydride (60 mg). The reaction was allowed to stir for 30 minutes and then quenched by the slow addition of HCl (1.0 M, 10 mL). The quenched reaction was diluted with EtOAc (30 mL) and allowed to stir for 1 hour. The aqueous layer was extracted with EtOAc (2×). The combined organics were washed with saturated aqueous sodium bicarbonate (40 mL), brine and dried with sodium sulfate. The dried solution was filtered and concentrated to give a crude material that was subjected to a 12 gram silica gel Isco column (20-50% EtOAc in hexanes) to give the title compound (25 mg, 60%) as a white solid. MS (ESI) m/z 344.4 (MH$^+$), retention time=2.57 minutes (Method B).

Example 65

Preparation of (S)—N-(1-cyclobutyl-6-isopropyl-1H-benzo[d]imidazol-2-yl)-2,3-dimethylbutanamide

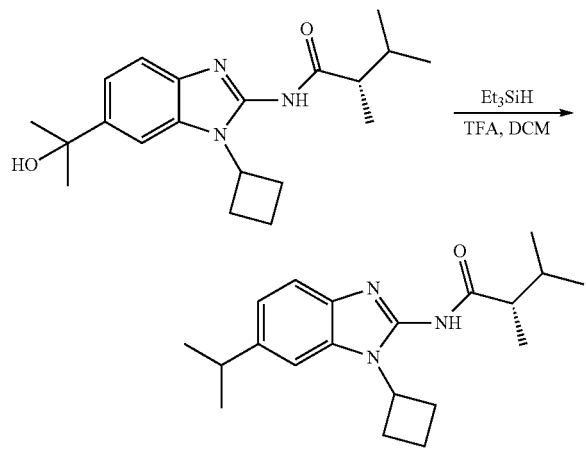

Solid (S)—N-(1-cyclobutyl-6-(2-hydroxypropan-2-yl)-1H-benzo[d]imidazol-2-yl)-2,3-dimethylbutanamide (15 mL) was dissolved in dichloromethane (2 mL). TFA (1.5 mL) was added before the dropwise addition of neat triethylsilane (1 mL). The reaction was allowed to stir overnight and then diluted with dichloromethane (15 mL) and washed with saturated sodium bicarbonate (20 mL). The aqueous layer was extracted twice with dichloromethane. The combined organics were washed with brine and dried with sodium sulfate. The dried solution was filtered and concentrated to give a crude product. The crude material was subjected to a high vacuum for 48 h prior to being subjected to column chromatography (4 gram Isco silica gel, 0-5% MeOH in dichloromethane) to give the title compound as a colorless oil (9 mg, 63% yield). MS (ESI) m/z 328.4 (MH$^+$), retention time=3.36 min (Method B).

Example 66

Preparation of N-(1-cyclobutyl-6-(difluoromethyl)-1H-benzo[d]imidazol-2-yl)-3,3-dimethylbutanamide

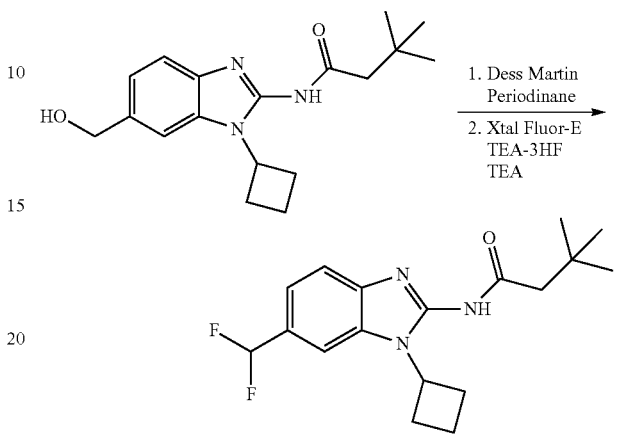

Step A. Solid N-(1-cyclobutyl-6-(hydroxymethyl)-1H-benzo[d]imidazol-2-yl)-3,3-dimethylbutanamide (100 mg) was dissolved in dichloromethane (5 mL) and solid sodium bicarbonate (106 mg, 4 equivalents) was added in one portion before the addition of Dess-Martin periodinane (270 mg, 2 equivalents) in one portion. The reaction turned from colorless to a red colored solution upon the addition of the Dess Martin reagent. The reaction was allowed to stir at room temperature for 1 hour before sodium thiosulfate (10%, 25 mL) and EtOAc (25 mL) were added to quench the reaction. The quenched reaction was allowed to stir for 1 hour and in this time the red colored solution faded to a colorless solution. The aqueous layer was extracted twice with EtOAc. The combined organic phases were washed with sodium bicarbonate, brine, and dried with sodium sulfate. The dried solution was filtered and concentrated to give a crude product which was subjected to column chromatography (12 gram Isco, 5 to 75% EtOAc in hexanes) to yield 83 mg (84%) of N-(1-cyclobutyl-6-formyl-1H-benzo[d]imidazol-2-yl)-3,3-dimethylbutanamide that was used directly in the next reaction.

Step B. The freshly prepared aldehyde (N-(1-cyclobutyl-6-formyl-1H-benzo[d]imidazol-2-yl)-3,3-dimethylbutanamide, 37 mg, 0.118 mmol) from the above experimental was dissolved in dichloromethane (2 mL) and TEA-3HF (58 mg, 3 equivalents) was added before the portionwise addition of XtalFluor-E (81 mg, 3 equivalents) at room temperature. LC/MS analysis at 3 hours of reaction time showed slow progression of the reaction. Therefore, two more equivalents of each reagent were added to the reaction. LC/MS analysis 4 hours later showed slow and clean conversion to the desired product. The reaction was allowed to stir overnight and then quenched by the addition of saturated sodium bicarbonate (20 mL) and diluted with dichloromethane (20 mL). The quenched reaction was allowed to stir for 15 minutes and then extracted with dichloromethane (3×) and the combined organics were washed with brine, dried with sodium sulfate, filtered and concentrated to give a crude material. The crude material was subjected to silica gel chromatography (12 gram Isco, 0-25% EtOAc in hexanes, product is higher in R$_f$ than the corresponding aldehyde) to give the titled compound (7.5 mg, 19% yield) as a white solid. MS (ESI) m/z 336.4 (MH+), retention time=3.37 min (Method B). The intermediate aldehyde was also recovered from the chromatography (16 mg, 43%). (See: Couturier, M. et al, J. Org. Chem. 2010, 75, 3401-3411).

Example 1

Preparation of N-(1-cyclobutyl-1H-benzo[d]imidazol-2-yl)-3,3-dimethylbutanamide

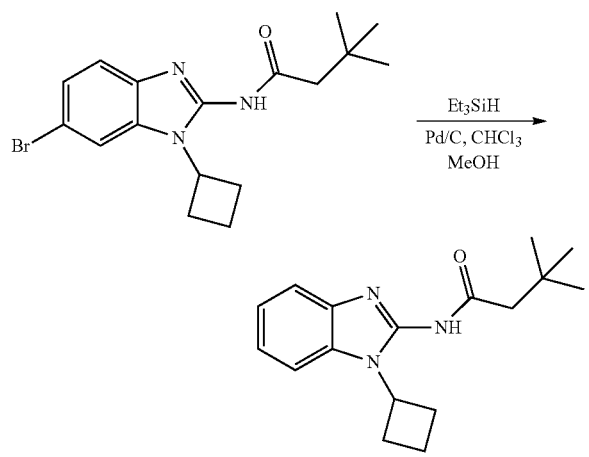

Solid N-(6-bromo-1-cyclobutyl-1H-benzo[d]imidazol-2-yl)-3,3-dimethylbutanamide (75 mg) was dissolved in chloroform (9 mL) and methanol (3 mL) before the addition of palladium on carbon (10%, 30 mg). The mixture was allowed to stir for 2 minutes before the dropwise addition of triethylsilane (0.9 mL). The reaction was allowed to stir for 30 minutes and then passed though filter paper. The filtrate was concentrated and subjected to silica gel chromatography (12 gram Isco column, 0 to 70% EtOAc in hexanes) to give the desired product that contained an impurity. The material was further purified by subjecting it to another silica gel column (4 gram silica gel Isco, 0-10% MeOH in dichloromethane) to give a pure sample of the titled compound (22 mg, 31% yield) as a foamy white solid. MS (ESI) m/z 286.4 (MH+), retention time=2.71 min (Method B). (see Mandal, P K, McMurray, J S, J. Org. Chem. 2007, 72, 6599-6601).

Example 22

Preparation of (R)—N-(6-cyano-1-cyclobutyl-1H-benzo[d]imidazol-2-yl)-2-(methyl(2,2,2-trifluoroethyl)amino)propanamide

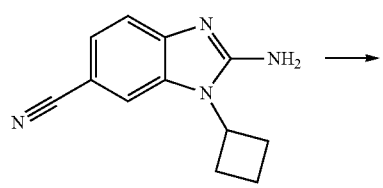

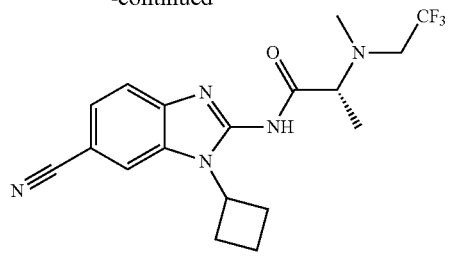

Step A: Preparation of (R)-tert-butyl (1-((6-cyano-1-cyclobutyl-1H-benzo[d]imidazol-2-yl)amino)-1-oxopropan-2-yl)(methyl)carbamate 2-Amino-3-cyclobutyl-3H-imidazo[4,5-b]pyridine-5-carbonitrile (100 mg, 0.47 mmol) and (R)-2-((tert-butoxycarbonyl)(methyl)amino)propanoic acid (115 mg, 0.57 mmol) were used following Method 7 to provide the desired product (112 mg, 59%).

Step B: Preparation of (R)—N-(6-cyano-1-cyclobutyl-1H-benzo[d]imidazol-2-yl)-2-(methylamino)propanamide hydrochloride To a solution of (R)-tert-butyl (1-((6-cyano-1-cyclobutyl-1H-benzo[d]imidazol-2-yl)amino)-1-oxopropan-2-yl)(methyl)carbamate (112 mg, 0.30 mmol) from Step A in MeOH (4 mL) was added concentrated aqueous hydrochloric acid (3 mL) at room temperature. The mixture was stirred for one hour and then concentrated in vacuo. The residue was concentrated twice from methanol to provide the desired product (98 mg, 99%).

Step C: Preparation of (R)—N-(6-cyano-1-cyclobutyl-1H-benzo[d]imidazol-2-yl)-2-(methyl(2,2,2-trifluoroethyl)amino)propanamide DIEA (130 µL, 0.76 mmol) was added to a room temperature solution of (R)—N-(6-cyano-1-cyclobutyl-1H-benzo[d]imidazol-2-yl)-2-(methylamino)propanamide hydrochloride from Step B in dimethyformamide (2 mL). The mixture was stirred for several minutes and then was treated with 2,2,2-trifluoroethyl trifluoromethanesulfonate (55 µL, 0.38 mmol). The mixture was stirred for eight hours with additional DIEA (130 µL, 0.76 mmol) and 2,2,2-trifluoroethyl trifluoromethanesulfonate (55 µL, 0.38 mmol) being added at two hour intervals over the duration of the reaction. The mixture was concentrated in vacuo and purified by silica gel chromatography (10-50% EtOAc/hexanes) to provide the title compound (24 mg, 21%). MS (ESI) m/z 380.4 (MH+).

Example 24

Preparation of N-(6-cyano-1-cyclobutyl-1H-benzo[d]imidazol-2-yl)-3-(dimethylamino)-4,4,4-trifluorobutanamide

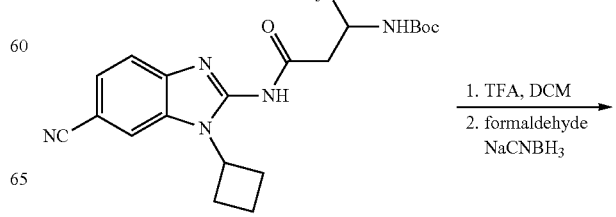

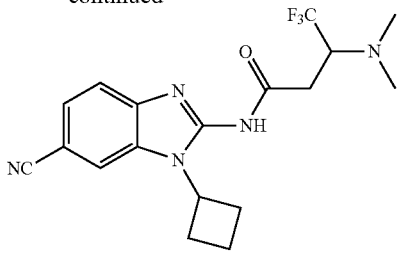

To tert-butyl (4-((6-cyano-1-cyclobutyl-1H-benzo[d]imidazol-2-yl)amino)-1,1,1-trifluoro-4-oxobutan-2-yl)carbamate (23 mg, 0.051 mmol, prepared according to the procedure of Method 7 using 3-((tert-butoxycarbonyl)amino)-4,4,4-trifluorobutanoic acid) in $CH_2Cl_2$ (1 mL) was added $CF_3CO_2H$ (1 mL) and the mixture was stirred at room temperature for 1 hour. Solvents were removed by rotary evaporation, the residue was dissolved in EtOAc, washed sequentially with saturated $NaHCO_3$, brine, then dried ($Na_2SO_4$), filtered and concentrated to give 3-amino-N-(6-cyano-1-cyclobutyl-1H-benzo[d]imidazol-2-yl)-4,4,4-trifluorobutanamide (18 mg, 0.051 mmol) as a colorless oil. This material was dissolved in 20:1 $CH_3OH$/HOAc (0.5 mL) followed by $Et_3N$ (9 µL, 0.10 mmol) and formaldehyde solution (37% in $H_2O$, 12 µL, 0.23 mmol). $NaCNBH_3$ (18 mg, 0.51 mmol) was added and the mixture was stirred at room temperature for 4 hours. Solvent was concentrated by rotary evaporation, the residue was distributed between saturated aqueous $NaHCO_3$ and EtOAc and the layers were separated. The aqueous layer was extracted with EtOAc, the extracts were combined, dried ($Na_2SO_4$), filtered and concentrated. Purification was run on a 4 g silica gel column eluting with 0-50% EtOAc/hexanes to give the title compound (11.8 mg, 61%). MS (ESI) m/z 380.4 ($MH^+$).

Section 4. Exemplary syntheses for Examples in Table 1 involving preparation of branched chiral 1H-benzo[d]imidazol-2-yl amides Example 18

Preparation of (2S,3R)-N-(6-cyano-1-cyclobutyl-1H-benzo[d]imidazol-2-yl)-3-hydroxy-2-methyl-3-phenylbutanamide

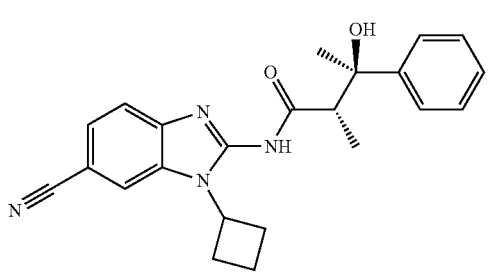 [SMILES: C[C@H](C(=O)Nc1nc2ccc(C#N)cc2n1C1CCC1)[C@@](C)(O)c1ccccc1]

Step A: Preparation of (2S,3R)-3-hydroxy-2-methyl-3-phenylbutanoic acid. A solution of (R)-4-benzyl-3-propionyloxazolidin-2-one (1.0 g, 4.3 mmol) in tetrahydrofuran (10 mL) was added dropwise to a -78° C. solution of LiN(TMS)$_2$ (1.0 M in tetrahydrofuran, 4.5 mL, 4.5 mmol) in tetrahydrofuran (14 mL). The mixture was stirred for 30 minutes at -78° C. and then acetophenone (0.53 mL, 4.5 mmol) was added over 10 minutes. The -78° C. mixture was stirred for two hours and then quenched via the addition of saturated aqueous $NH_4Cl$. The mixture was warmed to room temperature and extracted twice with EtOAc. The combined organics were dried over anhydrous $Na_2SO_4$ and concentrated. The residue was purified by silica gel chromatography (0-20% EtOAc/hexanes) to provide partially separated mixtures of the oxazolidinone starting material and four possible diastereomers ($R_f$=0.57 in 1:4 EtOAc/hexanes, 0.56 g, 37%, (2S,3S) containing fraction; $R_f$=0.50 in 1:4 EtOAc/hexanes, 0.26 g, 17%, (2S,3R) containing fraction). Stereochemical assignment for the observed two major diastereomers were made via extrapolation from data reported in Bartroli, et al; *J. Org. Chem.*, 1995, 60, 3000.

Step B: Preparation of (R)-4-benzyl-3-((2S,3R)-3-((tert-butyldimethylsilyl)oxy)-2-methyl-3-phenylbutanoyl)oxazolidin-2-one. tert-Butyldimethylsilyl trifluoromethanesulfonate (200 µL, 0.88 mmol) was added dropwise to a solution of the diastereomeric mixture containing (2S,3R)-3-hydroxy-2-methyl-3-phenylbutanoic acid isolated from Step A (0.26 g, 0.74 mmol) and $Et_3N$ (200 µL, 1.5 mmol) in $CH_2Cl_2$ (5 mL). The solution was stirred at room temperature for one hour and then partitioned between EtOAc and saturated aqueous $NaHCO_3$. The phases were separated and the organics were washed with saturated aqueous NaCl. The organics were dried over anhydrous $Na_2SO_4$ and concentrated. The residue was purified twice by silica gel chromatography (0-20% EtOAc/hexanes and then 0-50% $CH_2Cl_2$/hexanes) to provide the expected product (0.11 g, 32%).

Step C: Preparation of (2S,3R)-3-((tert-butyldimethylsilyl)oxy)-2-methyl-3-phenylbutanoic acid. Lithium hydroxide (29 mg, 1.2 mmol) and 30% aqueous hydrogen peroxide (0.12 mL, 1.2 mmol) were added to a 0° C. mixture of (R)-4-benzyl-3-((2S,3R)-3-((tert-butyldimethylsilyl)oxy)-2-methyl-3-phenylbutanoyl)oxazolidin-2-one from Step B (110 mg, 0.24 mmol) in 1:1 tetrahydrofuran/$H_2O$ (3 mL). The mixture was stirred at 0° C. to room temperature overnight. The mixture was adjusted to pH 2 via the addition of 1 M aqueous HCl and then treated with solid NaCl until the solids failed to dissolve. The mixture was then partitioned between saturated aqueous NaCl and EtOAc. The phases were separated and the aqueous layer was extracted again with EtOAc. The organics were combined, dried over anhydrous $Na_2SO_4$ and concentrated. The residue was purified by silica gel chromatography (0-50% $CH_2Cl_2$/hexanes) to provide the expected product (10 mg, 24%).

Step D: Preparation of (2S,3R)-3-((tert-butyldimethylsilyl)oxy)-N-(6-cyano-1-cyclobutyl-1H-benzo[d]imidazol-2-yl)-2-methyl-3-phenylbutanamide. A mixture of 2-amino-3-cyclobutyl-3H-imidazo[4,5-b]pyridine-5-carbonitrile (7.0 mg, 0.032 mmol), (2S,3R)-3-((tert-butyldimethylsilyl)oxy)-2-methyl-3-phenylbutanoic acid from Step C (10 mg, 0.032 mmol), HOBt (7.0 mg, 0.049 mmol), EDC (8.0 mg, 0.049 mmol) and diisopropylethylamine (17 µL, 0.097 mmol) in dimethyformamide (2 mL) were stirred at 50° C. for 3 days. The mixture was cooled to room temperature and partitioned between water and EtOAc. The aqueous phase was extracted twice more with EtOAc. The combined organics were washed with saturated aqueous NaCl, dried over anhydrous $Na_2SO_4$ and concentrated. This crude material was used as is in the next step.

Step E: Preparation of (2S,3R)-N-(6-cyano-1-cyclobutyl-1H-benzo[d]imidazol-2-yl)-3-hydroxy-2-methyl-3-phenylbutanamide. TBAF (1.0 M tetrahydrofuran, 160 µL, 0.16 mmol) was added to a solution of the crude product from Step D above in tetrahydrofuran (0.32 mL). The mixture was stirred at 50° C. overnight, cooled to room temperature and concentrated. The residue was purified by reverse phase chromatography (10% CH$_3$CN/H$_2$O to CH$_3$CN) to afford the title compound (1.7 mg, 14% over two steps). MS (ESI) m/z 389.2 (MH$^+$).

Example 29

Preparation of (S)-N-(6-cyano-1-cyclobutyl-1H-benzo[d]imidazol-2-yl)-3-hydroxy-3-phenylbutanamide

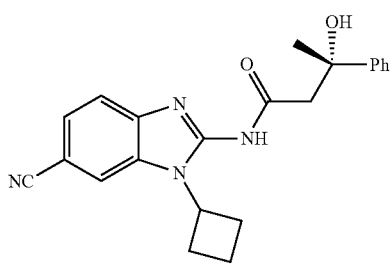 [SMILES: C[C@](O)(CC(=O)Nc1nc2ccc(C#N)cc2n1C1CCC1)c1ccccc1]

Step A: Preparation of (S)-4-benzyl-3-((S)-3-hydroxy-3-phenylbutanoyl)oxazolidin-2-one. Lithium bis(trimethylsilyl)amide (1.0 M tetrahydrofuran, 9.2 mL, 9.2 mmol) was added over 15 minutes to a -78° C. suspension of (S)-3-acetyl-4-benzyloxazolidin-2-one (2.0 g, 9.2 mmol) in tetrahydrofuran (9 mL). The mixture was stirred at -78° C. for two hours. A solution of acetophenone (485 µL, 4.2 mmol) in tetrahydrofuran (3 mL) was added over 35 minutes. The mixture was stirred at -78° C. for one hour and then quenched via the addition of aqueous 0.5 M HCl. The mixture was warmed to room temperature and then extracted with CH$_2$Cl$_2$. The layers were separated and the aqueous phase was extracted twice more with CH$_2$Cl$_2$. The combined organics were dried over anhydrous Na$_2$SO$_4$ and concentrated. The residue was purified by silica gel chromatography (0-30% EtOAc/hexanes) to provide the desired compound in a partially purified fashion (1.6 g) that was used as is. The stereochemistry was assigned as reported in Theurer, et al; *Tetrahedron*, 2010, 66, 3814.

Step B: Preparation of (S)-4-benzyl-3-((S)-3-((tert-butyldimethylsilyl)oxy)-3-phenylbutanoyl)oxazolidin-2-one. tert-Butyldimethylsilyl trifluoromethanesulfonate (1.3 mL, 5.7 mmol) was added dropwise to a room temperature solution of the residue prepared as described in Step A and Et$_3$N (1.1 mL, 7.5 mmol) in CH$_2$Cl$_2$ (24 mL). The mixture was stirred at room temperature overnight and then partitioned between EtOAc and saturated aqueous NaHCO$_3$. The phases were separated and the organics were washed with saturated aqueous NaCl. The two aqueous phases were then sequentially extracted twice with EtOAc. The combined organics were dried over anhydrous Na$_2$SO$_4$ and concentrated. The residue was purified twice by silica gel chromatography (0-30% EtOAc/hexanes and then 0-50% CH$_2$Cl$_2$/hexanes) to provide the expected product (0.57 g, 30% over two steps).

Step C: Preparation of (S)-3-((tert-butyldimethylsilyl)oxy)-3-phenylbutanoic acid. Lithium hydroxide (150 mg, 6.3 mmol) and 30% aqueous hydrogen peroxide (0.64 mL, 6.3 mmol) were added to a 0° C. mixture of (S)-4-benzyl-3-((S)-3-((tert-butyldimethylsilyl)oxy)-3-phenylbutanoyl)oxazolidin-2-one from Step B (570 mg, 1.3 mmol) in 1:1 tetrahydrofuran/H$_2$O (13 mL). The mixture was stirred at 0° C. to room temperature over 80 minutes. The mixture was adjusted to pH 2 via the addition of 1 M aqueous HCl and then treated with solid NaCl until the solids failed to dissolve. The mixture was then partitioned between saturated aqueous NaCl and EtOAc. The phases were separated and the aqueous layer was extracted again with EtOAc. The organics were combined, dried over anhydrous Na$_2$SO$_4$ and concentrated. The residue was purified by silica gel chromatography (0-60% EtOAc/hexanes) to provide the expected product (0.21 g, 57%).

The title compound was then prepared using the procedures described in Step D and Step E of Example 18. MS (ESI) m/z 375 (MH$^+$).

Example 30

Preparation of (R)-N-(6-cyano-1-cyclobutyl-1H-benzo[d]imidazol-2-yl)-3-hydroxy-3-phenylbutanamide

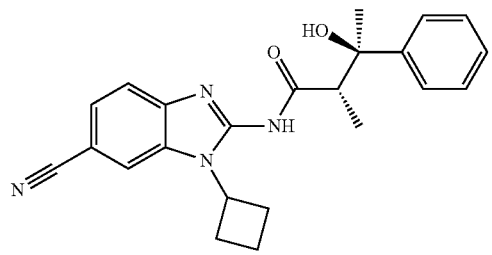 [SMILES: C[C@H](C(=O)Nc1nc2ccc(C#N)cc2n1C1CCC1)[C@@](C)(O)c1ccccc1]

The same procedure was used to prepare the title compound as was used for Example 29 with the exception of starting with (R)-3-acetyl-4-benzyloxazolidin-2-one instead of the (S)-enantiomer. MS (ESI) m/z 375 (MH$^+$).

Example 20

Preparation of (S)-N-(6-cyano-1-cyclobutyl-1H-benzo[d]imidazol-2-yl)-3-hydroxy-3-(pyridin-2-yl)butanamide

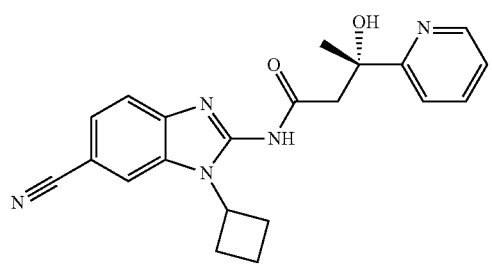 [SMILES: C[C@](O)(CC(=O)Nc1nc2ccc(C#N)cc2n1C1CCC1)c1ccccn1]

The same procedure was used to prepare the title compound as was used for Example 29 with the exception of starting with (R)-3-acetyl-4-benzyloxazolidin-2-one instead of the (S)-enantiomer, and using 2-acetopyridine in place of acetophenone. MS (ESI) m/z 376 (MH$^+$). Stereochemical assignment based on Peters R, et al., *J. Org. Chem.* 2006, 71, 7583-7595.

Example 21

Preparation of (S)-N-(6-cyano-1-cyclobutyl-1H-benzo[d]imidazol-2-yl)-3-hydroxy-3-(pyridine-3-yl)butanamide

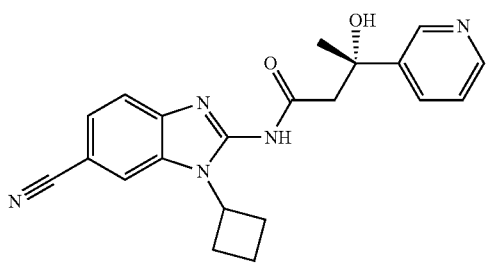 [SMILES: C[C@](O)(CC(=O)Nc1nc2ccc(C#N)cc2n1C1CCC1)c1cccnc1]

The same procedure was used to prepare the title compound as was used for Example 29 with the exception of starting with (R)-3-acetyl-4-benzyloxazolidin-2-one instead of the (S)-enantiomer and using 3-acetopyridine in place of acetophenone.

Example 23

Preparation of (S)-N-(6-cyano-1-cyclobutyl-1H-benzo[d]imidazol-2-yl)-2,3,3-trimethylbutanamide

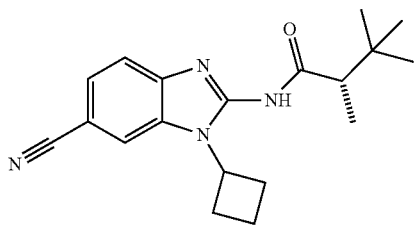 [SMILES: C[C@H](C(=O)Nc1nc2ccc(C#N)cc2n1C1CCC1)C(C)(C)C]

Step A: Preparation of (S)-4-benzyl-3-(3,3-dimethylbutanoyl)oxazolidin-2-one.

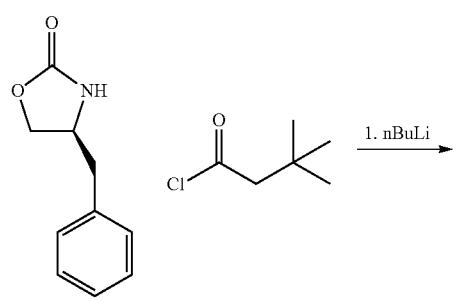

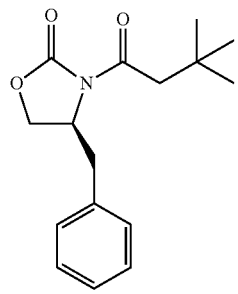

A 1.0 L round bottom flask was charged with a stir bar, tetrahydrofuran (200 mL, anhydrous) and (S)-4-benzyloxazolidin-2-one (10.0 g, 56.4 mmol). The flask was placed in a -78° C. bath for 15 minutes prior to the addition of n-BuLi (2.5 M in hexanes, 25.0 mL, 1.1 equivalents) dropwise under a nitrogen atmosphere. The reaction was allowed to stir for 1 hour prior to the addition of 3,3-dimethylbutanoyl chloride (11.7 mL, 1.5 equivalents). The reaction was allowed to stir at -78° C. and then the cooling bath was removed and the flask was allowed to slowly warm to room temperature and stir overnight. The reaction was quenched by the addition of saturated aqueous sodium bicarbonate (200 mL) and the bulk of the tetrahydrofuran was removed by rotary evaporation. The remaining residue was dissolved in ethyl acetate (300 mL) and washed sequentially with saturated aqueous sodium bicarbonate (twice), saturated aqueous sodium carbonate (twice), and brine and then dried over sodium sulfate. The dried solution was filtered and concentrated to give 20 g of crude product. The material was recrystallized from warm ethyl acetate (approximately 30 mL) and warm hexanes (approximately 70 mL) to give the first crop of the desired product (9.0 g. 58% yield) as white crystals. An additional second crop (3.8 g, 25% yield) was obtained from the mother liquor. $^1$H NMR (CDCl$_3$): δ 7.36-7.22 (m, 5H), 4.73-4.67 (m, 1H), 4.18-4.12 (m, 2H), 3.34 (dd, J=13.28, 3.32 Hz, 1H), 2.99 (d, J=14.9 Hz, 1H), 2.86 (d, J=14.9 Hz, 1H), 2.71 (dd, J=13.24, 10.00 Hz, 1H), 1.09 (br s, 9H).

Step B: Preparation of (S)-4-benzyl-3-((S)-2,3,3-trimethylbutanoyl)oxazolidin-2-one.

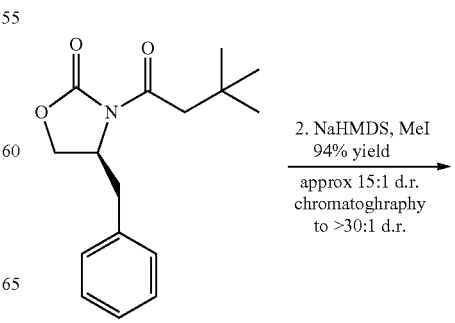

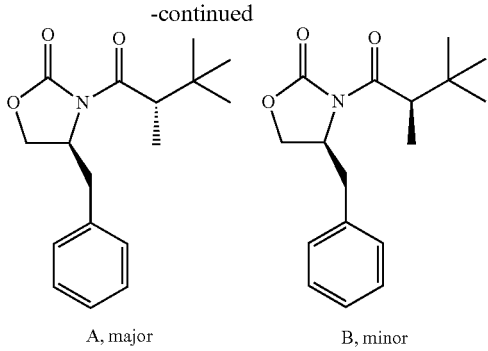

A, major      B, minor

Freshly recrystallized (S)-4-benzyl-3-(3,3-dimethylbutanoyl)oxazolidin-2-one (8.75 g, 31.77 mmol) was azeotroped with dichloromethane (2×, 30 mL) and then placed under high vacuum for 10 minutes prior to being dissolved in tetrahydrofuran (40 mL). In a 1.0 L round bottom flask fitted with a balloon of nitrogen and a stir bar was placed NaHMDS (1.0 M in tetrahydrofuran, 35 mL, 1.1 equivalents) and the flask was placed in a -78° C. bath. After being chilled for 15 minutes, the 40 mL tetrahydrofuran solution of (S)-4-benzyl-3-(3,3-dimethylbutanoyl)oxazolidin-2-one was added dropwise to the NaHMDS at -78° C. The formation of the sodium enolate was allowed to form over 1 hour at -78° C. and then methyl iodide (6 mL, 3 equivalents) was added via syringe. The reaction was allowed to stir and slowly warm to room temperature overnight. The reaction was quenched by the addition of saturated aqueous sodium bicarbonate (150 mL) and the bulk of the tetrahydrofuran was removed by rotary evaporation. The residue was transferred to a separatory funnel using ethyl acetate and saturated aqueous sodium bicarbonate. The layers were separated and the organic layer was washed with 10% aqueous sodium thiosulfate (150 mL) to remove the pale yellow color. The combined organic layers were back extracted with ethyl acetate (2×). The combined organics were washed with brine, dried with sodium sulfate, filtered and concentrated to give a white solid (8.61 g, 94% yield). $^1$H NMR analysis indicated complete conversion of starting material to the methylated products and an approximately 15:1 diastereomeric ratio of products in favor of the desired (S)-4-benzyl-3-((S)-2,3,3 trimethylbutanoyl)oxazolidin-2-one diastereomer A. An attempt to enrich the diastereomeric ratio by recrystallization from warm hexanes failed to improve the diastereomeric ratio. Therefore, the initial solid product was divided into three portions and each one was subjected to column chromatography (Isco, 120 g silica gel, 0-10% EtOAc in hexanes). The higher running $R_f$ fractions of the UV peak were cut off from the later running fractions to give a product of improved diastereomeric ratio (1.83 g, approximately 70:1 d.r.) as a white solid. The chromatography was repeated on the original product to give two samples of improved diastereomeric ratio (2.28 g, >20:1 d.r and 4.59 g, 30:1 d.r.) in favor of (S)-4-benzyl-3-((S)-2,3,3-trimethylbutanoyl)oxazolidin-2-one diastereomer. Major diastereomer A $^1$H NMR (CDCl$_3$): δ 7.33-7.23 (m, 5H), 4.73-4.67 (m, 1H), 4.17-4.13 (m, 2H), 3.90 (q, J=7.00 Hz, 1H), 3.28 (dd, J=13.32, 3.20 Hz, 1H), 2.77 (dd, J=13.32, 9.72 Hz, 1H), 1.20 (d, J=7.00 Hz, 3H), 1.02 (bs, 9H). The latter running $R_f$ fraction were combined to give the desired product in a diminished diastereomeric ratio (360 mg, 3:1 d.r.) contaminated with the undesired (S)-4-benzyl-3-((R)-2,3,3-trimethylbutanoyl)oxazolidin-2-one minor diastereomer B (Reference: Evans, D A; Ennis, M D; Mathre, D J *J. Am. Chem. Soc.* 1982, 104, 1737-1739).

Step C: Preparation of (S)-2,3,3-trimethylbutanoic acid.

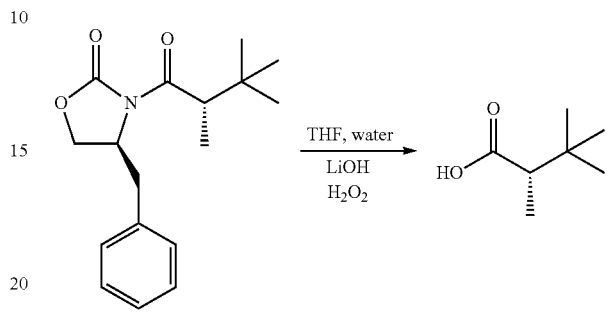

Solid (S)-4-benzyl-3-((S)-2,3,3-trimethylbutanoyl)oxazolidin-2-one (2.24 g, 7.73 mmol, diastereomer A from Step B above, approx. 30:1 d.r) was dissolved in tetrahydrofuran (50 mL) and water (10 mL) and the flask was allowed to chill in a 0° C. for 10 minutes prior to the addition of lithium hydroxide (326 mg, 13.6 mmol, 2 equivalents) in one portion. After a few minutes, hydrogen peroxide (30%, 6 mL) was added via syringe. After approximately 30 min, an additional portion of tetrahydrofuran (60 mL) and water (10 mL) were added to the flask. The reaction was allowed to stir at 0° C. for 1 hour and then allowed to warm to room temperature and stirred for 24 hours. The flask was rechilled to 0° C. and then quenched by the addition of sodium sulfite (19 g in 125 mL of water) and saturated aqueous sodium bicarbonate (75 mL). The quenched reaction was allowed to stir for 1.5 hours and then the bulk of the tetrahydrofuran was removed by rotary evaporation. The mixture was transferred to a separatory funnel using dichloromethane and saturated aqueous sodium bicarbonate. The aqueous layer was extracted with dichloromethane (3×50 mL) to remove the bulk of the chiral auxiliary. The aqueous layer was carefully acidified with HCl (1 M, until pH=2) and then extracted with dichloromethane (4×50 mL). The combined organics were washed with brine and dried with sodium sulfate. The dried solution was filtered and carefully evaporated to give the desired carboxylic acid as an oil (925 mg, >100% yield, dichloromethane impurity). The (S)-2,3,3-trimethylbutanoic acid was diluted up to a volume of 9 mL with dichloromethane to make a stock solution that was used directly in the amide coupling reaction. $^1$H NMR (CDCl$_3$): δ 12.02 (br s, 1H), 2.29 (q, J=7.08 Hz, 1H), 1.13 (d, J=7.08 Hz, 3H), 0.99 (br s, 9H). (Reference: Evans, D A, Britton, T C, Ellman, J A, *Tetrahedron Lett.* 1987, 28(49), 6141-6144).

Step D: Preparation of (S)-N-(6-cyano-1-cyclobutyl-1H-benzo[d]imidazol-2-yl)-2,3,3-trimethylbutanamide.

The dichloromethane stock solution of (S)-2,3,3-trimethylbutanoic acid from Step C above was transferred to a tared flask and carefully evaporated. This acid was dissolved in dimethyformamide and the standard amide coupling Method 7 was followed to give the desired product.

Example 13

Preparation of (S)-N-(6-cyano-1-cyclobutyl-1H-benzo[d]imidazol-2-yl)-3-hydroxy-2,3-dimethylbutanamide

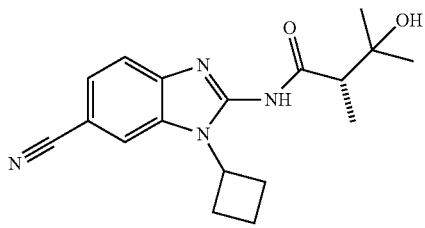 [SMILES: C[C@H](C(=O)Nc1nc2ccc(C#N)cc2n1C1CCC1)C(C)(C)O]

Step A. Preparation of (R)-4-benzyl-3-((S)-3-hydroxy-2,3-dimethylbutanoyl)oxazolidin-2-one.

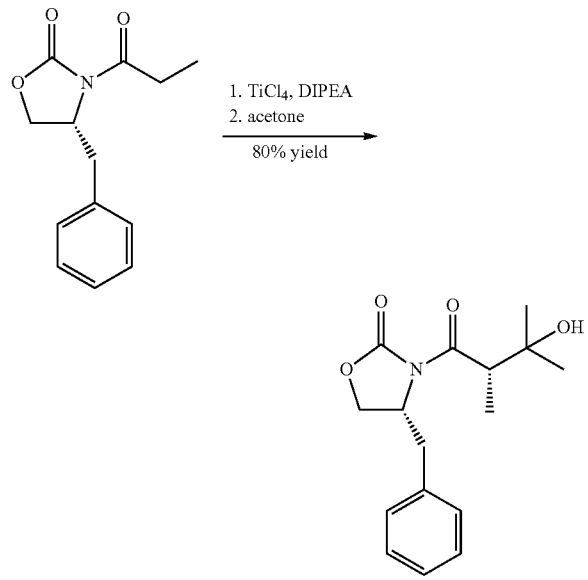

Commercially available (R)-4-benzyl-3-propionyloxazolidin-2-one (3.0 g, 12.85 mmol, 1.0 equivalents) was dissolved in dichloromethane (40 mL) and chilled to 0° C. for 10 minutes prior to the addition of TiCl$_4$ (1.0 M in dichloromethane, 14.15 mL, 1.1 equivalents) via syringe under an atmosphere of nitrogen. After 5 minutes, diisopropylethylamine (2.5 mL, 1.1 equivalents) was added dropwise via syringe. The reaction was allowed to stir at 0° C. for 1 hour and a dark-red titanium enolate formed. At this time, acetone (1.4 mL, 1.5 equivalents, dried over anhydrous potassium carbonate for 24 hours) was added via syringe. The reaction was allowed to stir at 0° C. for 15 minutes and then slowly allowed to warm to room temperature overnight. The reaction was quenched by the addition of aqueous ammonium chloride (1 M, 100 mL) and extracted with dichloromethane (three times). The combined organics were washed with brine, dried with sodium sulfate, filtered and concentrated to give 4.0 g of a crude oil. The crude oil was subjected to column chromatography (Isco, 120 g silica gel, 0-25% EtOAc in hexanes) to give the desired product (3.0 g, 80% yield) as a white solid. NMR analysis indicated a single diastereomer of the purified product. $R_f$=0.75 in 20% EtOAc in hexanes. $^1$H NMR (CDCl$_3$): δ 7.32-7.23 (m, 5H), 4.72-4.66 (m, 1H), 4.20-4.13 (m, 2H), 3.95 (q, J=7.00 Hz, 1H), 3.38-3.34 (m, 2H), 2.75 (dd, J=13.36, 9.88 Hz, 1H), 1.35 (s, 3H), 1.24-1.23 (m, 6H). (Reference: Evans, D A, Urpi, F, Somers, T C. Clark, J S, Bilodeau, M T, *J. Am. Chem. Soc.* 1990, 112, 8215-8216).

Step B: Preparation of (R)-4-benzyl-3-((S)-3-((tert-butyldimethylsilyl)oxy)-2,3-dimethylbutanoyl)oxazolidin-2-one.

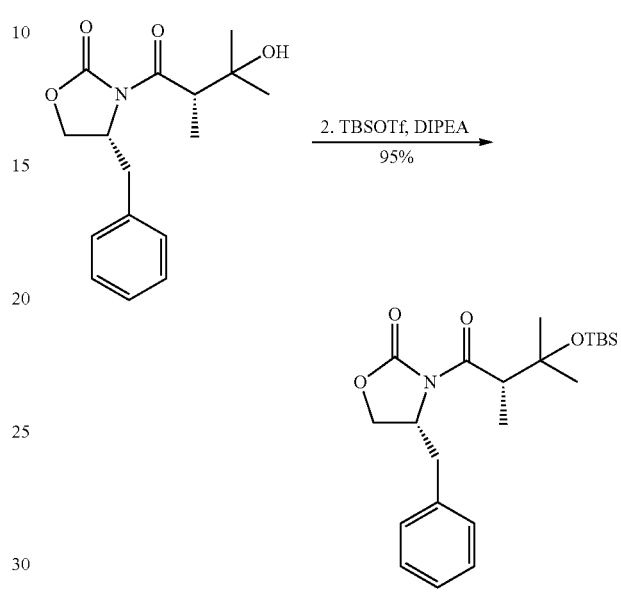

The solid tertiary alcohol (1000 mg, 3.43 mmol, 1.0 equivalents) from the above procedure, (R)-4-benzyl-3-((S)-3-hydroxy-2,3-dimethylbutanoyl)oxazolidin-2-one, was dissolved in dichloromethane (10 mL) and diisopropylethylamine (0.9 mL, 1.5 equivalents) was added via syringe. The flask was chilled for 10 minutes in a 0° C. bath prior to the drop wise addition of tert-butyldimethylsilyl triflate (0.9 mL, 1.1 equivalents) via syringe. The reaction was allowed to stir overnight and then quenched by the addition of saturated aqueous sodium bicarbonate (50 mL). The aqueous layer was extracted twice with dichloromethane. The combined organics were washed with brine, dried with sodium sulfate, filtered and concentrated to give a crude oil. The crude material was subjected to silica gel column chromatography (Isco, 24 g silica gel, 0-20% EtOAc in hexanes) to give the desired TBS ether (1.23 g, 95%) as a white solid. $R_f$=0.75 in 20% EtOAc in hexanes. $^1$H NMR (CDCl$_3$): δ 7.24-7.12 (m, 5H), 4.57-4.51 (m, 1H), 4.10-3.93 (m, 3H), 3.33 (dd, J=13.08, 3.16 Hz, 1H), 2.47 (dd, J=13.00, 10.88 Hz, 1H), 1.25 (s, 3H), 1.24 (s, 3H), 1.07 (d, J=7.00 Hz, 3H), 0.76 (bs, 9H), 0.00 (d, J=5.72 Hz, 6H).

Step C: Preparation of (S)-3-((tert-butyldimethylsilyl)oxy)-2,3-dimethylbutanoic acid.

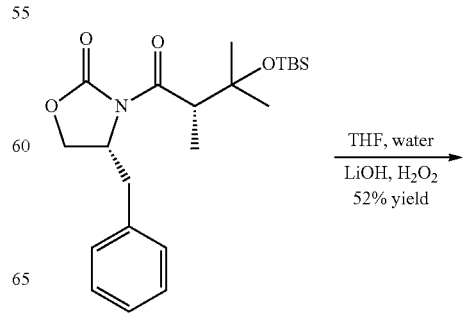

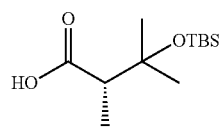

Solid (R)-4-benzyl-3-((S)-3-((tert-butyldimethylsilyl)oxy)-2,3-dimethylbutanoyl)oxazolidin-2-one (3.8 g, 9.7 mmol, >30:1 d.r) was dissolved in tetrahydrofuran (50 mL) and water (10 mL) and the flask was allowed to chill in a 0° C. for 5 minutes prior to the addition of lithium hydroxide (450 mg, 18.7 mmol, 2 equivalents) in one portion. After a few minutes, hydrogen peroxide (30%, 12 mL) was added via syringe. The reaction was allowed to stir at 0° C. for 1 hour and then allowed to warm to room temperature and stirred for 24 hours. The flask was rechilled to 0° C. and then quenched by the addition of sodium sulfite (12 g in 100 mL of water). The quenched reaction was allowed to stir for 1.5 hours and then the bulk of the tetrahydrofuran was removed by rotary evaporation. The mixture was transferred to a separatory funnel using dichloromethane and saturated aqueous sodium bicarbonate. The aqueous layer was extracted with dichloromethane (2×50 mL). This initial dichloromethane extract was found to contain both the chiral auxiliary and the desired TBS ether acid. The combined organics were washed with brine and dried with sodium sulfate, filtered and concentrated to give the crude product as oil (3.1 g). The crude material was subjected to silica gel column chromatography (Isco, 40 g, 0-25% EtOAc in hexanes, ELSD detection) to give the desired product as oil (1.2 g, 52% yield). $R_f$=0.50 in 20% EtOAc in hexanes, purple to anisaldehyde stain and is not UV active. $^1$H NMR (CDCl$_3$): δ 10.4-9.80 (br s, 1H), 2.32 (q, J=7.16 Hz, 1H), 1.19 (s, 3H), 1.14 (s, 3H), 1.03 (d, J=7.16 Hz, 3H), 0.72 (s, 9H), 0.00 (s, 6H).

Step D: Preparation (S)-3-((tert-butyldimethylsilyl)oxy)-N-(6-cyano-1-cyclobutyl-1H-benzo[d]imidazol-2-yl)-2,3-dimethylbutanamide.

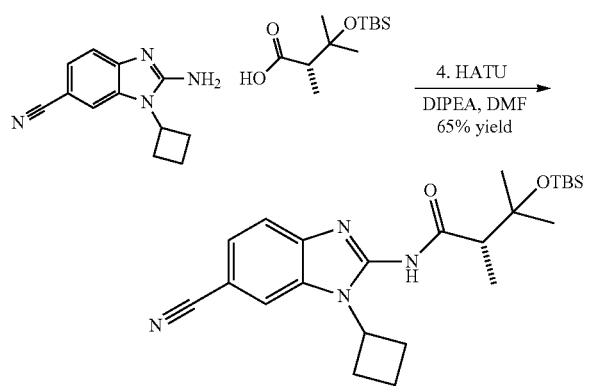

Method 7 was used to provide the desired amide product (38 mg, 65% yield), isolated via column chromatography. The isolated material was contaminated with the activated ester of the corresponding carboxylic acid coupling partner. The material was taken forward to the next step without any further purification.

Step E: Preparation of (S)-N-(6-cyano-1-cyclobutyl-1H-benzo[d]imidazol-2-yl)-3-hydroxy-2,3-dimethylbutanamide via deprotection of TBDMS ether.

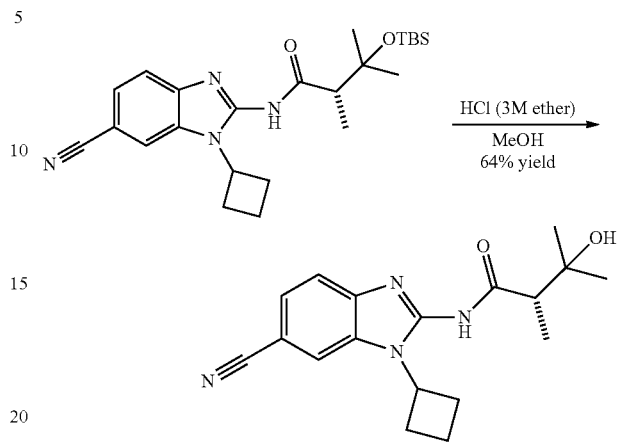

Crude (S)-3-((tert-butyldimethylsilyl)oxy)-N-(6-cyano-1-cyclobutyl-1H-benzo[d]imidazol-2-yl)-2,3-dimethylbutanamide from Step D above (38 mg) was dissolved in MeOH (4 mL) and HCl (3 M in diethyl ether, 2 mL) was added to the reaction via syringe. The reaction was allowed to stir at room temperature for 30 minutes when LC/MS analysis indicated a slow and clean deprotection of the TBS ether. The flask was placed in a 50° C. sand bath and allowed to stir capped for 20 hours. The flask was allowed to cool and then quenched by the careful addition of saturated aqueous sodium bicarbonate (30 mL) and ethyl acetate (30 mL). The aqueous layer was extracted twice with ethyl acetate. The combined organics were washed with brine, dried with sodium sulfate, filtered and concentrated to give a crude oil. The crude material was subjected to column chromatography (Isco, 12 g silica gel, 5-75% EtOAc in hexanes) to give the desired product (18 mg, 64% yield). MS (ESI) m/z 327.2 (MH$^+$).

Example 12

Preparation of N-(6-cyano-1-cyclobutyl-1H-benzo[d]imidazol-2-yl)-3-methoxy-3-methylbutanamide

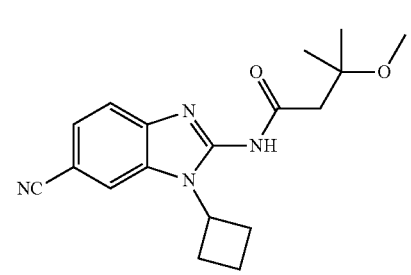 [SMILES: COC(C)(C)CC(=O)Nc1nc2ccc(C#N)cc2n1C1CCC1]

Step A. Preparation of 3-methoxy-3-methylbutanoic acid.

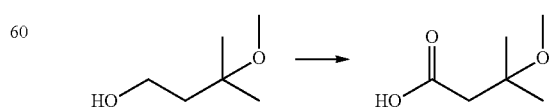

To a solution of 3-methoxy-3-methylbutan-1-ol (0.6 g, 5 mmol) in acetonitrile (20 mL) was added N-methyl morpholine N-oxide monohydrate (6.8 g, 50 mmol, 10 equivalents) and the mixture was allowed to stir at room temperature. After 5 min, tetrapropylammonium perruthenate (175 mg, 0.5 mmol, 0.1 equivalents) was added in one portion and the reaction was allowed to stir for 3 h before the bulk of the solvent was carefully removed on a rotary evaporator (caution, the product is volatile). The residue was purified by column chromatography (50-100% EtOAc/hexanes). The hexanes and EtOAc were removed by both rotary evaporator and a short period of time to high vacuum. The product is volatile and must not be left under vacuum for more than 30 sec. The resulting purified acid was diluted with dimethyformamide (7 mL) to make an approximately 0.2 M solution that was used for amide coupling reaction as is. $R_f$=0.4 to 0.8 streak in 100% EtOAc, not UV active, stains purple to anisaldehyde. M-1=131.2. $^1$H NMR (CDCl$_3$): δ 12.0-9.0 (bs, 1H), 3.30 (s, 3H), 2.57 (s, 2H), 1.32 (s, 6H). (Reference: Schmidt, A-KC, Stark, B W, Org. Lett. 2011, 13, 4164-4167).

Step B. Preparation of N-(6-cyano-1-cyclobutyl-1H-benzo[d]imidazol-2-yl)-3-methoxy-3-methylbutanamide.

The title compound was prepared from 3-methoxy-3-methylbutanoic acid and 4-amino-3-(cyclobutylamino) benzonitrile according to Method 7. MS (ESI) m/z 327 (MH$^+$).

Example 103

Preparation of (S)-N-(6-chloro-1-cyclobutyl-1H-benzo[d]imidazol-2-yl)-3-(4-fluorophenyl)-3-hydroxybutanamide

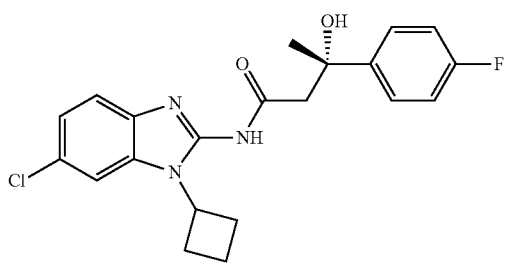 [SMILES: C[C@](O)(CC(=O)Nc1nc2ccc(Cl)cc2n1C1CCC1)c1ccc(F)cc1]

Step A: Preparation of (S)-4-benzyl-3-((S)-3-(4-fluorophenyl)-3-hydroxybutanoyl)oxazolidin-2-one. Lithium bis(trimethylsilyl)amide (1.0 M tetrahydrofuran, 6.6 mL, 6.6 mmol) was added over 15 minutes to a -78° C. suspension of (S)-3-acetyl-4-benzyloxazolidin-2-one (1.5 g, 6.6 mmol) in tetrahydrofuran (18 mL). The mixture was stirred at -78° C. for two hours. Acetophenone (330 μL, 3.2 mmol) was added dropwise over 5 minutes. The mixture was stirred at -78° C. for one hour and then quenched via the addition of aqueous 0.5 M HCl. The mixture was warmed to room temperature and then extracted with CH$_2$Cl$_2$. The layers were separated and the aqueous phase was extracted twice more with CH$_2$Cl$_2$. The combined organics were dried over anhydrous Na$_2$SO$_4$ and concentrated. The residue was purified by silica gel chromatography (0-30% EtOAc/hexanes) to provide the desired (0.80 g).

Step B: Preparation of (S)-3-(4-fluorophenyl)-3-hydroxybutanoic acid. Lithium hydroxide (210 mg, 9.0 mmol) was added to a 0° C. mixture of (S)-4-benzyl-3-((S)-3-(4-fluorophenyl)-3-hydroxybutanoyl)oxazolidin-2-one (0.80 g, 2.2 mmol) and 50% aqueous hydrogen peroxide (0.51 mL, 9.0 mmol) in 1:1 tetrahydrofuran/H$_2$O (9 mL). The mixture was stirred at 0° C. for 15 minutes, then at room temperature for three hours. The mixture was adjusted to pH 7 via the addition of 1 M aqueous HCl and then was diluted with EtOAc. The layers were separated, the aqueous phase was adjusted to pH 2 via the addition of 1 M aqueous HCl and then treated with solid NaCl until the solids failed to dissolve. The mixture was then partitioned between saturated aqueous NaCl and EtOAc. The phases were separated and the aqueous layer was extracted again with EtOAc. The organics were combined, dried over anhydrous Na$_2$SO$_4$ and concentrated to provide the expected product (0.35 g, 79%).

The title compound was then prepared using the procedures described in Step D of Example 18, substituting (S)-3-(4-fluorophenyl)-3-hydroxybutanoic acid for (2S,3R)-3-((tert-butyldimethylsilyl)oxy)-2-methyl-3-phenylbutanoic acid and 6-chloro-1-cyclobutyl-1H-benzo[d]imidazol-2-amine for 2-amino-1-cyclobutyl-1H-benzo[d]imidazole-6-carbonitrile. MS (ESI) m/z 402 (MH$^+$).

Preparation of 2-(1-hydroxycyclopentyl)acetic acid

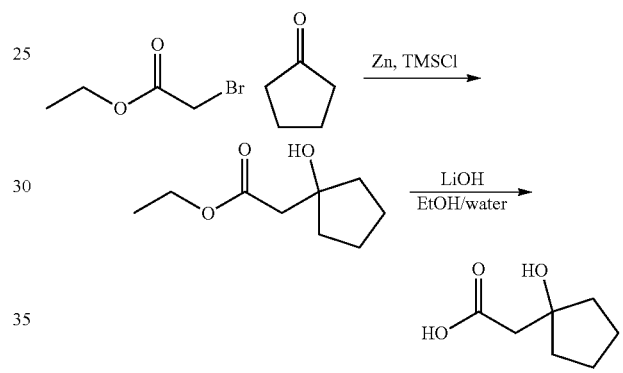

Step A. Preparation of ethyl 2-(1-hydroxycyclopentyl)acetate. Chlorotrimethylsilane (181 μL, 1.4 mmol) was added to a suspension of zinc powder (1.2 g, 19 mmol) in Et$_2$O (30 mL). The mixture was stirred at room temperature for 15 minutes and then refluxed for 15 minutes. The heat source was removed and ethyl bromoacetate (1.8 mL, 14 mmol) was added dropwise to the warm mixture. The mixture was then refluxed for one hour and then stirred at room temperature for one hour. Cyclopentanone (1.0 g, 12 mmol) was then added dropwise. The resulting mixture was stirred for one hour and then poured into ice cold concentrated aqueous ammonia (80 mL). The layers were separated and the aqueous phase was extracted with Et$_2$O (3×40 mL). The combined organics were dried (K$_2$CO$_3$) and concentrated to yield 1.7 g of a colorless oil. This material was used as is in the next step.

Step B. Preparation of 2-(1-hydroxycyclopentyl)acetic acid. Lithium hydroxide (1.4 g, 58 mmol) was added to a room temperature solution of the crude ester prepared as described in the previous step (1.0 g, 5.8 mmol) in 1:1 EtOH:water (29 mL). After 2 hours, the reaction was partitioned between water (100 mL) and MTBE (100 mL). The aqueous layer was isolated and the pH was adjusted to pH=2 with 1.0 N aqueous HCl. The aqueous mixture was extracted three times with EtOAc. The combined organics were dried (Na$_2$SO$_4$) and concentrated to afford the desired product (500 mg, 60%). (ESI) m/z 143.2 (M-H).

The following carboxylic acids were prepared using an analogous procedure to that described for preparation of 2-(1-hydroxycyclopentyl)acetic acid with appropriate starting materials.

3,3-dicyclopropyl-3-hydroxypropanoic acid 3-cyclopentyl-3-hydroxybutanoic acid 3-cyclobutyl-3-hydroxybutanoic acid Preparation of
3-hydroxy-2,2-dimethyl-3-phenylpropanoic acid

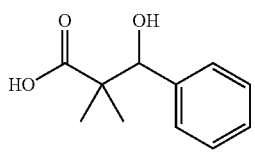

The preparation of 3-hydroxy-2,2-dimethyl-3-phenylpropanoic acid is detailed in *J. Org. Chem.*, 2012, 77 (11), 4885-4901.

Section 5. General Analytical Methods.

LCMS was conducted on an Agilent 1100 MSD instrument equipped with an Ascentis Express C18, 10 cm×4.6 mm×2.7 mm column, using the following methods:

HPLC Method A
Solvent A: 0.1% formic acid in water
Solvent B: Acetonitrile
Flow rate: 1.4 mL/min
Method:
0-6.0 min gradient from B=10% to B=95%
6.0-8.0 min, hold B=95%
8.0-8.2 min, gradient from B=95% to B=10%
8.2-10.0 min, hold B=10%

HPLC Method B:
Solvent A: 0.1% formic acid in water
Solvent B: Acetonitrile
Flow rate: 1.4 mL/min
Method:
0-3.0 min gradient from B=10% to B=95%
3.0-4.0 min, hold B=95%
4.0-4.2 min, gradient from B=95% to B=10%
4.2-6.0 min, hold B=10%

Table 1 shows the structures of the various Examples prepared by these general methods, and indicates the general coupling method used, together with a summary of the LCMS analytical data.

TABLE 1

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 1 | $C_{17}H_{23}N_3O$ | N-(1-cyclobutyl-1H-benzo[d]imidazol-2-yl)-3,3-dimethylbutanamide | 7 | B | 2.7 | 286 |
| 2 | $C_{19}H_{21}N_3O$ | 3,3-dimethyl-N-(1-phenyl-1H-benzo[d]imidazol-2-yl)butanamide | 9 | B | 2.8 | 308 |
| 3 | $C_{19}H_{27}N_3O_2$ | 3-cyclopentyl-N-(1-isopropyl-6-methoxy-1H-benzo[d]imidazol-2-yl)propanamide | 12 | A | 5.5 | 330 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 4 | C₁₇H₂₅N₃O₂ | (S)-N-(1-isopropoxy-6-methoxy-1H-benzo[d]imidazol-2-yl)-2,3-dimethylbutanamide | 7 | B | 2.7 | 304 |
| 5 | C₁₀H₂₂N₄O | N-(6-cyano-1-cyclobutyl-1H-benzo[d]imidazol-2-yl)-3,3-dimethylbutanamide | 7 | B | 3.5 | 311 |
| 6 | C₁₈H₂₂N₄O | (S)-N-(6-cyano-1-cyclobutyl-1H-benzo[d]imidazol-2-yl)-2,3-dimethylbutanamide | 7 | B | 3.5 | 311 |
| 7 | C₁₈H₂₂N₄O | (S)-N-(6-cyano-1-cyclobutyl-1H-benzo[d]imidazol-2-yl)-2,3-dimethylbutanamide | 7 | A | 4.9 | 311 |
| 8 | C₁₇H₂₀N₄O₂ | N-(6-cyano-1-cyclobutyl-1H-benzo[d]imidazol-2-yl)-3-hydroxy-3-methylbutanamide | 7 | B | 2.7 | 313 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 9 | 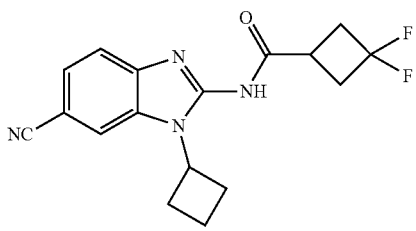 [SMILES: N#Cc1ccc2nc(NC(=O)C3CC(F)(F)C3)n(C3CCC3)c2c1] $C_{17}H_{16}F_2N_4O_2$ | N-(6-cyano-1-cyclobutyl-1H-benzo[d]imidazol-2-yl)-3,3-difluorocyclobutane-1-carboxamide | 7 | B | 3.5 | 331 |
| 10 | 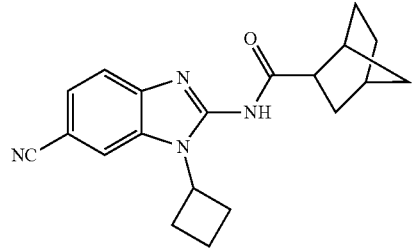 [SMILES: N#Cc1ccc2nc(NC(=O)C3CC4CCC3C4)n(C3CCC3)c2c1] $C_{20}H_{22}N_4O$ | (1S,2R,4R)-N-(6-cyano-1-cyclobutyl-1H-benzo[d]imidazol-2-yl)bicyclo[2.2.1]heptan-2-carboxamide | 7 | B | 3.6 | 335 |
| 11 | 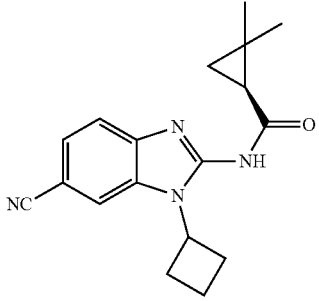 [SMILES: CC1(C)C[C@@H]1C(=O)Nc1nc2ccc(C#N)cc2n1C1CCC1] $C_{18}H_{20}N_4O$ | (S)-N-(6-cyano-1-cyclobutyl-1H-benzo[d]imidazol-2-yl)-2,2-dimethylcyclopropane-1-carboxamide | 7 | B | 3.3 | 309 |
| 12 | 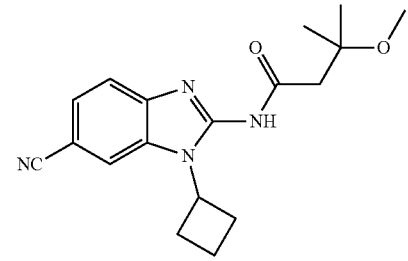 [SMILES: COC(C)(C)CC(=O)Nc1nc2ccc(C#N)cc2n1C1CCC1] $C_{18}H_{22}N_4O_2$ | N-(6-cyano-1-cyclobutyl-1H-benzo[d]imidazol-2-yl)-3-methoxy-3-methylbutanamide | 7 | B | 3.0 | 327 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 13 | C₁₈H₂₂N₄O₂ | (S)-N-(6-cyano-1-cyclobutyl-1H-benzo[d]imidazol-2-yl)-3-hydroxy-2,3-dimethylbutanamide | 7 | B | 2.9 | 327 |
| 14 | C₁₈H₂₂N₄O | (R)-N-(6-cyano-1-cyclobutyl-1H-benzo[d]imidazol-2-yl)-2,3-dimethylbutanamide | 7 | B | 3.5 | 311 |
| 15 | C₁₉H₂₂N₄O₂ | (1S,2S)-N-(6-cyano-1-cyclobutyl-1H-benzo[d]imidazol-2-yl)-2-(2-hydroxypropan-2-yl)cyclopropane-1-carboxamide | 7 | B | 2.8 | 339 |
| 16 | C₁₆H₁₅F₃N₄O₂ | (S)-N-(6-cyano-1-cyclobutyl-1H-benzo[d]imidazol-2-yl)-3,3,3-trifluoro-2-hydroxy-2-methylpropanamide | 7 | B | 3.8 | 353 |
| 17 | C₂₂H₂₂N₄O₂ | N-(6-cyano-1-cyclobutyl-1H-benzo[d]imidazol-2-yl)-3-hydroxy-3-phenylbutanamide | 7 | B | 3.4 | 375 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 18 | C₂₃H₂₄N₄O₂ | (2S,3R)-N-(6-cyano-1-cyclobutyl-1H-benzo[d]imidazol-2-yl)-3-hydroxy-2-methyl-3-phenylbutanamide | Ex 18 | B | 3.5 | 389 |
| 19 | C₂₃H₂₄N₄O₂ | (2S,3S)-N-(6-cyano-1-cyclobutyl-1H-benzo[d]imidazol-2-yl)-3-hydroxy-2-methyl-3-phenylbutanamide | Ex 19 | B | 3.8 | 389 |
| 20 | C₂₁H₂₁N₅O₂ | (S)-N-(6-cyano-1-cyclobutyl-1H-benzo[d]imidazol-2-yl)-3-hydroxy-3-(pyridin-2-yl)butanamide | 7 (no base) | A | 2.9 | 376 |
| 21 | C₂₁H₂₁N₅O₂ | (S)-N-(6-cyano-1-cyclobutyl-1H-benzo[d]imidazol-2-yl)-3-hydroxy-3-(pyridin-3-yl)butanamide | 7 | B | 2.3 | 376 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 22 | $C_{18}H_{20}F_3N_5O$ | (R)-N-(6-cyano-1-cyclobutyl-1H-benzo[d]imidazol-2-yl)-2-(methyl(2,2,2-trifluoroethyl)amino)propanamide | 7 | B | 3.6 | 380 |
| 23 | $C_{19}H_{24}N_4O$ | (S)-N-(6-cyano-1-cyclobutyl-1H-benzo[d]imidazol-2-yl)-2,3,3-trimethylbutanamide | 7 | A | 5.3 | 325 |
| 24 | $C_{18}H_{20}F_3N_5O$ | N-(6-cyano-1-cyclobutyl-1H-benzo[d]imidazol-2-yl)-3-(dimethylamino)-4,4,4-trifluorobutanamide | 7 | B | 3.4 | 380 |
| 25 | $C_{21}H_{20}N_4O_2$ | (R)-N-(6-cyano-1-cyclobutyl-1H-benzo[d]imidazol-2-yl)-3-hydroxy-3-phenylpropanamide | 7 | B | 3.1 | 361 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 26 | $C_{21}H_{20}N_4O_2$ | (S)-N-(6-cyano-1-cyclobutyl-1H-benzo[d]imidazol-2-yl)-3-hydroxy-3-phenylpropanamide | 7 | B | 3.1 | 361 |
| 27 | $C_{19}H_{22}N_4O_2$ | (S)-N-(6-cyano-1-cyclobutyl-1H-benzo[d]imidazol-2-yl)-2-(1-hydroxycyclobutyl)propanamide | 7 | B | 3.1 | 339 |
| 28 | $C_{19}H_{22}N_4O_2$ | N-(6-cyano-1-cyclobutyl-1H-benzo[d]imidazol-2-yl)-3-cyclopropyl-3-hydroxybutanamide | 7 | B | 3.1 | 339 |
| 29 | $C_{22}H_{22}N_4O_2$ | (S)-N-(6-cyano-1-cycobutyl-1H-benzo[d]imidazol-2-yl)-3-hydroxy-3-phenylbutanamide | 10 | B | 3.4 | 375 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 30 | $C_{22}H_{22}N_4O_2$ | (R)-N-(6-cyano-1-cyclobutyl-1H-benzo[d]imidazol-2-yl)-3-hydroxy-3-phenylbutanamide | 10 | B | 3.4 | 375 |
| 31 | $C_{20}H_{19}FN_4O$ | N-(6-cyano-1-(4-fluorophenyl)-1H-benzo[d]imidazol-2-yl)-3,3-dimethylbutanamide | 7 | B | 3.5 | 351 |
| 32 | $C_{20}H_{19}FN_4O$ | (S)-N-(6-cyano-1-(4-fluorophenyl)-1H-benzo[d]imidazol-2-yl)-2,3-dimethylbutanamide | 7 | B | 3.5 | 351 |
| 33 | $C_{20}H_{17}FN_4O$ | (S)-N-(6-cyano-1-(4-fluorophenyl)-1H-benzo[d]imidazol-2-yl)-2,2-dimethylcyclopropane-1-carboxamide | 7 | B | 3.4 | 349 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 34 | C$_{18}$H$_{22}$F$_3$N$_3$O | N-(1-cyclobutyl-6-(trifluoromethyl)-1H-benzo[d]imidazol-2-yl)-3,3-dimethylbutanamide | 7 | B | 3.9 | 354 |
| 35 | C$_{17}$H$_{20}$F$_3$N$_3$O$_2$ | N-(1-cyclobutyl-6-(trifluoromethyl)-1H-benzo[d]imidazol-2-yl)-3-hydroxy-3-methylbutanamide3 | 7 | B | 3.2 | 356 |
| 36 | C$_{18}$H$_{22}$F$_3$N$_3$O | (S)-N-(1-cyclobutyl-6-(trifluoromethyl)-1H-benzo[d]imidazol-2-yl)-2,3-dimethylbutanamide | 7 | B | 4.0 | 354 |
| 37 | C$_{18}$H$_{20}$F$_3$N$_3$O | (S)-N-(1-cyclobutyl-6-(trifluoromethyl)-1H-benzo[d]imidazol-2-yl)-2,2-dimethylcyclopropane-1-carboxamide | 7 | B | 3.8 | 352 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 38 | C₁₇H₁₆F₅N₃O | N-(1-cyclobutyl-6-(trifluoromethyl)-1H-benzo[d]imidazol-2-yl)-3,3-difluorocyclobutane-1-carboxamide | 7 | B | 4.1 | 374 |
| 39 | C₁₇H₁₄F₉N₃O | N-(1-cyclobutyl-6-(trifluoromethyl)-1H-benzo[d]imidazol-2-yl)-4,4,4-trifluoro-3-(trifluoromethyl)butanamide | 7 | B | 4.6 | 448 |
| 40 | C₁₈H₂₂F₃N₃O | (R)-N-(1-cyclobutyl-6-(trifluoromethyl)-1H-benzo[d]imidazol-2-yl)-2,3-dimethylbutanamide | 7 | B | 4.0 | 354 |
| 41 | C₁₉H₂₂F₃N₃O₂ | (1S,2S)-N-(1-cyclobutyl-6-(trifluoromethyl)-1H-benzo[d]imidazol-2-yl)-2-(2-hydroxypropan-2-yl)cyclopropane-1-carboxamide | 7 | B | 3.2 | 382 |
| 42 | C₁₆H₁₅F₆N₃O₂ | (S)-N-(1-cyclobutyl-6-(trifluoromethyl)-1H-benzo[d]imidazol-2-yl)-3,3,3-trifluoro-2-hydroxy-2-methylpropanamide | 7 | B | 4.3 | 396 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 43 | C₁₆H₁₅F₆N₃O₂ | (R)-N-(1-cyclobutyl-6-(trifluoromethyl)-1H-benzo[d]imidazol-2-yl)-3,3,3-trifluoro-2-hydroxy-2-methylpropanamide | 7 | B | 4.3 | 369 |
| 44 | C₁₈H₂₀F₃N₃O₂ | N-(1-cyclobutyl-6-(trifluoromethyl)-1H-benzo[d]imidazol-2-yl)-2-(1-hydroxycyclobutyl)acetamide | 7 | B | 3.4 | 368 |
| 45 | C₁₈H₁₇F₃N₄O₂ | (S)-2,2-dimethyl-N-(1-(3-methylisoxazol-5-yl)-6-(trifluoromethyl)-1H-benzo[d]imidazol-2-yl)cyclopropane-1-carboxamide | 11 | B | 3.9 | 379 |
| 46 | C₁₈H₁₉F₃N₄O₂ | 3,3-dimethyl-N-(1-(3-methylisoxazol-5-yl)-6-(trifluoromethyl)-1H-benzo[d]imidazol-2-yl)butanamide | 9 | B | 3.9 | 381 |
| 47 | C₁₈H₁₉F₃N₄O₂ | (S)-2,3-dimethyl-N-(1-(3-methylisoxazol-5-yl)-6-(trifluoromethyl)-1H-benzo[d]imidazol-2-yl)butanamide | 11 | B | 3.9 | 381 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 48 | $C_{19}H_{21}F_3N_4O_2$ | (S)-2,3,3-trimethyl-N-(1-(3-methylisoxazol-5-yl)-6-(trifluoromethyl)-1H-benzo[d]imidazol-2-yl)butanamide | 11 | B | 4.0 | 395 |
| 49 | $C_{19}H_{21}N_5O_2$ | (S)-N-(6-cyano-1-(3-methylisoxazol-5-yl)-1H-benzo[d]imidazol-2-yl)-2,3,3-trimethylbutanamide | 11 | B | 3.6 | 352 |
| 50 | $C_{20}H_{27}N_3O_3$ | ethyl 1-cyclobutyl-2-(3,3-dimethylbutanamido)-1H-benzo[d]imidazole-6-carboxylate | 7 | B | 3.7 | 358 |
| 51 | $C_{18}H_{25}N_3O_2$ | N-(1-cyclobutyl-6-(hydroxymethyl)-1H-benzo[d]imidazol-2-yl)-3,3-dimethylbutanamide | 7 | A | 2.4 | 316 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 52 | C$_{18}$H$_{25}$N$_3$O$_2$ | (S)-N-(1-cyclobutyl-6-(hydroxymethyl)-1H-benzo[d]imidazol-2-yl)-2,3-dimethylbutanamide | 7 | B | 2.4 | 316 |
| 53 | C$_{20}$H$_{29}$N$_3$O$_2$ | N-(1-cyclobutyl-6-(2-hydroxypropan-2-yl)-1H-benzo[d]imidazol-2-yl)-3,3-dimethylbutanamide | 7 | B | 2.5 | 344 |
| 54 | C$_{20}$H$_{29}$N$_3$O$_2$ | (S)-N-(1-cyclobutyl-6-(2-hydroxypropan-2-yl)-1H-benzo[d]imidazol-2-yl)-2,3-dimethylbutanamide | 7 | B | 2.5 | 344 |
| 55 | C$_{19}$H$_{27}$N$_3$O$_2$ | N-(1-cyclobutyl-6-(1-hydroxyethyl)-1H-benzo[d]imidazol-2-yl)-3,3-dimethylbutanamide | 7 | B | 2.4 | 330 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 56 | $C_{19}H_{27}N_3O_2$ | (2S)-N-(1-cyclobutyl-6-(1-hydroxyethyl)-1H-benzo[d]imidazol-2-yl)-2,3-dimethylbutanamide | 7 | B | 2.4 | 330 |
| 57 | $C_{20}H_{29}N_3O_2$ | N-(1-cyclobutyl-6-(1-hydroxypropyl)-1H-benzo[d]imidazol-2-yl)-3,3-dimethylbutanamide | 7 | B | 2.6 | 344 |
| 58 | $C_{17}H_{20}ClN_3O$ | (S)-N-(6-chloro-1-cyclobutyl-1H-benzo[d]imidazol-2-yl)-2,2-dimethylcyclopropane-1-carboxamide | 7 | B | 3.4 | 318 |
| 59 | $C_{17}H_{22}ClN_3O$ | (S)-N-(6-chloro-1-cyclobutyl-1H-benzo[d]imidazolo-2-yl)-2,3-dimethylbutanamide | 7 | B | 3.7 | 320 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 60 | $C_{17}H_{22}ClN_3O$ | N-(6-chloro-1-cyclobutyl-1H-benzo[d]imidazol-2-yl)-3,3-dimethylbutanamide | 7 | B | 3.6 | 320 |
| 61 | $C_{17}H_{18}ClF_2N_3O$ | N-(6-chloro-1-cyclobutyl-1H-benzo[d]imidazol-2-yl)-2-(3,3-difluorocyclobutyl)acetamide | 7 | B | 3.8 | 355 |
| 62 | $C_{17}H_{20}ClN_3O_2$ | N-(6-chloro-1-cyclobutyl-1H-benzo[d]imidazol-2-yl)-2-(1-hydroxycyclobutyl)acetamide | 7 | B | 3.0 | 334 |
| 63 | $C_{17}H_{22}BrN_3O$ | N-(6-bromo-1-cyclobutyl-1H-benzo[d]imidazol-2-yl)-3,3-dimethylbutanamide | 7 | B | 3.8 | 366 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 64 | C₂₀H₂₉N₃O | N-(1-cyclobutyl-6-isopropyl-1H-benzo[d]imidazol-2-yl)-3,3-dimethylbutanamide | 7 | B | 3.2 | 328 |
| 65 | C₂₀H₂₉N₃O | (S)-N-(1-cyclobutyl-6-isopropyl-1H-benzo[d]imidazol-2-yl)-2,3-dimethylbutanamide | 7 | B | 3.4 | 328 |
| 66 | C₁₈H₂₃F₂N₃O | N-(1-cyclobutyl-6-(difluoromethyl)-1H-benzo[d]imidazol-2-yl)-3,3-dimethylbutanamide | 7 | B | 3.4 | 336 |
| 67 | C₁₉H₂₅N₃O₃ | methyl 1-cyclobutyl-2-(3,3-dimethylbutanamido)-1H-benzo[d]imidazole-7-carboxylate | 7 | B | 3.2 | 344 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 68 | C₁₈H₂₅N₃O₂ | N-(1-cyclobutyl-7-(hydroxymethyl)-1H-benzo[d]imidazol-2-yl)-3,3-dimethylbutanamide | 7 | B | 2.7 | 316 |
| 69 | C₁₈H₁₉N₅O₂ | N-(6-cyano-1-(3-methylisoxazol-5-yl)-1H-benzo[d]imidazol-2-yl)-3,3-dimethylbutanamide | 9 | B | 3.4 | 338 |
| 70 | C₂₄H₁₉FN₄O₂ | (R)-N-(6-cyano-1-(4-fluorophenyl)-1H-benzo[d]imidazol-2-yl)-3-hydroxy-3-phenylbutanamide | 7 with (R)-3-((tert-butyldimethylsilyl)oxy)-3-phenylbutanoic acid as acid, then procedure analogous to ex. 18, step E | B | 3.4 | 415 |
| 71 | C₂₁H₂₁FN₄O | (S)-N-(6-cyano-1-(4-fluorophenyl)-1H-benzo[d]imidazol-2-yl)-2,3,3-trimethylbutanamide | 7 | B | 3.6 | 365 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 72 | C₂₃H₂₄N₄O₂ | N-(6-cyano-1-cyclobutyl-1H-benzo[d]imidazol-2-yl)-3-hydroxy-2,2-dimethyl-3-phenylpropanamide | 7 | B | 3.8 | 389 |
| 73 | C₁₉H₁₈FN₅O | (S)-N-(6-cyano-1-(5-fluoropyridin-2-yl)-1H-benzo[d]imidazol-2-yl)-2,3-dimethylbutanamide | 7 | B | 3.4 | 352 |
| 74 | C₁₉H₁₈FN₅O | N-(6-cyano-1-(5-fluoropyridin-2-yl)-1H-benzo[d]imidazol-2-yl)-3,3-dimethylbutanamide | 9 | B | 3.4 | 352 |
| 75 | C₂₀H₂₀FN₅O | (S)-N-(6-cyano-1-(5-fluoropyridin-2-yl)-1H-benzo[d]imidazol-2-yl)-2,3,3-trimethylbutanamide | 7 | B | 3.6 | 366 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 76 | C₁₉H₂₄N₄O | (R)-N-(6-cyano-1-cyclobutyl-1H-benzo[d]imidazol-2-yl)-2,3,3-trimethylbutanamide | 7 | A | 5.3 | 325 |
| 77 | C₁₉H₂₄N₄O | N-(6-cyano-1-cyclobutyl-1H-benzo[d]imidazol-2-yl)-2,3,3-trimethylbutanamide | 7 | A | 5.3 | 325 |
| 78 | C₂₀H₂₄N₄O₂ | N-(6-cyano-1-cyclobutyl-1H-benzo[d]imidazol-2-yl)-3-cyclobutyl-3-hydroxybutanamide | 7 | B | 3.3 | 353 |
| 79 | C₂₃H₁₈FN₅O₂ | (S)-N-(6-cyano-1-(5-fluoropyridin-2-yl)-1H-benzo[d]imidazol-2-yl)-3-hydroxy-3-phenylbutanamide | 7 | B | 3.3 | 416 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 80 | $C_{21}H_{26}N_4O_2$ | N-(6-cyano-1-cyclobutyl-1H-benzo[d]imidazol-2-yl)-3-cyclopentyl-3-hydroxybutanamide | 7 | B | 3.5 | 367 |
| 81 | $C_{19}H_{22}N_4O_2$ | N-(6-cyano-1-cyclobutyl-1H-benzo[d]imidazol-2-yl)-2-(1-hydroxycyclopentyl)acetamide | 7 | B | 3.0 | 339 |
| 82 | $C_{20}H_{29}N_3O_2$ | N-(1-cyclobutyl-7-(2-hydroxypropan-2-yl)-1H-benzo[d]imidazol-2-yl)-3,3-dimethylbutanamide | 7, followed by method described for Ex. 53 with Ex. 67 as starting material | B | 3.5 | 344 |
| 83 | $C_{23}H_{33}N_3O_3$ | (S)-N-(1-cyclobutyl-6-(2-hydroxypropan-2-yl)-1H-benzo[d]imidazol-2-yl)-2-(6,6-dimethyltetrahydro-2H-pyran-2-yl)acetamide | 7, followed by method described for Ex. 53 | B | 2.6 | 400 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 84 | C₂₄H₂₉N₃O₃ | (S)-N-(1-(cyclobutyl-6-(2-hydroxypropan-2-yl)-1H-benzo[d]imidazol-2-yl)-3-hydroxy-3-phenylbutanamide | 7, followed by method described for Ex. 53 | B | 2.7 | 408 |
| 85 | C₁₉H₂₇N₃O₃ | N-(1-cyclobutyl-6-(2-hydroxypropan-2-yl)-1H-benzo[d]imidazol-2-yl)-3-hydroxy-3-methylbutanamide | 7, followed by method described for Ex. 53 | B | 2.1 | 346 |
| 86 | C₂₁H₃₁N₃O₂ | (S)-N-(1-cyclobutyl-6-(2-hydroxypropan-2-yl)-1H-benzo[d]imidazol-2-yl)-2,3,3-trimethylbutanamide | 7, followed by method described for Ex. 53 | B | 2.6 | 358 |
| 87 | C₂₂H₂₉N₃O₂ | N-(1-cyclobutyl-6-(2-hydroxypropan-2-yl)-1H-benzo[d]imidazol-2-yl)spiro[3.3]heptan-2-carboxamide | 7, followed by method described for Ex. 53 | B | 2.7 | 368 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 88 | C₂₂H₂₂F₃N₃O₂ | (S)-N-(1-cyclobutyl-6-(trifluoromethyl)-1H-benzo[d]imidazol-2-yl)-3-hydroxy-3-phenylbutanamide | 7 | B | 3.9 | 418 |
| 89 | C₂₀H₂₇N₃O₂ | (R)-N-(1-cyclobutyl-6-(2-hydroxypropan-2-yl)-1H-benzo[d]imidazol-2-yl)-2,2-dimethylcyclopropane-1-carboxamide | 7, followed by method described for Ex. 53 | B | 2.4 | 342 |
| 90 | C₁₉H₂₇N₃O₂ | N-(1-cyclobutyl-6-(2-hydroxypropan-2-yl)-1H-benzo[d]imidazol-2-yl)pivalamide | 7, followed by method described for Ex. 53 | B | 2.9 | 330 |
| 91 | C₂₂H₂₄N₄O₂ | (R)-N-(1-(tert-butyl)-6-cyano-1H-benzo[d]imidazol-2-yl)-3-hydroxy-3-phenylbutanamide | 7 | B | 3.6 | 369 |
| 92 | C₂₂H₂₄N₄O₂ | (S)-N-(1-(tert-butyl)-6-cyano-1H-benzo[d]imidazol-2-yl)-3-hydroxy-3-phenylbutanamide | 7 | B | 3.6 | 369 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 93 | C₁₇H₁₉F₃N₄O₂ | (S)-N-(1-(tert-butyl)-6-cyano-1H-benzo[d]imidazol-2-yl)-4,4,4-trifluoro-3-hydroxy-3-methylbutanamide | 7 | B | 3.5 | 377 |
| 94 | C₁₇H₁₉F₃N₄O₂ | (R)-N-(1-(tert-butyl)-6-cyano-1H-benzo[d]imidazol-2-yl)-4,4,4-trifluoro-3-hydroxy-3-methylbutanamide | 7 | B | 3.5 | 377 |
| 95 | C₂₃H₂₄N₄O₂ | (S)-N-(6-cyano-1-(1-methylcyclobutyl)-1H-benzo[d]imidazol-2-yl)-3-hydroxy-3-phenylbutanamide | 7 | B | 3.6 | 389 |
| 96 | C₂₃H₂₄N₄O₂ | (R)-N-(6-cyano-1-(1-methylcyclobutyl)-1H-benzo[d]imidazol-2-yl)-3-hydroxy-3-phenylbutanamide | 7 | B | 3.6 | 389 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 97 | $C_{23}H_{31}N_3O_3$ | N-(1-cyclobutyl-6-(2-hydroxypropan-2-yl)-1H-benzo[d]imidazol-2-yl)-3,3-dicyclopropyl-3-hydroxypropanamide | 7, followed by method described for Ex. 53 | B | 2.6 | 398 |
| 98 | $C_{21}H_{24}F_3N_3O_2$ | N-(1-cyclobutyl-6-(trifluoromethyl)-1H-benzo[d]imidazol-2-yl)-3,3-dicyclopropyl-3-hydroxypropanamide | 7 | B | 4.0 | 408 |
| 99 | $C_{21}H_{22}ClN_3O_2$ | (S)-N-(6-chloro-1-cyclobutyl-1H-benzo[d]imidazol-2-yl)-3-hydroxy-3-phenylbutanamide | 7 | B | 3.8 | 384 |
| 100 | $C_{21}H_{22}ClN_3O_2$ | (R)-N-(6-chloro-1-cyclobutyl-1H-benzo[d]imidazol-2-yl)-3-hydroxy-3-phenylbutanamide | 7 | B | 3.7 | 384 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 101 | $C_{21}H_{27}N_3O_2$ | N-(1-cyclobutyl-6-(2-hydroxypropan-2-yl)-1H-benzo[d]imidazol-2-yl)spiro[2.3]hexane-1-carboxamide | 7, followed by method described for Ex. 53 | B | 2.5 | 354 |
| 102 | $C_{20}H_{25}F_2N_3O_2$ | N-(1-cyclobutyl-6-(2-hydroxypropan-2-yl)-1H-benzo[d]imidazol-2-yl)-3,3-difluorocyclopentane-1-carboxamide | 7, followed by method described for Ex. 53 | B | 2.7 | 378 |
| 103 | $C_{21}H_{21}ClFN_3O_2$ | (S)-N-(6-chloro-1-cyclobutyl-1H-benzo[d]imidazol-2-yl)-3-(4-fluorophenyl)-3-hydroxybutanamide | 7 | B | 3.9 | 402 |
| 104 | $C_{22}H_{26}FN_3O_2$ | N-(1-(4-fluorophenyl)-6-(2-hydroxypropan-2-yl)-1H-benzo[d]imidazol-2-yl)-3,3-dimethylbutanamide | 7, followed by method described for Ex. 53 | B | 2.7 | 384 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 105 | $C_{20}H_{25}N_3O_2$ | N-(1-cyclobutyl-6-(2-hydroxypropan-2-yl)-1H-benzo[d]imidazol-2-yl)spiro[2.2]pentane-1-carboxamide | 7, followed by method described for Ex. 53 | B | 2.4 | 340 |
| 106 | $C_{22}H_{29}N_3O_2$ | N-(1-cyclobutyl-6-(3-hydroxypentan-3-yl)-1H-benzo[d]imidazol-2-yl)spiro[2.2]pentane-1-carboxamide | 7, followed by method described for Ex. 53 with EtMgBr | B | 2.6 | 368 |
| 107 | $C_{23}H_{19}ClFN_3O_2$ | (S)-N-(6-chloro-1-(4-fluorophenyl)-1H-benzo[d]imidazol-2-yl)-3-hydroxy-3-phenylbutanamide | 7 | B | 3.7 | 424 |
| 108 | $C_{23}H_{19}ClFN_3O_2$ | (R)-N-(6-chloro-1-(4-fluorophenyl)-1H-benzo[d]imidazol-2-yl)-3-hydroxy-3-phenylbutanamide | 7 | B | 3.7 | 424 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 109 | C₂₂H₂₂FN₃O₂ | N-(1-(4-fluorophenyl)-6-(2-hydroxypropan-2-yl)-1H-benzo[d]imidazol-2-yl)spiro[2.2]pentane-1-carboxamide | 7, followed by method described for Ex. 53 | B | 2.5 | 380 |
| 110 | C₂₁H₂₈FN₃O₃ | ethyl 2-(1-cyclobutyl-2-(3,3-dimethylbutanamido)-7-fluoro-1H-benzo[d]imidazol-6-yl)-acetate | 7 | A | 5.4 | 390 |
| 111 | C₂₁H₂₆FN₃O₃ | ethyl (S)-2-(1-cyclobutyl-2-(2,2-dimethylcyclopropane-1-carboxamido)-7-fluoro-1H-benzo[d]imidazol-6-yl)acetate) | 7 | B | 3.6 | 388 |
| 112 | C₂₃H₂₅F₂N₃O₃ | ethyl 2-(2-(3,3-dimethylbutanamido)-7-fluoro-1-(4-fluorophenyl)-1H-benzo[d]imidazol-6-yl)acetate | 7 | B | 3.7 | 430 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 113 | $C_{21}H_{28}FN_3O_2$ | (S)-N-(1-cyclobutyl-7-fluoro-6-(2-hydroxy-2-methylpropyl)-1H-benzo[d]imidazol-2-yl)-2,2-dimethylcyclopropane-1-carboxamide | 7 | B | 3.1 | 374 |
| 114 | $C_{21}H_{30}FN_3O_2$ | N-(1-cyclobutyl-7-fluoro-6-(2-hydroxy-2-methylpropyl)-1H-benzo[d]imidazol-2-yl)-3,3-dimethylbutanamide | 7, followed by method described for Ex. 53 | B | 3.2 | 376 |
| 115 | $C_{23}H_{25}F_2N_3O_2$ | (S)-N-(7-fluoro-1-(4-fluorophenyl)-6-(2-hydroxy-2-methylpropyl)-1H-benzo[d]imidazol-2-yl)-2,2-dimethylcyclopropane-1-carboxamide | 7, followed by method described for Ex. 53 | B | 3.1 | 414 |
| 116 | $C_{23}H_{27}F_2N_3O_2$ | N-(7-fluoro-1-(4-fluorophenyl)-6-(2-hydroxy-2-methylpropyl)-1H-benzo[d]imidazol-2-yl)-3,3-dimethylbutanamide | 7, followed by method described for Ex. 53 | B | 3.2 | 416 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 117 | $C_{19}H_{24}FN_3O_3$ | 2-(1-cyclobutyl-2-(3,3-dimethylbutanamido)-7-fluoro-1H-benzo[d]imidazol-6-yl)acetic acid | 7 | B | 2.9 | 362 |
| 118 | $C_{21}H_{29}FN_4O_2$ | N-(1-cyclobutyl-6-(2-(dimethylamino)-2-oxoethyl)-7-fluoro-1H-benzo[d]imidazol-2-yl)-3,3-dimethylbutanamide | 7 | B | 2.9 | 389 |
| 119 | $C_{23}H_{26}N_4O_2$ | (S)-N-(1-(tert-butyl)-6-cyano-5-methyl-1H-benzo[d]imidazol-2-yl)-3-hydroxy-3-phenylbutanamide | 7 | B | 3.7 | 391 |
| 120 | $C_{23}H_{26}N_4O_2$ | (R)-N-(1-(tert-butyl)-6-cyano-5-methyl-1H-benzo[d]imidazol-2-yl)-3-hydroxy-3-phenylbutanamide | 7 | B | 3.7 | 391 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 121 | C₂₃H₂₅FN₄O₂ | (S)-N-(1-(tert-butyl)-6-cyano-5-methyl-1H-benzo[d]imidazol-2-yl)-3-(4-fluorophenyl)-3-hydroxybutanamide | 7 | B | 3.8 | 409 |
| 122 | C₂₃H₂₅FN₄O₂ | (S)-N-(1-(tert-butyl)-6-cyano-5-methyl-1H-benzo[d]imidazol-2-yl)-3-(2-fluorophenyl)-3-hydroxybutanamide | 7 | B | 3.9 | 409 |
| 123 | C₂₃H₂₄N₄O₂ | (S)-N-(6-cyano-1-cyclobutyl-5-methyl-1H-benzo[d]imidazol-2-yl)-3-hydroxy-3-phenylbutanamide | 7 | B | 3.5 | 389 |
| 124 | C₂₃H₂₄N₄O₂ | (R)-N-(6-cyano-1-cyclobutyl-5-methyl-1H-benzo[d]imidazol-2-yl)-3-hydroxy-3-phenylbutanamide | 7 | B | 3.5 | 389 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 125 | C₂₃H₂₃FN₄O₂ | (S)-N-(6-cyano-1-cyclobutyl-5-methyl-1H-benzo[d]imidazol-2-yl)-3-(4-fluorophenyl)-3-hydroxybutanamide | 7 | B | 3.6 | 407 |
| 126 | C₂₃H₂₃FN₄O₂ | (S)-N-(6-cyano-1-cyclobutyl-5-methyl-1H-benzo[d]imidazol-2-yl)-3-(2-fluorophenyl)-3-hydroxybutanamide | 7 | B | 3.7 | 407 |
| 127 | C₁₉H₂₆N₄O | N-(1-(tert-butyl)-6-cyano-5-methyl-1H-benzo[d]imidazol-2-yl)-3,3-dimethylbutanamide | 7 | B | 3.9 | 327 |
| 128 | C₁₈H₂₄N₄O₂ | N-(1-(tert-butyl)-6-cyano-5-methyl-1H-benzo[d]imidazol-2-yl)-3-hydroxy-3-methylbutanamide | 7 | B | 2.8 | 329 |
| 129 | C₁₈H₂₀F₂N₄O | N-(1-(tert-butyl)-6-cyano-5-methyl-1H-benzo[d]imidazol-2-yl)-3,3-difluorocyclobutane-1-carboxamide | 7 | B | 3.9 | 347 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 130 | $C_{18}H_{24}N_4O_2$ | N-(6-cyano-1-cyclobutyl-5-methyl-1H-benzo[d]imidazol-2-yl)-3-hydroxy-3-methylbutanamide | 7 | B | 2.8 | 327 |
| 131 | $C_{21}H_{18}F_7N_3O_3$ | 4,4,4-trifluoro-N-(1-(4-fluorophenyl)-6-(2-hydroxypropan-2-yl)-1H-benzo[d]imidazol-2-yl)-3-hydroxy-3-(trifluoromethyl)butanamide | 7, followed by method described for Ex. 53 | B | 3.8 | 494 |
| 132 | $C_{17}H_{16}F_7N_3O_2$ | (R)-N-(1-cyclobutyl-7-fluoro-5-(trifluoromethyl)-1H-benzo[d]imidazol-2-yl)-4,4,4-trifluoro-3-hydroxy-3-methylbutanamide | 7 | B | 4.1 | 428 |
| 133 | $C_{17}H_{19}F_4N_3O_2$ | N-(1-cyclobutyl-7-fluoro-5-(trifluoromethyl)-1H-benzo[d]imidazol-2-yl)-3-hydroxy-3-methylbutanamide | 7 | B | 3.5 | 374 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 134 | C₁₈H₂₁F₃N₄O₂ | (S)-N-(1-(tert-butyl)-6-cyano-5-methyl-1H-benzo[d]imidazol-2-yl)-4,4,4-trifluoro-3-hydroxy-3-methylbutanamide | 7 | B | 3.8 | 383 |
| 135 | C₁₈H₂₁F₃N₄O₂ | (R)-N-(1-(tert-butyl)-6-cyano-5-methyl-1H-benzo[d]imidazol-2-yl)-4,4,4-trifluoro-3-hydroxy-3-methylbutanamide | 7 | B | 3.8 | 383 |
| 136 | C₁₉H₁₆F₅N₃O₂ | N-(1-(3,5-difluorophenyl)-6-(trifluoromethyl)-1H-benzo[d]imidazol-2-yl)-3-hydroxy-3-methylbutanamide | 7 | B | 3.4 | 414 |
| 137 | C₂₀H₁₇F₆N₃O₃ | 3-hydroxy-3-methyl-N-(1-(4-(trifluoromethoxy)phenyl)-6-(trifluoromethyl)-1H-benzo[d]imidazol-2-yl)butanamide | 7 | B | 3.5 | 462 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 138 | C₂₃H₂₃FN₄O₂ | (S)-N-(6-cyano-1-(1-methylcyclobutyl)-1H-benzo[d]imidazol-2-yl)-3-(4-fluorophenyl)-3-hydroxybutanamide | 7 | B | 3.7 | 407 |
| 139 | C₂₃H₂₃ClN₄O₂ | (S)-3-(2-chlorophenyl)-N-(6-cyano-1-(1-methylcyclobutyl)-1H-benzo[d]imidazol-2-yl)-3-hydroxybutanamide | 7 | B | 4.0 | 423 |
| 140 | C₂₃H₂₃ClN₄O₂ | (S)-3-(4-chlorophenyl)-N-(6-cyano-1-(1-methylcyclobutyl)-1H-benzo[d]imidazol-2-yl)-3-hydroxybutanamide | 7 | A | 5.7 | 423 |
| 141 | C₂₀H₁₆F₅N₃O₂ | N-(1-(3,5-difluorophenyl)-6-(trifluoromethyl)-1H-benzo[d]imidazol-2-yl)-2-(1-hydroxycyclobutyl)acetamide | 7 | B | 3.6 | 426 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 142 | C$_{21}$H$_{17}$F$_6$N$_3$O$_3$ | 2-(1-hydroxycyclobutyl)-N-(1-(4-(trifluoromethoxy)phenyl)-6-(trifluoromethyl)-1H-benzo[d]imidazol-2-yl)acetamide | 7 | B | 3.8 | 474 |
| 143 | C$_{19}$H$_{16}$F$_5$N$_3$O$_2$ | N-(1-(3,4-difluorophenyl)-6-(trifluoromethyl)-1H-benzo[d]imidazol-2-yl)-3-hydroxy-3-methylbutanamide | 7 | B | 3.4 | 414 |
| 144 | C$_{20}$H$_{16}$F$_7$N$_3$O$_3$ | N-(1-(3-fluoro-4-(trifluoromethoxy)phenyl)-6-(trifluoromethyl)-1H-benzo[d]imidazol-2-yl)-3-hydroxy-3-methylbutanamide | 7 | B | 3.8 | 480 |

TABLE 1-continued

List of Examples, Synthetic Routes and Analytical Data

| Ex. | Structure | Name | Coupling Method/ final step | HPLC Method | HPLC Retention time (min) | LCMS m/z |
|---|---|---|---|---|---|---|
| 145 | 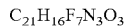 C₂₁H₁₆F₇N₃O₃ | N-(1-(3-fluoro-4-(trifluoromethoxy)phenyl)-6-(trifluoromethyl)-1H-benzo[d]imidazol-2-yl)-2-(1-hydroxycyclobutyl)acetamide | 7 | B | 3.9 | 492 |

Biological Assay Methods

Kv7.2/7.3 Activation Assay

The ability of compounds to potentiate K-currents in Kv7.2/7.3 containing HEK cells was assessed using planar patch-clamp on the QPatch automated screening platform.

Cell Line: The hKv7.2/7.3 cell line was obtained from Chantest (Cleveland, Ohio 44128) cat.# CT6147. These HEK cells will express the Kv7.2/7.3 ion channels when induced.

Cell Culture: Cells were maintained in a media containing DMEM/F12; 50/50 (GIBCO cat.#11330), 10% Fetal Bovine Serum (FBS) (GIBCO cat.#26140), 100 units/mL Penicillin-Streptomycin (GIBCO cat.#15140), 0.005 mg/mL Blasticidin (INVIVOGEN cat.# ant-bl-1), 0.5 mg/mL Geneticin (GIBCO cat.#10131), 0.1 mg/mL Zeocin (GIBCO cat.# R25001). Cells used in the electrophysiology assay were maintained in a media without Blasticidin, Geneticin and Zeocin for 2 days and channel expression was induced by adding tetracycline (BIOLINE cat.# B10-87030) at a final concentration of 1 mg/mL. Cells were grown in T-175 flask to ~75% confluency. Currents were recorded 24 hours after channel induction.

Compound Plates: Test compounds were prepared by performing serial dilutions on a Biomek NX$^P$ (BECKMAN COULTER). Final dilutions were made in external recording solution with a final DMSO concentration of 0.1% DMSO. For single concentration screens each plate had 10 μM retigabine as a positive control and 0.1% DMSO as a negative control.

Electrophysiology: On the day of the experiment cells were washed with Hank's Balanced Salt Solution (HBBS) (GIBCO cat.#14175) and harvested with Tryple (GIBCO cat.#12604). Cells were then centrifuged at 2000 rpm for 5 minutes and resuspended in CHO-S-SFM (GIBCO cat.#12052) at ~3×10⁶ cells/mL. Cells were stirred for 30 minutes before experiments were started. External recording solution contained (in mM): NaCl (145), KCl (4), CaCl₂ (2), MgCl₂ (1), HEPES (10) and Glucose (10); pH was adjusted to 7.4 with NaOH and the osmolarity was adjusted to 300-305 mOsM with sucrose if necessary. Internal solution contained (in mM): KCl (125), KF (10), EGTA (5), Na₂ATP (5), MgCl₂ (3.2), HEPES (5); pH was adjusted to 7.2 with KOH and the osmolarity was adjusted to 298-302 mOsM with sucrose.

Potassium channel activity was measured on the QPatch HTX (Sophion Bioscience) using QPlates with 48-wells/plate. Each cell was taken as an independent experiment and only one compound was tested per well. Potassium channel activity was elicited by holding at -80 mV and stepping to -30 mV for 2 s followed by a 100 ms pulse to -120 mV.

Single Concentration Screen: Baseline conditions were obtained by recording 5 sweeps in the external solution only, this was repeated for three applications of the external solution. The effect of test compounds on elicited current was then assessed by recording 5 sweeps in the presence of a 3 μM compound solution. The steady-state current at the end of the 2 s pulse to -30 mV was measured to determine the fold increase from baseline.

TABLE 2

Kv7.2/7.3 Single Concentration Screen Results.

| Example | Kv7.2/7.3 Activity* |
|---|---|
| 1 | + |
| 2 | + |
| 3 | +++ |
| 4 | +/− |
| 5 | +++ |
| 6 | + |
| 7 | + |
| 8 | + |
| 9 | + |
| 10 | + |
| 11 | ++ |
| 12 | +/− |
| 13 | +/− |
| 14 | +/− |
| 15 | +/− |
| 16 | +/− |
| 17 | ++ |
| 18 | + |
| 19 | + |
| 20 | + |
| 21 | +/− |
| 22 | +/− |

TABLE 2-continued

Kv7.2/7.3 Single Concentration Screen Results.

| Example | Kv7.2/7.3 Activity* |
|---|---|
| 23 | ++ |
| 24 | + |
| 25 | +/− |
| 26 | +/− |
| 27 | +/− |
| 28 | +/− |
| 29 | + |
| 30 | + |
| 31 | + |
| 32 | + |
| 33 | + |
| 34 | ++ |
| 35 | + |
| 36 | + |
| 37 | + |
| 38 | +/− |
| 39 | + |
| 40 | + |
| 41 | +/− |
| 42 | +/− |
| 43 | +/− |
| 44 | + |
| 45 | + |
| 46 | + |
| 47 | + |
| 48 | +++ |
| 49 | + |
| 50 | +/− |
| 51 | + |
| 52 | +/− |
| 53 | + |
| 54 | ++ |
| 55 | + |
| 56 | ++ |
| 57 | + |
| 58 | + |
| 59 | + |
| 60 | + |
| 61 | + |
| 62 | + |
| 63 | ++ |
| 64 | ++ |
| 65 | + |
| 66 | ++ |
| 67 | +/− |
| 68 | + |
| 69 | + |
| 70 | +/− |
| 71 | + |
| 72 | +/− |
| 73 | +/− |
| 74 | + |
| 75 | ++ |
| 76 | + |
| 77 | + |
| 78 | + |
| 79 | + |
| 80 | + |
| 81 | + |
| 82 | +/− |
| 83 | ++ |
| 84 | + |
| 85 | +/− |
| 86 | +++ |
| 87 | ++ |
| 88 | + |
| 89 | ++ |
| 90 | +/− |
| 91 | +/− |
| 92 | + |
| 93 | + |
| 94 | +/− |
| 95 | ++ |
| 96 | ++ |
| 97 | +/− |
| 98 | + |
| 99 | + |
| 100 | + |
| 101 | + |
| 102 | +/− |
| 103 | + |
| 104 | + (@ 1 µM) |
| 105 | + |
| 106 | +/− |
| 107 | + |
| 108 | +/− |
| 109 | + |
| 110 | + |
| 111 | + |
| 112 | ++ |
| 113 | + |
| 114 | + |
| 115 | + |
| 116 | + |
| 117 | +/− |
| 118 | + |
| 119 | +/− |
| 120 | + |
| 121 | + |
| 122 | ++ |
| 123 | +/− |
| 124 | +/− |
| 125 | +/− |
| 126 | ++ |
| 127 | + |
| 128 | +/− |
| 129 | +/− |
| 130 | +/− |
| 131 | +/− |
| 132 | +/− |
| 133 | + |
| 134 | +/− |
| 135 | +/− |
| 136 | + |
| 137 | + |
| 138 | + |
| 139 | + |
| 140 | +/− |
| 141 | + |
| 142 | ++ |
| 143 | ++ |
| 144 | + |
| 145 | ++ |

*Increase in current from Kv7.2/Kv7.3 co-expressing HEK cells, measured at compound concentration of 3 µM, as a range from <1.2-fold increase over baseline (−) up to >6-fold increase over baseline (+++).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A compound of Formula 2:

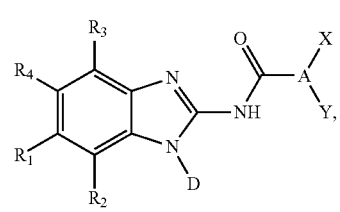

or a pharmaceutically acceptable salt thereof;
wherein
D is optionally substituted cyclobutyl, or t-butyl;
A is $C_{2-8}$ alkyl;
X is H, $CF_3$, or optionally substituted phenyl;
Y is H or OH;
$R^1$ is CN or $C_{1-4}$ hydroxyalkyl; and
$R^2$, $R^3$, and $R^4$ are independently H, or F.

2. The compound of claim 1, wherein $R^1$ is CN, —C(CH$_3$)$_2$OH, or —CH$_2$C(CH$_3$)$_2$OH.

3. The compound of claim 1, wherein $R^2$ is F.

4. The compound of claim 1, wherein $R^3$ is H.

5. The compound of claim 1, wherein $R^4$ is H.

6. The compound of claim 1, wherein $R^1$ is CN.

7. The compound of claim 1, wherein $R^1$ is $C_{1-4}$ hydroxyalkyl.

8. The compound of claim 1, wherein X is optionally substituted phenyl.

9. The compound of claim 1, wherein X is $CF_3$.

10. The compound of claim 1, wherein X is H.

11. The compound of claim 1, wherein Y is H.

12. The compound of claim 1, wherein Y is OH.

13. A method of mitigating epilepsy in a mammal in need thereof, comprising administering an effective amount of the compound of claim 1 to the mammal.

14. A method of mitigating pain in a mammal in need thereof, comprising administering an effective amount of the compound of claim 1 to the mammal.

15. The method of claim 14, wherein the pain is neuropathic pain, inflammatory pain, persistent pain, cancer pain, or postoperative pain.

16. A method of mitigating migraine in a mammal in need thereof, comprising administering an effective amount of the compound of claim 1 to the mammal.

* * * * *